US 6,696,552 B2

(12) United States Patent
Mayo et al.

(10) Patent No.: US 6,696,552 B2
(45) Date of Patent: Feb. 24, 2004

(54) PROCESS FOR PREPARING SUBSTITUTED PYRIDONE COMPOUNDS

(75) Inventors: James D. Mayo, Mississauga (CA); James M. Duff, Mississauga (CA); Rina Carlini, Mississauga (CA); Roger E. Gaynor, Oakville (CA); George Liebermann, Mississauga (CA)

(73) Assignee: Xerox Corporation, Stamford, CT (US)

( * ) Notice: Subject to any disclaimer, the term of this patent is extended or adjusted under 35 U.S.C. 154(b) by 59 days.

(21) Appl. No.: 10/185,597

(22) Filed: Jun. 27, 2002

(65) Prior Publication Data

US 2004/0006234 A1 Jan. 8, 2004

(51) Int. Cl.[7] .................. C09B 41/00; C07D 213/85; C07D 213/69
(52) U.S. Cl. ............... 534/649; 534/758; 534/DIG. 2; 546/249; 546/250
(58) Field of Search ................. 546/249, 250; 534/649, 758, DIG. 2

(56) References Cited

U.S. PATENT DOCUMENTS

| 3,668,211 A | * | 6/1972 | Crabtree .............. 546/288 |
| 3,929,863 A | | 12/1975 | Blahak et al. .............. 260/471 |
| 3,957,749 A | | 5/1976 | von Brachel et al. ....... 260/156 |
| 4,083,842 A | | 4/1978 | Burkhard et al. ........... 260/156 |
| 4,216,145 A | | 8/1980 | Battisti et al. ............ 260/156 |
| 4,247,456 A | | 1/1981 | von Brachel et al. ....... 260/156 |
| 4,284,782 A | * | 8/1981 | Schmidt ............... 546/288 |
| 4,359,418 A | | 11/1982 | Lienhard et al. ........... 260/156 |
| 4,380,452 A | | 4/1983 | Loeffler et al. ............. 8/532 |

(List continued on next page.)

FOREIGN PATENT DOCUMENTS

| DE | 2 040 644 | 12/1975 |
| DE | 3538517 A1 | 5/1986 |
| EP | 0 013 956 | 8/1980 |
| EP | 0 023 770 A1 | 2/1981 |
| EP | 0 083 553 A1 | 12/1982 |
| EP | 0 142 863 B1 | 5/1985 |
| EP | 0 172 283 A1 | 2/1986 |
| EP | 0 247 737 A1 | 12/1987 |

(List continued on next page.)

OTHER PUBLICATIONS

Copending application U.S. Ser. No. 10/185,261, filed Jun. 27, 2002, entitled "Processes for Preparing Dianthranilate Compounds and Diazopyridone Colorants," by Rina Carlini et al.

(List continued on next page.)

Primary Examiner—Fiona T. Powers
(74) Attorney, Agent, or Firm—Judith L. Byorick

(57) ABSTRACT

A process which comprises admixing in the absence of a solvent an amine of the formula $R_1$—$NH_2$ and a first ester of the formula

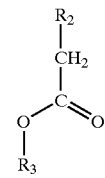

wherein $R_2$ is an electron withdrawing group and $R_3$ is an alkyl group; heating the mixture containing the amine and the first ester to form an intermediate compound of the formula

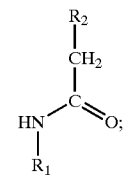

admixing the intermediate compound with a base and a second ester of the formula

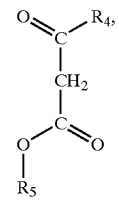

said second ester being present in a molar excess relative to the intermediate compound, said base being present in a molar excess relative to the intermediate compound, and heating the mixture to form a pyridone compound of the formula

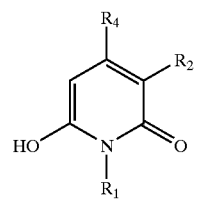

or a salt thereof. Also disclosed is a process for preparing diazopyridone colorants which comprises preparing a pyridone compound by the above process and reacting the pyridone compound with a diazonium salt to form a diazopyridone compound.

44 Claims, No Drawings

U.S. PATENT DOCUMENTS

| | | | |
|---|---|---|---|
| 4,644,058 A | 2/1987 | Shimidzu et al. | 534/635 |
| 4,734,349 A | 3/1988 | Chapman et al. | 430/106 |
| 4,739,042 A | 4/1988 | Lorenz et al. | 534/649 |
| 4,889,560 A | 12/1989 | Jaeger et al. | 106/27 |
| 4,889,761 A | 12/1989 | Titterington et al. | 428/195 |
| 4,994,564 A | 2/1991 | Etzbach et al. | 534/766 |
| 5,006,170 A | 4/1991 | Schwarz et al. | 106/20 |
| 5,037,964 A | 8/1991 | Moser et al. | 534/608 |
| 5,041,413 A | 8/1991 | Evans et al. | 503/227 |
| 5,066,791 A | 11/1991 | Hansen et al. | 534/772 |
| 5,372,852 A | 12/1994 | Titterington et al. | 427/288 |
| 5,413,630 A * | 5/1995 | Schwarz et al. | 106/31.48 |
| 5,554,737 A * | 9/1996 | Lamm et al. | 534/758 |
| 5,621,022 A | 4/1997 | Jaeger et al. | 523/161 |
| 5,827,918 A | 10/1998 | Titterington et al. | 524/590 |
| 5,902,841 A | 5/1999 | Jaeger et al. | 523/161 |
| 5,919,839 A | 7/1999 | Titterington et al. | 523/161 |
| 5,929,218 A | 7/1999 | Lee et al. | 534/772 |
| 6,086,637 A * | 7/2000 | Grund et al. | 8/471 |
| 6,406,526 B1 | 6/2002 | Meyrick et al. | 106/31.48 |

FOREIGN PATENT DOCUMENTS

| | | |
|---|---|---|
| EP | 268897 | 6/1988 |
| EP | 0 302 401 A1 | 7/1988 |
| EP | 0 314 002 B1 | 9/1991 |
| EP | 0 468 647 B1 | 1/1992 |
| EP | 0 404 493 B1 | 5/1994 |
| EP | 0 319 234 B1 | 3/1995 |
| EP | 0 524 637 B1 | 3/1996 |
| EP | 0 529 282 B1 | 10/1996 |
| EP | 0 706 679 B1 | 9/1997 |
| EP | 0 844 287 B1 | 5/2000 |
| EP | 1 125 990 A1 | 8/2001 |
| EP | 1 168 046 A1 | 1/2002 |
| GB | 2 008 606 A | 6/1979 |
| GB | 1 559 001 | 1/1980 |
| GB | 1593822 * | 7/1981 |
| IN | 147868 | 7/1980 |
| KR | 119563 | 8/1997 |
| WO | WO 95/00885 | 1/1995 |
| WO | WO 99/43754 | 9/1999 |
| WO | WO 01/21714 A2 | 3/2001 |
| WO | WO 01/09256 A1 | 8/2001 |

OTHER PUBLICATIONS

Copending application U.S. Ser. No. 10/185,994, filed Jun. 27, 2002, entitled "Dimeric Azo Pyridone Colorants," by Rina Carlini et al.

Copending application U.S. Ser. No. 10/184,269, filed Jun. 27, 2002, entitled "Phase Change Inks Containing Dimeric Azo Pyridone Colorants," by Bo Wu et al.

Copending application U.S. Ser. No. 10/185,264, filed Jun. 27, 2002, entitled "Phase Change Inks Containing Azo Pyridone Colorants" by Jeffery H. Banning et al.

Copending application U.S. Ser. No. 10/186,024, filed Jun. 27, 2002, entitled "Azo Pyridone Colorants," by Jeffery H. Banning etal.

Copending application U.S. Ser. No. 10/186,023, filed Jun. 27, 2002, entitled "Dimeric Azo Pyridone Colorants," by Rina Carlini et al.

Copending application U.S. Ser. No. 10/184,266, filed Jun. 27, 2002, entitled "Phase Change Inks Containing Dimeric Azo Pyridone Colorants," by Bo Wu et al.

Copending application U.S. Ser. No. 10/185,828, filed Jun. 27, 2002, entitled "Method for Making Dimeric Azo Pyridone Colorants," by Rina Carlini et al.

English Abstract for German Patent Publication DE 2 902 740.

"Polyamines Containing Ester Groups as Structural Components in Polyurethane Chemistry", J. Blahak et al., Angew. Makromol. Chem. (1972), vol. 26, pp. 29 to 45.

"The Chemistry of Isatoic Anhydride," G. M. Coppola, Synthesis, p. 505 (1980).

"Isatoic Anhydride. IV. Reactions with Various Nucleophiles," R. P. Staiger et al., J. Org. Chem., vol. 24, p. 1214 (1959).

English Abstract for German Patent Publication DE 19646430.

English Abstract for German Patent Publication DE 19646429.

English Abstract for German Patent Publication DE 19647869.

English Abstract for Japanese Patent Publication JP 3192158.

"Preparation and Evaluation of Yellow Pigments Based on H–Pyridone and Esters of Aminoterephthalic Acid," P. Slosar et al., CHEMagazin, vol. 9, No. 6, pp. 8–11 (1999) (Not translated).

"Synthesis, Morphology, and Optical Properties of Tetrahedral Oligo(phenylenevinylene) Materials," S. Wang et al., J. Am. Chem. Soc., vol. 120, p. 5695 (2000).

"Syntheses of Amphiphilic Diblock Copolymers Containing a Conjugated Block and Their Self–Assembling Properties," H. Wang et al., J. Am. Chem. Soc., vol. 122, p. 6855 (2000).

"Crystal Engineering of Conjugated Oligomers and the Spectral Signature of π Stacking in Conjugated Oligomers and Polymers," A. Koren et al., Chem. Mater., vol. 12, p. 1519 (2000).

"Investigation of the Reaction Conditions for the Synthesis of 4,6–Disubstituted–3–cyano–2–pyridones and 4–Methyl–3–cyano–6–hydroxy–2–pyridone," D. Z. Mijin et al., J. Serb. Chem. Soc., vol. 59, No. 12, p. 959 (1994).

Synthesis of Isoquinoline Alkaloids. II. The Synthesis and Reactions of 4–Methyl–3– pyridinecarboxaldehyde and Other 4–Methyl–3–substituted Pyridines, J. M. Bobbitt et al., J. Org. Chem., vol. 25, p. 560 (1960).

"Synthesis and Dyeing Characteristics of 5–(4–Arylazophenyl) azo–3–cyano–4–methyl–6–hydroxy–2–pyridones," J. Kanhere et al., Indian Journal of Textile Research, vol. 13, p. 213 (1988).

English Abstract and description (not translated) for German Patent Publication DE 3543360.

English Abstract for Japanese Patent Publication JP 2001214083.

English Abstract for German Patent Publication DE 3505899.

"Yellow to Violet Azo–N–Substituted Pyridinone Disperse Dyes for Synthetic Fibers," I.M.S. Mamak, Indian, pp. 1–11 (1980) (Indian Patent Publication 147527).

English Abstract for Japanese Patent Publication JP2000062327.

English Abstract for Japanese Patent Publication JP60152563.

"Synthesis of 3–Cyano–6–hydroxy–5–(2–[perfluoroalkyl)phenylazo]–2–pyridones and their Application for Dye Diffusion Thermal Transfer Printing," Bull. Chem. Soc. Jpn., vol. 66, Iss. 6, pp. 1790–1794, (1993).

English Abstract for Chinese Patent Publication CN1115773.

English Abstract for German Patent Publication DE 3447117.
English Abstract for Japanese Patent Publication JP 5331382.
English Abstract for Japanese Patent Publication JP 63210169.
English Abstract for Japanese Patent Publication JP 63199764.
English Abstract for Japanese Patent Publication JP 63199763.
English Abstract for Japanese Patent Publication JP 63199762.
English Abstract for Japanese Patent Publication JP 63199761.
English Abstract for Japanese Patent Publication JP 63199760.
English Abstract for Japanese Patent Publication JP 63071392.
English Abstract for Japanese Patent Publication JP 61181865.
English Abstract for Japanese Patent Publication JP 61036366.
English Abstract for Japanese Patent Publication JP 60112862.
English Abstract for Japanese Patent Publication JP 60112861.
English Abstract for Japanese Patent Publication JP 58149953.
English Abstract for Japanese Patent Publication JP 56092961.
English Abstract for Japanese Patent Publication JP 56026957.
English Abstract for Japanese Patent Publication JP 55099958.
English Abstract for Japanese Patent Publication JP 96 11443 (JP8011443).
English Abstract for Japanese Patent Publication JP 93169849 (JP5169849).
English Abstract for Japanese Patent Publication JP 93 51536 (JP5051536).
English Abstract for Japanese Patent Publication JP 90185569 (JP2185569).
English Abstract for Japanese Patent Publication JP 87290762 (JP62290762).
English Abstract for Japanese Patent Publication JP 86244595 (JP61244595).
English Abstract for Spanish Patent Publication 475254 (Equivalent of Italian Patent Publication IT 1088895).
English Abstract for German Patent Publication DE 2727809.
"Colour and Constitution of Azo Dyes Derived from 2–Thioalkyl–4,6–Diaminopyrimidines and 3–Cyano–1, 4–dimethyl–6–hydroxy–2–pyridone as Coupling Components," L. Cheng et al., *Dyes and Pigments*, vol. 7, No. 5, pp. 373–388 (1986).
English Abstract for Japanese Patent Publication JP 63039380.
English Abstract for Japanese Patent Publication JP 54102328.
English Abstract for Japanese Patent Publication JP 54070337.
"Trends in Modern Dye Chemistry. Part 10," N. R. Ayyangar and K. V. Srinivasan, *Colourage*, vol. 37, No. 2, pp. 29–30 (Jan. 16, 1990).
English Abstract for Japanese Patent Publication JP 05169854.
English Abstract for Japanese Patent Publication JP 04292988.
English Abstact for Japanese Patent Publication JP 63161060.
English Abstract for Japanese Patent Publication JP 61244595.
English Abstract for Japanese Patent Publication JP 00239549 (JP2000239549).
English Abstract for Japanese Patent Publication JP 11269402.
English Abstract for Japanese Patent Publication JP 09041267.
English Abstract for Japanese Patent Publication JP 08039941.
English Abstract for Japanese Patent Publication JP 06294909.
English Abstract for Japanese Patent Publication JP 06122829.
English Abstract for Japanese Patent Publication JP 05255602.
English Abstract for Japanese Patent Publication JP 05051536.
English Abstract for Japanese Patent Publication JP 04235093.
English Abstract for European Patent Publication EP 0 063 275.
English Abstract for German Patent Publication DE 2606506.

* cited by examiner

PROCESS FOR PREPARING SUBSTITUTED PYRIDONE COMPOUNDS

Cross-reference Is made to the following applications:
Copending application U.S. Ser. No. 10/185,261, filed concurrently herewith, entitled "Processes for Preparing Dianthranilate Compounds and Diazopyridone Colorants," with the named inventors Rina Carlini, James M. Duff, Stephen G. Robinson, George Liebermann, Roger E. Gaynor, Tania L. Pereira, Jeffery H. Banning, and James D. Mayo, the disclosure of which is totally incorporated herein by reference, discloses a process for preparing dianthranilate compounds which comprises (a) admixing reactants as follows: (1) a diol of the formula $R_1(OH)_2$, wherein $R_1$ is an alkylene group having at least about 20 carbon atoms, and wherein the —OH groups are primary or secondary, (2) isatoic anhydride, present in an amount of at least about 2 moles of isatoic anhydride per every one mole of diol, (3) a catalyst which is 1,4-diazabicyclo[2.2.2]octane, N,N,N',N'-tetramethylethylene diamine, or a mixture thereof, said catalyst being present in an amount of at least about 0.2 mole of catalyst per every one mole of diol, and (4) a solvent; and (b) heating the mixture thus formed to form a dianthranilate compound of the formula

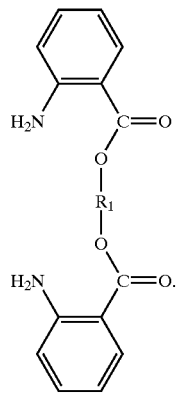

Also disclosed is a process for preparing diazopyridone colorants which comprises (I) preparing a dianthranilate compound by the aforementioned method, (II) reacting the dianthranilate compound with nitrosylsulfuric acid to form a diazonium salt, and (III) reacting the diazonium salt with a pyridone compound to form a diazopyridone compound.

Copending application U.S. Ser. No. 10/185,994, filed concurrently herewith, entitled "Dimeric Azo Pyridone Colorants," with the named inventors Rina Carlini, Jeffery H. Banning, James M. Duff, Bo Wu, and James D. Mayo, the disclosure of which is totally incorporated herein by reference, discloses compounds of the formula

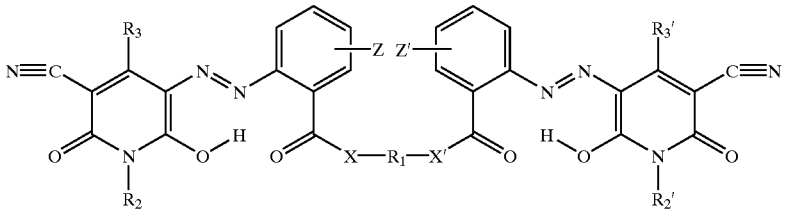

The compounds are useful as colorants, particularly in applications such as phase change inks.

Copending application U.S. Ser. No. 10/184,269, filed concurrently herewith, entitled "Phase Change Inks Containing Dimeric Azo Pyridone Colorants," with the named inventors Bo Wu, Rina Carlini, Jeffery H. Banning, James M. Duff, James D. Mayo, Jule W. Thomas, Paul F. Smith, and Michael B. Meinhardt, the disclosure of which is totally incorporated herein by reference, discloses a phase change ink composition comprising a phase change ink carrier and a colorant compound of the formula

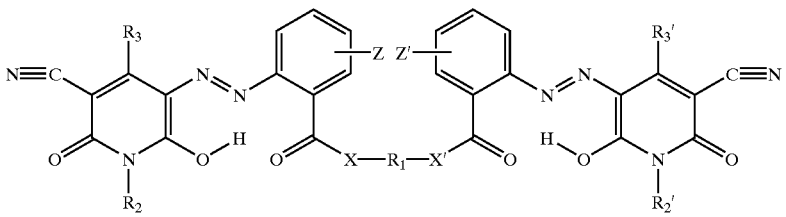

Copending application U.S. Ser. No. 10/185,264, filed concurrently herewith, entitled "Phase Change Inks Containing Azo Pyridone Colorants" with the named inventors Jeffery H. Banning, Bo Wu, James D. Mayo, James M. Duff, Rina Carlini, Jule W. Thomas, and Paul F. Smith, the disclosure of which is totally incorporated herein by reference, discloses a phase change ink composition comprising a phase change ink carrier and a colorant compound of the formula

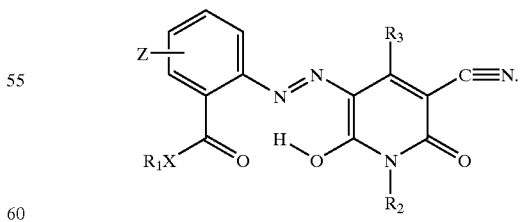

Copending application U.S. Ser. No. 10/186,024, filed concurrently herewith, entitled "Azo Pyridone Colorants," with the named inventors Jeffery H. Banning, Rina Carlini, James D. Mayo, James M. Duff, and C. Wayne Jaeger, the disclosure of which is totally incorporated herein by reference, discloses compounds of the formula

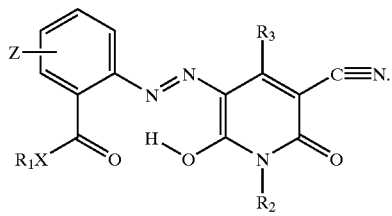

The compounds are useful as colorants, particularly in applications such as phase change inks.

Copending application U.S. Ser. No. 10/185,828, filed concurrently herewith, entitled "Method for Making Dimeric Azo Pyridone Colorants," with the named inventors Rina Carlini, James D. Mayo, James M. Duff, Jeffery H. Banning, Paul F. Smith, George Liebermann, and Roger E. Gaynor, the disclosure of which is totally incorporated herein by reference, discloses a process for preparing a diazopyridone compound which comprises (a) preparing a first solution comprising (1) either (A) a dianiline of the formula

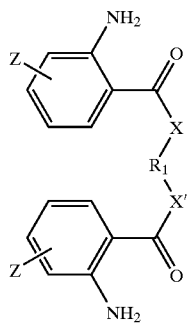

or (B) an aniline of the formula

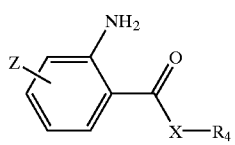

and (2) a first solvent mixture comprising (I) a solvent, (II) acetic acid, and (III) an optional second acid, said acetic acid being present in the solvent mixture in an amount of at least about 95 percent by weight of the solvent mixture, said first solution being at a temperature of about +15° C. or lower; (b) adding to the first solution nitrosylsulfuric acid, thereby forming a diazonium salt either (A) of the formula

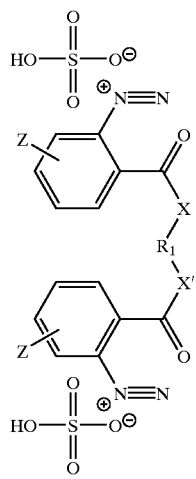

or (B) of the formula

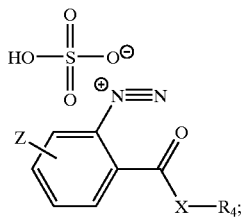

(c) preparing a second solution comprising (1) a second solvent mixture comprising water and an organic solvent soluble in or miscible in water, (2) either (A) a pyridone of the formula

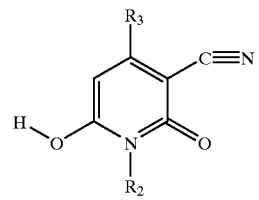

or (B) a dipyridone of the formula

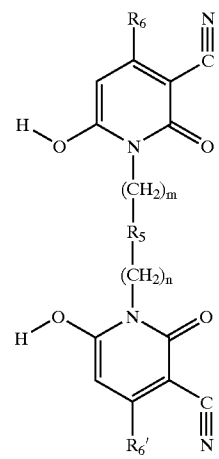

(3) a base present in an amount of at least about 3 molar equivalents of base per mole of pyridone moiety, and (4) an optional buffer salt, and (d) combining either (A) the second solution containing the dianiline and the first solution containing the pyridone, or (B) the second solution containing the aniline and the first solution containing the dipyridone to form a third solution and effect a coupling reaction to form a diazopyridone compound either (A) of the formula

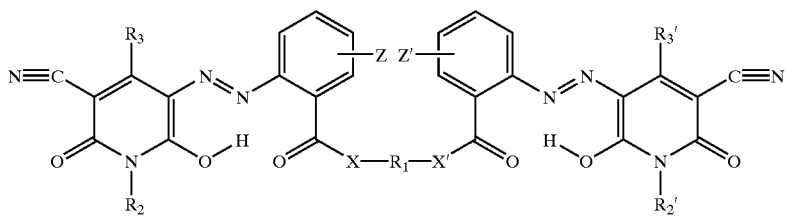

or (B) of the formula

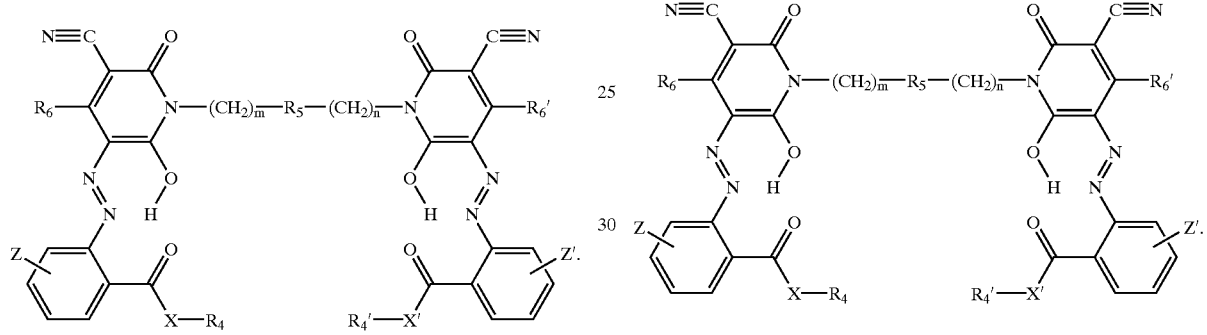

Copending application U.S. Ser. No. 10/186,023, filed concurrently herewith, entitled "Dimeric Azo Pyridone Colorants," with the named inventors Rina Carlini, James M. Duff, Jeffery H. Banning, Bo Wu, and James D. Mayo, the disclosure of which is totally incorporated herein by reference, discloses compounds of the formula

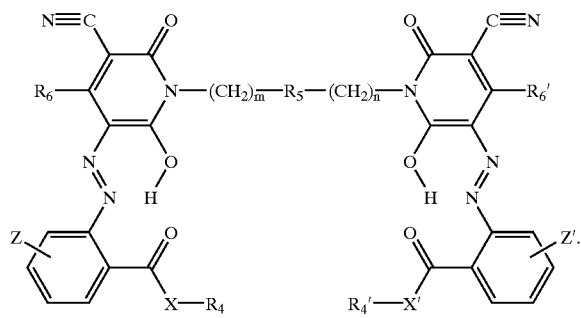

The compounds are useful as colorants, particularly in applications such as phase change inks. Copending application U.S. Ser. No. 10/184,266, filed concurrently herewith, entitled "Phase Change Inks Containing Dimeric Azo Pyridone Colorants," with the named inventors Bo Wu, Rina Carlini, James M. Duff, Jeffery H. Banning, and James D. Mayo, the disclosure of which is totally incorporated herein by reference, discloses a phase change ink composition comprising a phase change ink carrier and a colorant compound of the formula

BACKGROUND OF THE INVENTION

The present invention is directed to a process for preparing pyridone compounds. More specifically, the present invention is directed to a process for preparing pyridone compounds containing hydrocarbon substituents. One embodiment of the present invention is directed to a process for preparing substituted pyridone compounds which comprises (a) admixing in the absence of a solvent (1) an amine of the formula $R_1$—$NH_2$ wherein $R_1$ is an alkyl group, an aryl group, an arylalkyl group, or an alkylaryl group, and (2) a first ester of the formula

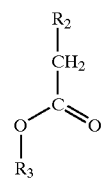

wherein $R_2$ is an electron withdrawing group and $R_3$ is an alkyl group; (b) heating the mixture containing the amine and the first ester to form an intermediate compound of the formula

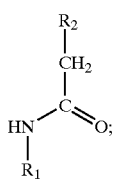

(c) admixing the intermediate compound with (1) a base and (2) a second ester of the formula

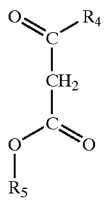

wherein $R_4$ is an alkyl group, an aryl group, an arylalkyl group, or an alkylaryl group and $R_5$ is an alkyl group, said second ester being present in a molar excess relative to the intermediate compound, said base being present in a molar excess relative to the intermediate compound, and (d) heating the mixture containing the intermediate compound, the second ester, and the base to form a pyridone compound of the formula

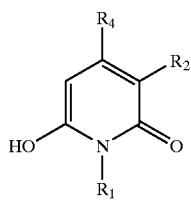

or a salt thereof. Another embodiment of the present invention is directed to a process for preparing diazopyridone compounds which comprises (a) admixing in the absence of a solvent (1) an amine of the formula $R_1$—$NH_2$ wherein $R_1$ is an alkyl group, an aryl group, an arylalkyl group, or an alkylaryl group, and (2) a first ester of the formula

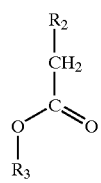

wherein $R_2$ is an electron withdrawing group and $R_3$ is an alkyl group; (b) heating the mixture containing the amine and the first ester to form an intermediate compound of the formula

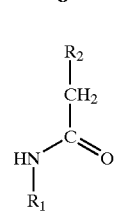

(c) admixing the intermediate compound with (1) a base and (2) a second ester of the formula

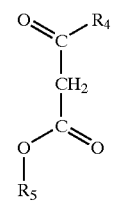

wherein $R_4$ is an alkyl group, an aryl group, an arylalkyl group, or an alkylaryl group and $R_5$ is an alkyl group, said second ester being present in a molar excess relative to the intermediate compound, said base being present in a molar excess relative to the intermediate compound, (d) heating the mixture containing the intermediate compound, the second ester, and the base to form a pyridone compound of the formula

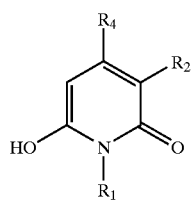

or a salt thereof; and (e) reacting the pyridone compound with a diazonium salt of the formula

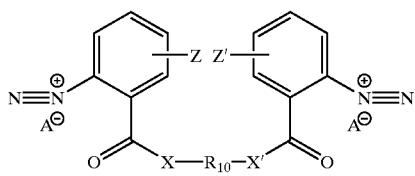

wherein $R_{10}$ is (i) an alkylene group, (ii) an arylene group, (iii) an arylalkylene group, (iv) an alkylarylene group, (v) an alkyleneoxy group, (vi) an aryleneoxy group, (vii) an arylalkyleneoxy group, (viii) an alkylaryleneoxy group, (ix) a polyalkyleneoxy group, (x) a polyaryleneoxy group, (xi) a polyarylalkyleneoxy group, (xii) a polyalkylaryleneoxy group, (xiii) a heterocyclic group, (xiv) a silylene group, (xv) a siloxane group, (xvi) a polysilylene group, or (xvii) a polysiloxane group, X and X' each, independently of the other, is (i) a direct bond, (ii) an oxygen atom, (iii) a sulfur atom, (iv) a group of the formula —$NR_{40}$— wherein $R_{40}$ is a hydrogen atom, an alkyl group, an aryl group, an arylalkyl group, or an alkylaryl group, or (v) a group of the formula —$CR_{50}R_{60}$— wherein $R_{50}$ and $R_{60}$ each, independently of the other, is a hydrogen atom, an alkyl group, an aryl group, an arylalkyl group, or an alkylaryl group, Z and Z' each, independently of the other, is (i) a hydrogen atom, (ii) a halogen atom, (iii) a nitro group, (iv) an alkyl group, (v) an aryl group, (vi) an arylalkyl group, (vii) an alkylaryl group, (viii) a group of the formula

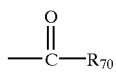

wherein $R_{70}$ is an alkyl group, an aryl group, an arylalkyl group, an alkylaryl group, an alkoxy group, an aryloxy group, an arylalkyloxy group, an alkylaryloxy group, a polyalkyleneoxy group, a polyaryleneoxy group, a polyarylalkyleneoxy group, a polyalkylaryleneoxy group, a heterocyclic group, a silyl group, a siloxane group, a polysilylene group, or a polysiloxane group, (ix) a sulfonyl group of the formula —$SO_2R_{80}$ wherein $R_{80}$ is a hydrogen atom, an alkyl group, an aryl group, an arylalkyl group, an alkylaryl group, an alkoxy group, an aryloxy group, an arylalkyloxy group, an alkylaryloxy group, a polyalkyleneoxy group, a polyaryleneoxy group, a polyarylalkyleneoxy group, a polyalkylaryleneoxy group, a heterocyclic group, a silyl group, a siloxane group, a polysilylene group, or a polysiloxane group, or (x) a phosphoryl group of the formula —$PO_3R_{90}$ wherein $R_{90}$ is a hydrogen atom, an alkyl group, an aryl group, an arylalkyl group, an alkylaryl group, an alkoxy group, an aryloxy group, an arylalkyloxy group, an alkylaryloxy group, a polyalkyleneoxy group, a polyaryleneoxy group, a polyarylalkyleneoxy group, a polyalkylaryleneoxy group, a heterocyclic group, a silyl group, a siloxane group, a polysilylene group, or a polysiloxane group, and A is an anion to form a diazopyridone colorant of the formula

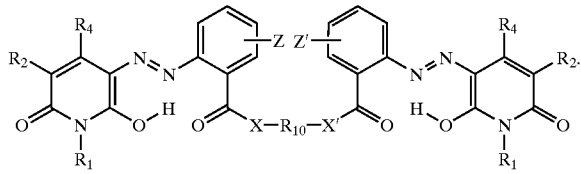

Methods for the preparation of substituted pyridones are known. These methods, however, when used to attempt to prepare pyridones substituted with relatively large hydrocarbon groups, exhibit disadvantages such as low yields, long reaction times, and difficulty in isolating the product.

"Investigation of the Reaction Conditions for the Synthesis of 4,6-Disubstituted-3-cyano-2-pyridones and 4-Methyl-3-cyano-6-hydroxy-2-pyridone," D. Z. Mijin et al., *J. Serb. Chem. Soc.*, Vol. 59, No. 12, p. 959 (1994), the disclosure of which is totally incorporated herein by reference, discloses an investigation of the reaction conditions for the synthesis of substituted 3-cyano-2-pyridones from cyannoacetamide and 1,3-diketones and 4-methyl-3-cyano-6-hydroxy-2-pyridone from cyanoacetamide and ethyl acetoacetate. Different catalysts and solvents were used, including phase transfer catalysts at different concentrations and temperatures. Very good yields and purity of the crude products were achieved when NaOH and hexane were used. Most of the phase transfer catalysts used gave poor results, but a certain catalytic effect was observed.

"Synthesis of Isoquinoline Alkaloids. II. The Synthesis and Reactions of 4-Methyl-3-pyridinecarboxaldehyde and Other 4-Methyl-3-substituted Pyridines, J. M. Bobbitt et al., *J. Org. Chem.*, Vol 25, p. 560 (1960), the disclosure of which is totally incorporated herein by reference, discloses the synthesis of 4-methyl-3-pyridinecarboxaldehyde by an unequivocal route. The syntheses of several new 4-methyl-3-substituted pyridines were carried out and the methods for the preparation of others was improved.

"Synthesis and Dyeing Characteristics of 5-(4-Arylazophenyl)azo-3-cyano-4-methyl-6-hydroxy-2-pyridones," J. M. Kanhere et al., *Indian Journal of Textile Research*, Vol. 13, p. 213 (1988), the disclosure of which is totally incorporated herein by reference, discloses the preparation of fourteen bisazo disperse dyes, 5-(4-arylazophenyl)azo-3-cyano-4-methyl-6-hydroxy-2-pyridones, and their dyeing performance on polyester was assessed. The dyeings on polyester had yellow, orange, brown, and red shades with good pickup, good to excellent lightfastness, and excellent sublimation fastness.

"Synthesis of Some Pyridone Azo Dyes from 1-Substituted 2-Hydroxy-6-pyridone Derivatives and their Colour Assessment," C. Chen et al., *Dyes and Pigments*, Vol. 15, p. 69 (1991), the disclosure of which is totally incorporated herein by reference, discloses the synthesis of a series of 3-(p-substituted phenylazo)-6-pyridone dyes which were suitable for the dyeing of polyester fabrics. Characterization of the dyes was carried out by spectral and elemental analysis. The color parameters of the dyed fabrics were measured. The assessment of color was made in terms of CIE tristimulus values. The Helmholtz coordinates and the position of color in CIELAB coordinates were reported. The correlation between color and structure of the dyes was discussed.

"Synthesis of 3-Cyano-6-hydroxy-5-(2-(perfluoroalkyl) phenylazo)-2-pyridones and their Application for Dye Diffusion Thermal Transfer Printing," M. Matsui et al., *Bull. Chem. Soc. Jpn.*, 1993, Vol. 66, Iss. 6, pp. 1790–4, the disclosure of which is totally incorporated herein by reference, discloses the synthesis of new fluorine-containing azopyridone dyes, 3-cyano-6-hydroxy-5-[2-(perfluoroalkyl) phenylazo]-2-pyridones. Though the introduction of a long perfluoroalkyl group lowered film forming ability and sensitivity, 5-[2-[(trifluoromethyl)phenylazo]- and 5-[2-perfluorobutyl)phenylazo]-3-cyano-4-methyl-6-hydroxy-2-pyridones showed good photostability.

European Patent Publication 1 125990 A1 and PCT Patent Publication WO 01/09256 A1, the disclosures of each of which are totally incorporated herein by reference, discloses an aqueous ink for ink jet recording which contains at least a water-insoluble coloring matter, water, and a resin as main components and which takes the form of an emulsion, which is characterized by containing at least one yellow hue coloring matter selected from the group consisting of a quinophthalone compound represented by the formula (1)

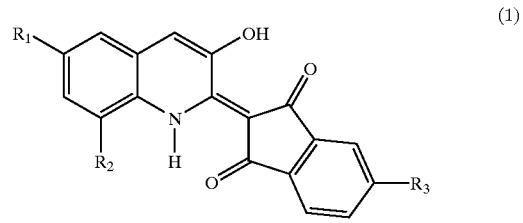

(1)

wherein each of $R_1$ to $R_3$ independently represents a hydrogen atom, an unsubstituted or substituted alkyl group, —$CONR_4R_5$, or —$COOR_6$ (in which each of $R_4$ to $R_6$ independently represents a hydrogen atom, an unsubstituted or substituted alkyl group, or an unsubstituted or substituted aryl group) and all of $R_1$ to $R_3$ are not a hydrogen atom at the same time, and a pyridone azo compound represented by the formula (2)

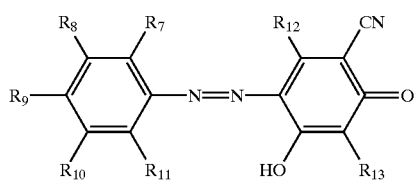
(2)

wherein each of $R_7$ to $R_{11}$ independently represents a hydrogen atom, a halogen atom, an unsubstituted or substituted alkyl group, an aralkyl group, an unsubstituted or substituted alkoxy group, an unsubstituted or substituted aryl group, an unsubstituted or substituted aryloxy group, a hydroxyl group, —$NR_{14}R_{15}$ (in which $R_{14}$ and $R_{15}$ independently represent a hydrogen atom, an unsubstituted or substituted alkyl group, or an aralkyl group), —$COX_1$ (in which $X_1$ represents an unsubstituted or substituted alkoxy group, an unsubstituted or substituted aryloxy group, or —$NR_{16}R_{17}$ (in which each of $R_{16}$ and $R_{17}$ independently represent a hydrogen atom, an unsubstituted or substituted alkyl group, an aralkyl group, or an unsubstituted or substituted aryl group)), —$COO(CH_2)_n$—$COX_2$, —$OCOX_3$, or —$NHCOX_4$ (in which each of $X_2$ to $X_4$ independently represents an unsubstituted or substituted alkyl group, an aralkyl group, an unsubstituted or substituted aryl group, an unsubstituted or substituted alkoxy group, or an unsubstituted or substituted aryloxy group, and n is an integer of 1 to 3), $R_{12}$ represents an unsubstituted or substituted alkyl group, and $R_{13}$ represents an unsubstituted or substituted alkyl group, an aralkyl group, or an unsubstituted or substituted aryl group. The ink is for ink jet recording having excellent light resistance and storage stability, and enables formation of a high quality image without blotting, and the obtained recording image is excellent in water resistance.

PCT Patent Publication WO 01/21714, the disclosure of which is totally incorporated herein by reference, discloses compositions comprising a solvent and at least one compound of the formula

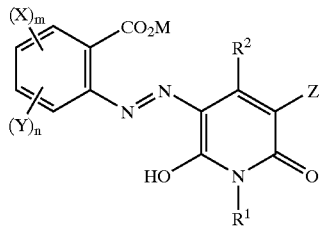

in which $R^1$ represents H, an optionally substituted $C_{1-8}$ carbyl derived group, or a group of the formula

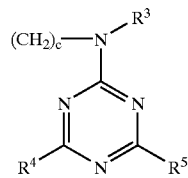

where C is from 2 to 6, $R^3$ represents optionally substituted $C_{1-8}$ carbyl derived group, $R^4$ and $R^5$ independently represent an optional substituent, $R^2$ represents an optionally substituted $C_{1-8}$ carbyl derived group, X Y, and Z independently represent H or an optional substituent, M represents H or a cation, and m and n independently represent 0, 1, or 2. Also disclosed are compounds of the above formula providing that at least one of $R^1$, $R^2$, X, Y, or Z comprises a group of formula $SO_3M$ or $PO_3M_2$. These compositions and compounds are useful as the colorants to prepare color filters for displays.

U.S. Pat. No. 4,247,456 (von Brachel et al.), the disclosure of which is totally incorporated herein by reference, discloses water-insoluble monoazo dyes of the formula

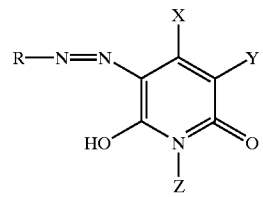

wherein R is the residue of a benzene, naphthalene, diphenyl, diphenylmethane, or heterocyclic diazo compound which is free from water solubilizing groups, produced by reacting a diazotized amine of the benzene, naphthalene, diphenyl, diphenylmethane, or heterocyclic series which is free from water solubilizing groups with the appropriate 6-hydroxy-2-pyridone and the utility thereof for the dyeing and printing of synthetic fabric materials to yellow to red shades having excellent fastness to light and sublimation.

U.S. Pat. No. 3,957,749 (von Brachel et al.), the disclosure of which is totally incorporated herein by reference, discloses water-insoluble monoazo dyes of the formula

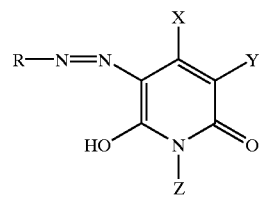

produced by reacting a diazotized amine of the benzene, naphthalene, diphenyl, diphenylmethane, or heterocyclic series which is free from water solubilizing groups with the appropriate 6-hydroxy-2-pyridone and the utility thereof for the dyeing and printing of synthetic fabric materials to yellow to red shades having excellent fastness to light and sublimation.

Japanese Patent Publication JP 05331382, the disclosure of which is totally incorporated herein by reference, discloses a specific pyridone azo pigment which is bright yellow and highly soluble in a solvent, absorbs light of long wavelength, and is useful for a thermal transfer sheet. The pyridone azo pigment is represented by the formula

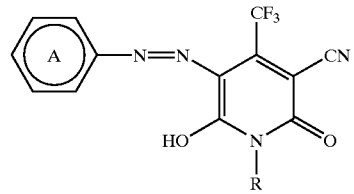

wherein R is H, alkyl, substituted alkyl, cycloalkyl, aryl, or optionally substituted phenyl, and ring A is a benzene ring optionally having a nonionic group. The pigment is prepared by diazotizing an aniline compound and coupling the resulting diazo compound with a pyridone compound. Having a good solubility in an organic solvent and a good dispersibility in water, the pigment facilitates the preparation of an ink containing a high concentration of the pigment homogeneously dissolved or dispersed. The prepared ink enables the preparation of a thermal transfer sheet coated with the ink uniformly in a high density.

British Patent 1,559,001 (Harvey et al.), the disclosure of which is totally incorporated herein by reference, discloses a hydrophilic textile material colored with a dyestuff of the formula

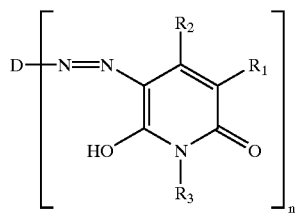

wherein D is the residue of a diazo or tetrazo component; $R_1$ is a hydrogen atom or an alkyl, chloro, acetamido, benzamido, carbamoyl, or an N-substituted carbamyl, for example —CONHBr, group or, preferably, a cyano group; $R_2$ is an alkyl group, especially methyl, optionally substituted with a chlorine atom, a phenyl group, optionally substituted with an alkyl or alkoxy group, or a carboxylic acid or carboxylic acid ester group; or $R_1$ and $R_2$ together with the carbon atoms in the 3- or 4-position of the pyridone ring may form an alicyclic or aromatic ring system so that, for example, $R_1$ and $R_2$ together may be a tri- or tetra-methylene group forming with the pyridone of penteno [c] or hexeno [c] pyrid-2-one, or $R_1$ and $R_2$ may form together with the adjacent carbon atoms of the pyridone ring a benzene ring giving a benz [c] pyrid-2one; $R_3$ is an aryl group carrying one or more substituents selected from —NO, —$SO_2R^1$, —$COR^1$, —$COOR^1$, —CF, or —CN, wherein $R^1$ is an optionally substituted alkyl or aryl group; and n is an integer which may be 1 or 2.

German Patent Publication DE 19646430, the disclosure of which is totally incorporated herein by reference, discloses dye mixtures comprising at least two structurally different dyes, each corresponding to formula

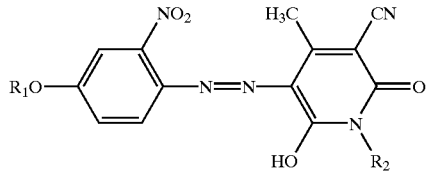

wherein $R_1$ is $C_1$–$C_4$ alkyl; $R_2$ is the $(CH_2)_nO$—$R_5$ radical; $R_5$ is, independently of $R_1$, $C_1$–$C_4$ alkyl or phenyl (which is unsubstituted or substituted by $C_1$–$C_4$ alkyl, $C_1$–$C_4$ alkoxy, hydroxy, or halogen); and n is 2 or 3, which dye mixtures are suitable for dyeing or printing textile fibre materials (e.g. polyester materials), giving dyeings having good around fastness properties.

German Patent Publication DE 19646429, the disclosure of which is totally incorporated herein by reference, discloses dye mixtures comprising at least two structurally different dyes, each of which has the formula

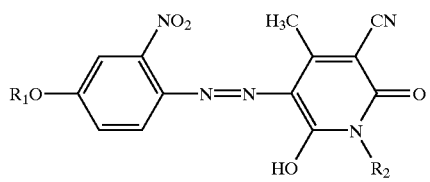

in which $R_1$ is $C_1$–$C_4$ alkyl and $R_2$ is isopropyl, n-butyl, isobutyl, sec-butyl, or tert-butyl; or $C_1$–$C_3$ alkyl which is substituted by phenyl or phenoxy; or $R_1$ is phenyl (which is unsubstituted or substituted by $C_1$–$C_4$ alkyl, $C_1$–$C_4$ alkoxy, hydroxyl, or halogen), $C_1$–$C_4$ alkoxy-$C_1$–$C_3$ alkylene, phenoxy-$C_1$–$C_3$ alkylene, or $C_1$–$C_3$ alkyl which is substituted by phenyl (which is unsubstituted or substituted by $C_1$–$C_4$ alkyl, $C_1$–$C_4$ alkoxy, hydroxyl, or halogen) and $R_2$ is $C_1$–$C_{10}$ alkyl (which is unsubstituted or substituted by hydroxyl, $OCOR_3$, or phenoxy, where the phenyl ring in phenoxy is unsubstituted or substituted by $C_1$–$C_4$ alkyl, $C_1$–$C_4$ alkoxy, hydroxyl, or halogen) and the alkyl chain in $C_1$–$C_{10}$ alkyl from $C_2$ can be interrupted by one or more oxygen atoms; phenyl (which is unsubstituted or substituted by $C_1$–$C_4$ alkyl, $C_1$–$C_4$ alkoxy, hydroxyl, or halogen); or $C_5$–$C_7$ cycloalkyl; and $R_3$ is $C_1$–$C_4$ alkyl, are suitable for dyeing or printing textile fibre materials (e.g. polyester materials) and give dyeings with good allround properties.

German Patent Publication DE 19647869, the disclosure of which is totally incorporated herein by reference, discloses a dye mixture containing at least 2 dyes with different structures, each of formula

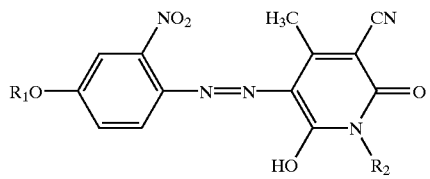

where $R_1$ is a 1–4C alkyl; and $R_2$ is a linear 1–3C alkyl. Also claimed is hydrophobic fibre material, preferably polyester textile material, dyed or printed with the mixture.

PCT Patent Publication WO 99/43754, the disclosure of which is totally incorporated herein by reference, discloses compounds of the formula

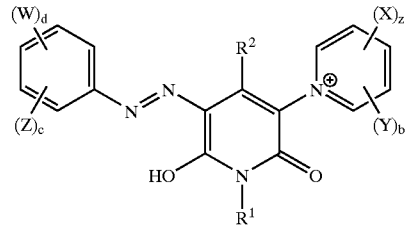

and salts and tautomers thereof, wherein: $R_1$ and $R_2$ each independently is H, optionally substituted alkyl, optionally substituted aryl, or optionally substituted arylalkyl; each W and each X independently is —COOH, —$SO_3H$, —$PO_3H_2$, or alkyl substituted by one or more groups selected from —COOH, —$SO_3H$, and —$PO_3H_2$; each Y and each Z independently is a substituent other than those defined for W and X; a and d each independently is 1 to 5; b and c each independently is 0 to 4; (a+b) has a value of 5 or less; and (c+d) has a value of 5 or less. Also claimed are inks containing a compound of this formula, an ink jet printing process using the inks, substrates printed with the inks, and ink jet printer cartridges containing the inks.

U.S. Pat. No. 5,929,218 (Lee et al.), the disclosure of which is totally incorporated herein by reference, discloses pyridone-based yellow monoazo dyes used in thermal transfer having following formula which have good stability and hue

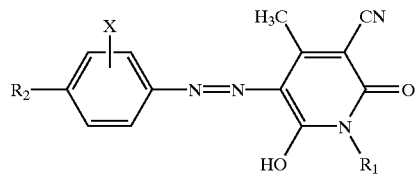

wherein $R_1$ is hydrogen atom; unsubstituted or substituted alkyl group of from 1 to 8 carbon atoms with alkoxy or aryl; or unsubstituted or substituted aryl group with alkoxy or halogen, and X is hydrogen atom; alkyl group of from 1 to 4 carbon atoms; alkoxy group; or halogen, $R_2$ is selected from the following groups;

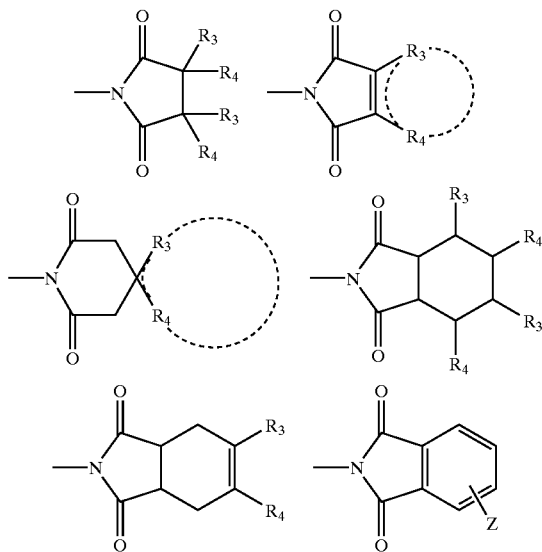

wherein $R_3$ and $R_4$ are independently selected from groups consisting hydrogen, substituted or unsubstituted alkyl group of from 1 to 4 carbon atoms, halogen, alkyl carboxylate, and carbonyl group; $R_3$—$R_4$ is noncyclization with $R_3$ and $R_4$ and selected respectively from the above substituents ($R_3$ and $R_4$); or saturated or unsaturated cycloalkyl of from 3 to 6 carbon atoms, Z is nitro, halogen, alkyl group of from 1 to 4 carbon atoms, alkoxy, sulfonyl, carbonyl, carboxyamide, sulfonamino, cyano, hydroxy, or hydrogen atom.

European Patent Publication EP 0 706 679 B1, U.S. Pat. No. 5,853,929 (Campbell), and PCT Patent Publication WO 95/00885, the disclosures of each of which are totally incorporated herein by reference, disclose colored cyan toner for electroreprography and laser printing based on Solvent Blue 70, and a trichomatic set of coloured toners based on Solvent Blue 70, benzodifuranone red dyes, and azo pyridone yellow dyes of the formula

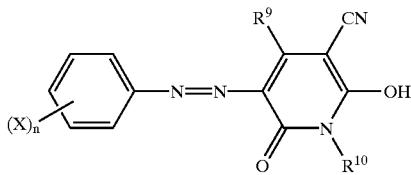

wherein X is halogen, nitro, or a group —$COOR^5$, $R^9$ is $C_{1-4}$ alkyl, $R^{10}$ is $C_{1-12}$ alkyl, $R^5$ is $C_{1-8}$ alkyl or a group of formula —$(C_{1-3}\text{-alkylene})\text{-}(CO)_q$—Z wherein q is 0 or 1 and Z is —$OR^6$ or —$NR^6R^7$ when q=1 or Z is —$OR^8$ when q=0, $R^6$ is selected from optionally substituted $C_{1-8}$ alkyl, optionally substituted $C_{1-8}$ alkoxy-$C_{1-8}$ alkyl, and a second group represented by $R^5$ in which $R^6$ is optionally substituted $C_{1-8}$ alkyl or optionally substituted $C_{1-8}$ alkoxy-$C_{1-8}$ alkyl, $R^7$ is selected from H and optionally substituted $C_{1-8}$ alkyl, and $R^8$ is selected from optionally substituted $C_{1-8}$ alkyl, optionally substituted $C_{1-8}$ alkoxy-$C_{1-8}$ alkyl, optionally substituted $C_{1-8}$ alkyl sulfonyl or carbonyl, and optionally substituted phenyl sulfonyl or carbamoyl.

European Patent Publication EP 0 247 737, the disclosure of which is totally incorporated herein by reference, discloses a thermal transfer printing sheet suitable for use in a thermal transfer printing process, especially for the conversion of a digital image into a visible print, comprising a substrate having a coating comprising a dye of the formula

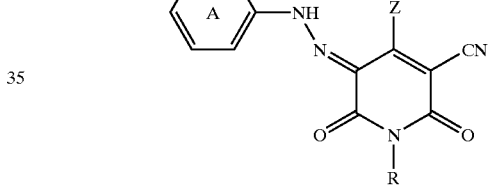

wherein Ring A is unsubstituted or carries, in the 2- or 4-position with respect to the azo link, at least one group selected from —$CX_3$, $X^1$, CN, $NO_2$, —OCO.Y, —CO.Y, —CO.H, —$OS_2$.Y, and —$SO_2$.Y, provided that A is substituted when Z is $CH_3$ and R is $C_{2-4}$-alkyl; X and $X^1$ are each independently halogen; Y is selected from $R^1$, —$OR^1$, $SR^1$, and —$NR^1R^2$; $R^1$ is selected from $C_{1-12}$-alkyl, $C_{1-12}$-alkyl interrupted by one or two groups selected from —O—, —CO—, O.CO—, and —CO.O—, $C_{3-7}$-cycloalkyl, mono- or bi-cyclic aryl, and $C_{1-3}$-alkylene attached to an adjacent carbon atom on Ring A; $R^2$ is selected from H, $C_{1-12}$-alkyl, $C_{3-7}$-cycloalkyl, and mono- or bi-cyclic aryl; Z is $C_{1-12}$-alkyl or phenyl; and R is selected from $C_{2-12}$-alkyl unbranched in the alpha-position, $C_{2-12}$-alkyl unbranched in alpha-position and interrupted by one or two groups selected from —O—, —CO—, O.CO—, and —CO.O—, phenyl, $C_{1-4}$-alkylphenyl, biphenyl, and biphenyl interrupted by a group selected from —O—, —CO—, O.CO—, and —CO.O—, each of which is free from hydrogen atoms capable of intermolecular hydrogen bonding.

U.S. Pat. No. 5,041,413 (Evans et al.), the disclosure of which is totally incorporated herein by reference, discloses a yellow dye-donor element for thermal dye transfer comprises a support having thereon a dye layer comprising a mixture of yellow dyes dispersed in a polymeric binder, at least one of the yellow dyes having the formula

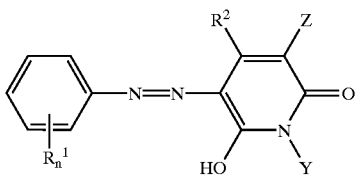

wherein: each $R_1$ independently represents a substituted or unsubstituted alkyl group of from 1 to about 10 carbon atoms, a cycloalkyl group of from about 5 to about 7 carbon atoms; a substituted or unsubstituted allyl group; an aryl group of from about 6 to about 10 carbon atoms; a hetaryl group of from 5 to 10 atoms; acyl; arylsulfonyl; aminocarbonyl; aminosulfonyl; fluorosulfonyl; halogen; nitro; alkylthio; or arylthio; or any two adjacent $R_1$'s together represent the atoms necessary to form a 5- or 6-membered fused ring; n represents an integer from 0–4; $R_2$ represents hydrogen; a substituted or unsubstituted alkyl, cycloalkyl, allyl, aryl or hetaryl group as described above for $R^1$; cyano; acyl; alkylsulfonyl; arylsulfonyl; or alkoxycarbonyl; Z represents cyano; alkoxycarbonyl; acyl; nitro; arylsulfonyl or alkylsulfonyl; Y represents hydrogen; a substituted or unsubstituted alkyl, cycloalkyl, allyl, aryl or hetaryl group as described above for $R^1$; amino; alkylamino; arylamino; acylamino; or sulfonylamino; and at least one of the other of the dyes having the formula

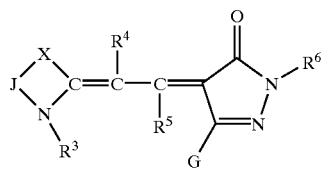

wherein $R^3$ represents the same groups as $R^1$ above; $R^4$ and $R^5$ each independently represents hydrogen, $R^3$; cyano; acyloxy; alkoxy of 1 to about 6 carbon atoms; halogen; or alkoxycarbonyl; or any two of $R^3$, $R^4$ and $R^5$ together represent the atoms necessary to complete a 5- to 7-membered ring; $R^6$ represents the same groups as $R^3$; G represents a substituted or unsubstituted alkyl, cycloalkyl or allyl group as described above for $R^3$, $NR^7R^8$ or $OR^9$; $R^7$ and $R^8$ each independently represents hydrogen, acyl or $R^3$, with the proviso that $R^7$ and $R^8$ cannot both be hydrogen at the same time; or $R^7$ and $R^8$ together represent the atoms necessary to complete a 5- to 7-membered ring; $R^9$ represents the same groups as $R^3$; X represents $C(R^{10})(R^{11})$, S, O or $NR^{10}$; $R^{10}$ and $R^{11}$ each independently represents the same groups as $R^3$; or $R^{10}$ and $R^{11}$ together represent the atoms necessary to complete a 5- to 7-membered ring; and J represents the atoms necessary to complete a 5- or 6-membered ring which may be fused to another ring system.

U.S. Pat. No. 4,359,418 (Lienhard et al.), the disclosure of which is totally incorporated herein by reference, discloses azo dyestuff sulfonic acid salts of the formula

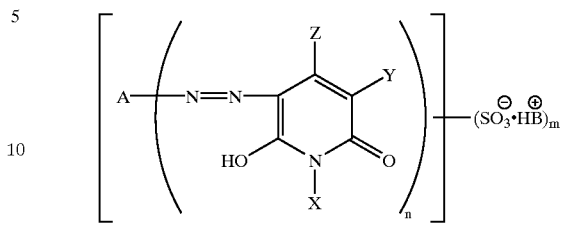

wherein A represents a carbocyclic or heterocyclic aromatic radical, B represents an aliphatic, cycloaliphatic or araliphatic amine, X represents a hydrogen atom or a substituted or unsubstituted alkyl group, a cycloalkyl, aralkyl or aryl group, Y represents a hydrogen or halogen atom, a nitro, cyano, acyl, sulfonic acid, arylsulfonyl, alkoxycarbonyl group or a substituted or unsubstituted alkyl, sulfamoyl or carbamoyl group, Z represents a substituted or unsubstituted alkyl group or an aryl radical, m and n are 1 or 2; said dyestuffs salts having good solubility in organic solvents and functioning to color solutions of film forming polymers in yellow to orange shades.

German Patent Publication DE 3538517 and U.S. Pat. No. 5,037,964 (Moser et al.), the disclosures of each of which are totally incorporated herein by reference, disclose sulfonic acid group-free basic azo compounds, which correspond in one of the possible tautomeric forms to the formula

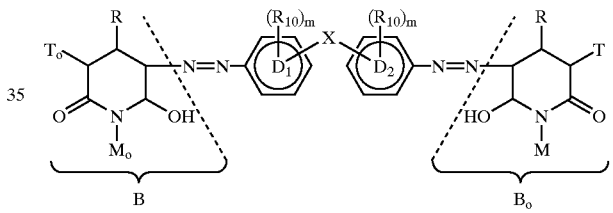

their preparation and their use for dyeing paper.

Japanese Patent Publication JP 03192158, the disclosure of which is totally incorporated herein by reference, discloses obtaining a, yellow dye exhibiting high dyeing speed and degree of exhaustion in dyeing a textile material, leather, pulp, paper, etc., as well as excellent brightness and fastness to water by selecting a compound wherein a pyridopyridinium salt is linked to diphenylfluorene through azo groups. A cationic compound of the formula

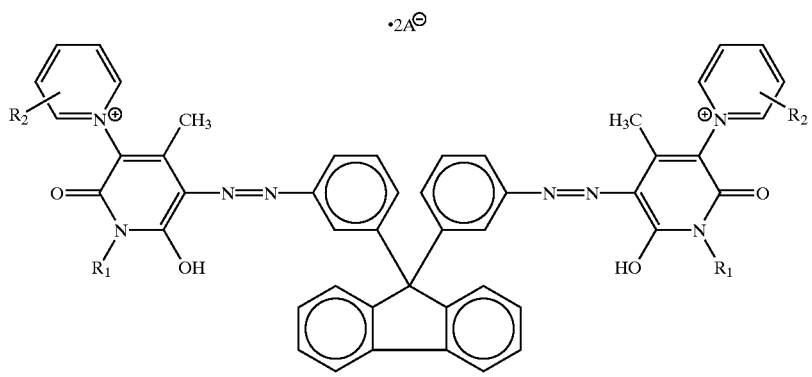

wherein $R_1$ is H or 1–4C alkyl; $R_2$ is H, 1–4C alkyl, or alkoxy; and $A^-$ is an anion which has a structure wherein a tetrazo compound, of 9,9'-bis(4-anilino)fluorene is coupled with a pyridone derivative is selected as a yellow dye, which is useful for dyeing an unsized pulp or paper (e.g. a napkin, table cloth, or sanitary paper). The dyeing with the dye is carried out at a pH of 4–8, preferably 5–7, and at 10–50° C., preferably 15–30° C.

British Patent Publication GB 2 008 606, the disclosure of which is totally incorporated herein by reference, discloses water-insoluble yellow monoazo dyes suitable for dyeing hydrophobic synthetic fibres, particularly polyesters, having the formula

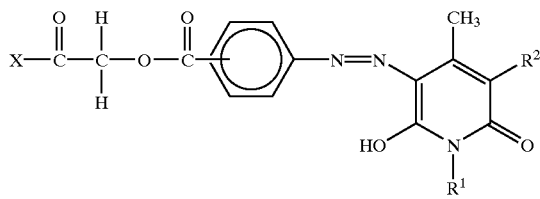

in which X represents $OR^3$ or $NHR^3$, $NR^3R^4$ ($R^3$, $R^4$ together optionally forming with N a ring having 5 to 6 carbon atoms, $NHR^5$; $R^1$ represents a hydrogen atom, an alkyl having 1 to 5 carbon atoms, $(CH_2)_2OH$ or $(CH_2)_3OR^3$; $R^2$ represents CN, $COOR^3$, $CONHR^3$, $CONR^3R^4$ ($R^3$, $R^4$ together optionally forming with N a ring having 5 to 6 carbon atoms); $R^3$ and $R^4$ represent alkyl groups having 1 to 5 carbon atoms; and $R_5$ represents a cycloalkyl having 5 or 6 carbon atoms. The dyes may be prepared by the reaction of

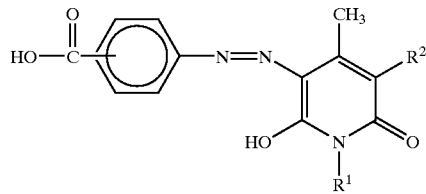

with Hal—$CH_2CO$—X in which Hal represents Cl or Br.

Preparation and Evaluation of Yellow Pigments Based on H-Pyridone and Esters of Aminoterephthalic Acid," P. Slosar et al., CHEMagazin, Vol. 9, No. 6, pp. 8–11 (1999), the disclosure of which is totally incorporated herein by reference, discloses yellow pigments based on H-pyridone and esters of aminoterepholic acid wherein the color strength, brilliance (purity), and deepening of greenish shade were the larger the smaller alkyl is in the carbalkoxy group in o-position towards the azo group and the greater alkyl is in the carbalkoxy group in m-position towards the azo group.

Of potential background interest with respect to the present invention are the following references: U.S. Pat. No. 5,919,839; U.S. Pat. No. 5,827,918; U.S. Pat. No. 4,889,560; U.S. Pat. No. 5,372,852; "Synthesis, Morphology, and Optical Properties of Tetrahedral Oligo(phenylenevinylene) Materials," S. Wang et al., J. Am. Chem. Soc., Vol. 120, p. 5695 (2000); "Syntheses of Amphiphilic Diblock Copolymers Containing a Conjugated Block and Their Self-Assembling Properties," H. Wang et al., J. Am. Chem. Soc., Vol. 122, p. 6855 (2000); "Crystal Engineering of Conjugated Oligomers and the Spectral Signature of π Stacking in Conjugated Oligomers and Polymers," A. Koren et al., Chem. Mater., Vol. 12, p. 1519 (2000); "The Chemistry of Isatoic Anhydride," G. M. Coppola, Synthesis, p. 505 (1980); "Isatoic Anhydride. IV. Reactions with Various Nucleophiles," R. P. Staiger et al., J. Org. Chem., Vol. 24, p. 1214 (1959); German Patent Publication DE3543360; Japanese Patent Publication JP 2001214083; German Patent Publication DE 3505899; Indian Patent Publication 147527; European Patent Publication EP 0 524 637; European Patent Publication EP 0 529 282; European Patent Publication EP 0 083 553; Japanese Patent Publication JP 2000 62327; Japanese Patent Publication JP 85152563; "Synthesis of 3-Cyano-6-hydroxy-5-(2-(perfluoroalkyl)phenylazo)-2-pyridones and their Application for Dye Diffusion Thermal Transfer Printing," Bull Chem. Soc. Jpn., 1993, Vol. 66, Iss. 6, Pp.1790–4; European Patent Publication 0 844 287; European Patent Publication 0 404 493; U.S. Pat. No. 5,902,841; U.S. Pat. No. 5,621,022; U.S. Pat. No. 5,006,170; Chinese Patent Publication CN 1115773; German Patent Publication DE 3447117; Japanese Patent Publication JP 5331382; Japanese Patent Publication JP 63210169; Japanese Patent Publication JP 63199764; Japanese Patent Publication JP 63199763; Japanese Patent Publication JP 63199762; Japanese Patent Publication JP 63199761; Japanese Patent Publication JP 63199760; Japanese Patent Publication JP 63071392; Japanese Patent Publication JP 61181865; Japanese Patent Publication JP 61036366; Japanese Patent Publication JP 60152563; Japanese Patent Publication JP 60112862; Japanese Patent Publication JP 60112861; Japanese Patent Publication JP 58149953; Japanese Patent Publication JP 56092961; Japanese Patent Publication JP 56026957; Japanese Patent Publication JP 55099958; Japanese Patent Publication JP 96 11443 (JP8011443); Japanese Patent Publication JP 93169849 (JP5169849); Japanese Patent Publication JP 93 51536 (JP5051536); Japanese Patent Publication JP 90185569 (JP2185569); European Patent Publication 0 319 234; European Patent Publication 0 314 002; European Patent Publication 0 302 401; U.S. Pat. No. 4,734,349; Japanese Patent Publication JP 87290762 (JP62290762); Japanese Patent Publication JP 86244595 (JP61244595); Indian Patent Publication IN 147868; Spanish Patent Publication 475254 (Equivalent of Italian Patent Publication IT 1088895); German Patent Publication DE 2727809; "Colour and Constitution of Azo Dyes Derived from 2-Thioalkyl-4,6-Diaminopyrimidines and 3-Cyano-1,4-dimethyl-6-hydroxy-2-pyridone as Coupling Components," L. Cheng et al., Dyes and Pigments, Vol. 7, No. 5, pp. 373–388 (1986); European Patent Publication 1 168 046; U.S. Pat. No. 4,644,058; Japanese Patent Publication JP 63039380; Japanese Patent Publication JP 54102328; Japanese Patent Publication JP 54070337; "Trends in Modern Dye Chemistry. Part 10," N. R. Ayyangar and K. V. Srinivasan, Colourage, Vol. 37, No. 2, pp. 29–30 (Jan. 16, 1990); European Patent Publication EP 0 172 283; Japanese Patent Publication JP 05169854; Japanese Patent Publication JP 04292988; Japanese Patent Publication JP 63161060; Japanese Patent Publication JP 61244595; Korean Patent Publication KR 119563; European Patent Publication EP 0 142 863; European Patent Publication EP 0 023 770; Japanese Patent Publication JP 00239549 (JP2000239549); Japanese Patent Publication JP 11269402; Japanese Patent Publication JP 09041267; Japanese Patent Publication JP 08039941; U.S. Pat. No. 4,994,564; Japanese Patent Publication JP 06294909; Japanese Patent Publication JP 06122829; Japanese Patent Publication JP 05255602; Japanese Patent Publication JP 05051536; Japanese Patent Publication JP 04235093; European Patent Publication EP 0 468 647; European Patent Publication EP 0 063 275; U.S. Pat. No. 4,216,145; and German Patent Publication DE 2606506; the disclosures of each of which are totally incorporated herein by reference.

While known compositions and processes are suitable for their intended purposes, a need remains for improved methods for preparing substituted pyridone compounds. In addition, a need remains for methods for preparing substituted pyridone compounds containing relatively large hydrocarbon moieties. Further, a need remains for methods for preparing substituted pyridone compounds containing relatively large hydrocarbon moieties that enable desirably high product yields. Additionally, a need remains for methods for preparing substituted pyridone compounds containing relatively large hydrocarbon moieties that enable desirably short reaction times. There is also a need for methods for preparing substituted pyridone compounds containing relatively large hydrocarbon moieties that enable reasonably simple recovery of the generated pyridone product. In addition, there is a need for methods for preparing substituted pyridone compounds containing relatively large hydrocarbon moieties that are cost-effective. Further, there is a need for methods for preparing substituted pyridone compounds containing relatively large hydrocarbon moieties that can be employed on both large scale and small scale quantities of reactants. Additionally, there is a need for methods for preparing substituted pyridone compounds containing relatively large hydrocarbon moieties that enable reasonably simple recovery of a high yield in high purity of the generated pyridone product without the need for post-synthetic treatments such as recrystallization, distillation, or column chromatography.

SUMMARY OF THE INVENTION

The present invention is directed to a process for preparing substituted pyridone compounds which comprises (a) admixing in the absence of a solvent (1) an amine of the formula $R_1$—$NH_2$ wherein $R_1$ is an alkyl group, an aryl group, an arylalkyl group, or an alkylaryl group, and (2) a first ester of the formula

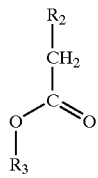

wherein $R_2$ is an electron withdrawing group and $R_3$ is an alkyl group; (b) heating the mixture containing the amine and the first ester to form an intermediate compound of the formula

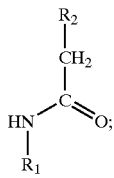

(c) admixing the intermediate compound with (1) a base and (2) a second ester of the formula

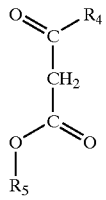

wherein $R_4$ is an alkyl group, an aryl group, an arylalkyl group, or an alkylaryl group and $R_5$ is an alkyl group, said second ester being present in a molar excess relative to the intermediate compound, said base being present in a molar excess relative to the intermediate compound, and (d) heating the mixture containing the intermediate compound, the second ester, and the base to form a pyridone compound of the formula

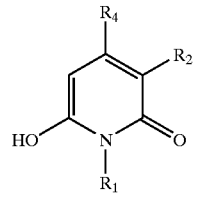

or a salt thereof. Another embodiment of the present invention is directed to a process for preparing diazopyridone compounds which comprises (a) admixing in the absence of a solvent (1) an amine of the formula $R_1$—$NH_2$ wherein $R_1$ is an alkyl group, an aryl group, an arylalkyl group, or an alkylaryl group, and (2) a first ester of the formula

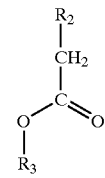

wherein $R_2$ is an electron withdrawing group and $R_3$ is an alkyl group; (b) heating the mixture containing the amine and the first ester to form an intermediate compound of the formula

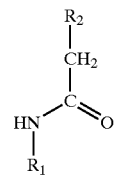

(c) admixing the intermediate compound with (1) a base and (2) a second ester of the formula

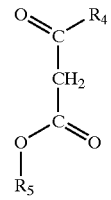

wherein $R_4$ is an alkyl group, an aryl group, an arylalkyl group, or an alkylaryl group and $R_5$ is an alkyl group, said second ester being present in a molar excess relative to the intermediate compound, said base being present in a molar excess relative to the intermediate compound, (d) heating the mixture containing the intermediate compound, the second ester, and the base to form a pyridone compound of the formula

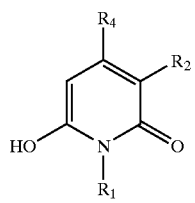

or a salt thereof; and (e) reacting the pyridone compound with a diazonium salt of the formula

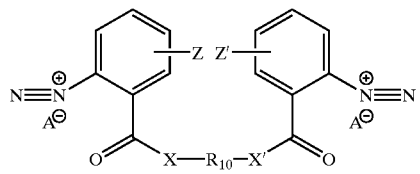

wherein $R_{10}$ is (i) an alkylene group, (ii) an arylene group, (iii) an arylalkylene group, (iv) an alkylarylene group, (v) an alkyleneoxy group, (vi) an aryleneoxy group, (vii) an arylalkyleneoxy group, (viii) an alkylaryleneoxy group, (ix) a polyalkyleneoxy group, (x) a polyaryleneoxy group, (xi) a polyarylalkyleneoxy group, (xii) a polyalkylaryleneoxy group, (xiii) a heterocyclic group, (xiv) a silylene group, (xv) a siloxane group, (xvi) a polysilylene group, or (xvii) a polysiloxane group, X and X' each, independently of the other, is (i) a direct bond, (ii) an oxygen atom, (iii) a sulfur atom, (iv) a group of the formula —$NR_{40}$— wherein $R_{40}$ is a hydrogen atom, an alkyl group, an aryl group, an arylalkyl group, or an alkylaryl group, or (v) a group of the formula —$CR_{50}R_{60}$— wherein $R_{50}$ and $R_{60}$ each, independently of the other, is a hydrogen atom, an alkyl group, an aryl group, an arylalkyl group, or an alkylaryl group, Z and Z' each, independently of the other, is (i) a hydrogen atom, (ii) a halogen atom, (iii) a nitro group, (iv) an alkyl group, (v) an aryl group, (vi) an arylalkyl group, (vii) an alkylaryl group, (viii) a group of the formula

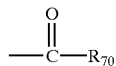

wherein $R_{70}$ is an alkyl group, an aryl group, an arylalkyl group, an alkylaryl group, an alkoxy group, an aryloxy group, an arylalkyloxy group, an alkylaryloxy group, a polyalkyleneoxy group, a polyaryleneoxy group, a polyarylalkyleneoxy group, a polyolkylaryleneoxy group, a heterocyclic group, a silyl group, a siloxane group, a polysilylene group, or a polysiloxane group, (ix) a sulfonyl group of the formula —$SO_2R_{80}$ wherein $R_{80}$ is a hydrogen atom, an alkyl group, an aryl group, an arylalkyl group, an alkylaryl group, an alkoxy group, an aryloxy group, an arylalkyloxy group, an alkylaryloxy group, a polyalkyleneoxy group, a polyaryleneoxy group, a polyarylalkyleneoxy group, a polyalkylaryleneoxy group, a heterocyclic group, a silyl group, a siloxane group, a polysilylene group, or a polysiloxane group, or (x) a phosphoryl group of the formula —$PO_3R_{90}$ wherein $R_{90}$ is a hydrogen atom, an alkyl group, an aryl group, an arylalkyl group, an alkylaryl group, an alkoxy group, an aryloxy group, an arylalkyloxy group, an alkylaryloxy group, a polyalkyleneoxy group, a polyaryleneoxy group, a polyarylalkyleneoxy group, a polyalkylaryleneoxy group, a heterocyclic group, a silyl group, a siloxane group, a polysilylene group, or a polysiloxane group, and A is an anion to form a diazopyridone colorant of the formula

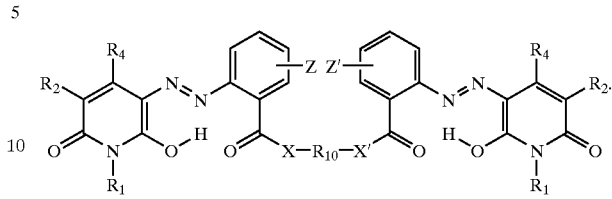

DETAILED DESCRIPTION OF THE INVENTION

Substituted pyridone compounds are prepared according to the present invention by first preparing a corresponding intermediate compound, as follows:

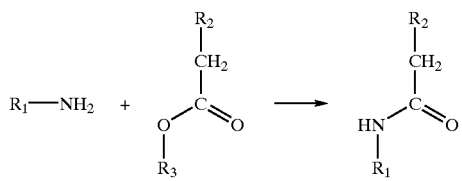

wherein $R_1$ is an alkyl group (including linear, branched, saturated, unsaturated, cyclic, unsubstituted, and substituted alkyl groups, and wherein hetero atoms, such as oxygen, nitrogen, sulfur, silicon, phosphorus, and the like can be present in the alkyl group), in one embodiment with at least about 1 carbon atom, in another embodiment with at least about 8 carbon atoms, in yet another embodiment with at least about 10 carbon atoms, in still another embodiment with at least about 12 carbon atoms, in another embodiment with at least about 14 carbon atoms, in yet another embodiment with at least about 16 carbon atoms, in still another embodiment with at least about 18 carbon atoms, in another embodiment with at least about 20 carbon atoms, and in yet another embodiment with at least about 22 carbon atoms, and in one embodiment with no more than about 100 carbon atoms, in another embodiment with no more than about 50 carbon atoms, and in yet another embodiment with no more than about 24 carbon atoms, although the number of carbon atoms can be outside of these ranges, an aryl group (including unsubstituted and substituted aryl groups), in one embodiment with at least about 6 carbon atoms, in another embodiment with at least about 10 carbon atoms, in yet another embodiment with at least about 13 carbon atoms, in still another embodiment with at least about 14 carbon atoms, in another embodiment with at least about 16 carbon atoms, in yet another embodiment with at least about 17 carbon atoms, in still another embodiment with at least about 18 carbon atoms, in another embodiment with at least about 19 carbon atoms, in yet another embodiment with at least about 20 carbon atoms, in still another embodiment with at least about 21 carbon atoms, in another embodiment with at least about 22 carbon atoms, and in yet another embodiment with at least about 23 carbon atoms, and in one embodiment with no more than about 100 carbon atoms, in another embodiment with no more than about 50 carbon atoms, and in yet another embodiment with no more than about 24 carbon atoms, although the number of carbon atoms can be outside of these ranges, an arylalkyl group (including unsubstituted and substituted arylalkyl groups), in one embodiment with at least about 7 carbon atoms, in another embodiment with at least about 8 carbon atoms, in another embodiment with at least about 10 carbon atoms, in yet another embodiment with at least about 12 carbon atoms, in still another embodiment with at least about 14 carbon atoms, in another embodiment with at least about 16 carbon atoms, in yet another embodiment with at least about 18 carbon atoms, in still another embodiment with at least about 20 carbon atoms, and in another embodiment with at least about 22 carbon atoms, and in one embodiment with no more than about 100 carbon atoms, in another embodiment with no more than about 50 carbon atoms, and in yet another embodiment with no more than about 24 carbon atoms, although the number of carbon atoms can be outside of these ranges, or an alkylaryl group (including unsubstituted and substituted alkylaryl groups), in one embodiment with at least about 7 carbon atoms, in another embodiment with at least about 8 carbon atoms, in another embodiment with at least about 10 carbon atoms, in yet another embodiment with at least about 12 carbon atoms, in still another embodiment with at least about 14 carbon atoms, in another embodiment with at least about 16 carbon atoms, in yet another embodiment with at least about 18 carbon atoms, in still another embodiment with at least about 20 carbon atoms, and in another embodiment with at least about 22 carbon atoms, and in one embodiment with no more than about 100 carbon atoms, in another embodiment with no more than about 50 carbon atoms, and in yet another embodiment with no more than about 24 carbon atoms, although the number of carbon atoms can be outside of these ranges, wherein the substituents on the substituted alkyl, aryl, arylalkyl, and alkylaryl groups can be (but are not limited to) hydroxy groups, halogen atoms, amine groups, imine groups, ammonium groups, pyridine groups, pyridinium groups, ether groups, aldehyde groups, ester groups, amide groups, carbonyl groups, thiocarbonyl groups, sulfate groups, sulfonate groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, cyanato groups, isocyanato groups, thiocyanato groups, isothiocyanato groups, mixtures thereof, and the like, wherein two or more substituents can be joined together to form a ring.

Some specific examples of suitable $R_1$ groups include (but are not limited to) ethyl, of the formula —$CH_2CH_3$, n-butyl, of the formula —$(CH_2)_3CH_3$, n-octyl, of the formula —$(CH_2)_7CH_3$, n-decyl, of the formula —$(CH_2)_9CH_3$, n-dodecyl, of the formula —$(CH_2)_{11}CH_3$, n-tetradecyl, of the formula —$(CH_2)_{13}CH_3$, cetyl, of the formula —$(CH_2)_{15}CH_3$, stearyl, of the formula —$(CH_2)_{17}CH_3$, 2-ethylhexyl, of the formula

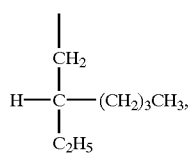

abietyl, including groups of the formula

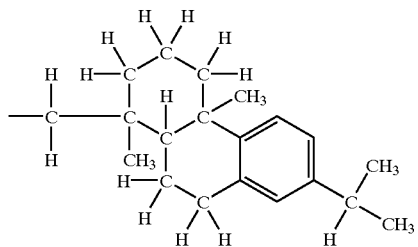

as well as hydrogenated and dehydrogenated isomers of the above formula that are also derivatives of the rosin-derived natural product abietic acid, such as didehydroabietyl and the like, 3-propyl octadecanoyl, of the formula

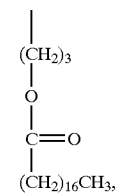

2,2-dimethyl-1,3-dioxolane-4-methylene, of the formula

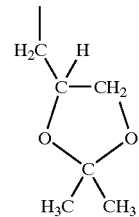

n-hexanediyl, of the formula —$(CH_2)_6$—, n-octanediyl, of the formula —$(CH_2)_8$—, n-deconediyl, of the formula —$(CH_2)_{10}$—, n-dodecanediyl, of the formula —$(CH_2)_{12}$—, 2-methyl-1,5-pentanediyl, of the formula

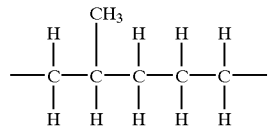

butane-1,4-di(oxypropyl), of the formula —$CH_2CH_2CH_2$—O—$CH_2CH_2CH_2CH_2$—O—$CH_2CH_2CH_2$—, 1,3-cyclohexanedimethylene, of the formula (which is not intended to be limited to any particular stereochemistry and includes all cis and trans isomers)

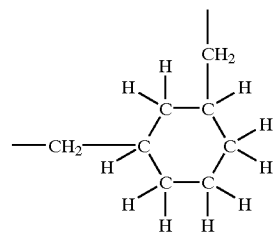

dicyclohexylmethane-4,4'-diyl, of the formula (which is not intended to be limited to any particular stereochemistry and includes all cis and trans isomers)

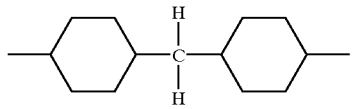

4,8-bis(methylene)tricyclo[5210$^{2,6}$]decanediyl, of the formula (which is not intended to be limited to any particular stereochemistry and includes all cis and trans isomers)

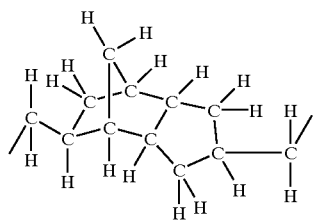

a branched alkylene group having 36 carbon atoms, including isomers of the formula

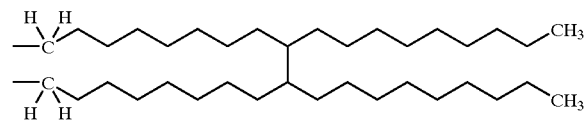

and other branched isomers (which may include unsaturations and cyclic groups), a branched alkylene diester group having 36 carbon atoms, including isomers of the formula

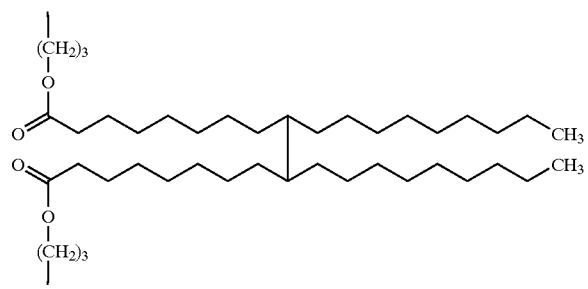

and other branched isomers (which may include unsaturations and cyclic groups), and the like.

Examples of suitable amines include monoamines, such as octyl amine, of the formula $CH_3(CH_2)_7NH_2$, decyl amine, of the formula $CH_3(CH_2)_9NH_2$, dodecyl amine, of the formula $CH_3(CH_2)_{11}NH_2$, tetradecyl amine, of the formula $CH_3(CH_2)_{13}NH_2$, hexadecyl amine, of the formula $CH_3(CH_2)_{15}NH_2$, octadecyl amine, of the formula $CH_3(CH_2)_{17}NH_2$, abietyl amine, an arylalkylamine of the formula

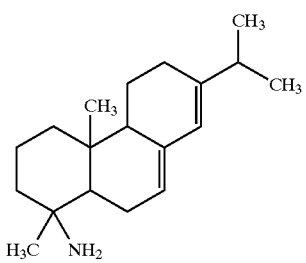

as well as hydrogenated and dehydrogenated isomers of the above formula that are also derivatives of the rosin-derived natural product abietic acid, such as didehydroabietyl amine and the like, diamines, which can be used as precursors to form dipyridones of the formula

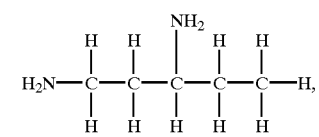

(wherein $R_2'$ is defined as is $R_2$ but wherein $R_2'$ can be different from $R_2$, and wherein $R_4'$ is defined as is $R_4$ but wherein $R_4'$ can be different from $R_4$) such as those of the general formula $H_2N-R_1-NH_2$ wherein $R_1$ is defined as above except that it is divalent instead of monovalent (i.e., an alkylene, arylene, arylalkylene, or alkylarylene group), including 1,3-diaminopentane, of the formula

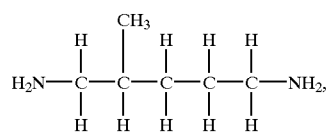

1,6-diaminohexane, of the formula $H_2N-(CH_2)_6-NH_2$, 2-methyl-1,5-diaminopentane, of the formula

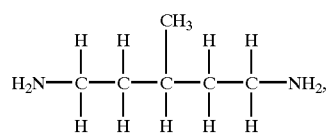

3-methyl-1,5-diaminopentane, of the formula 1,8-diaminooctane, of the formula $H_2N-(CH_2)_8-NH_2$, 1,10-diaminodecane, of the formula $H_2N-(CH_2)_{10}NH_2$, 1,12-diaminododecane, of the formula $H_2N-(CH_2)_{12}-NH_2$, 4,7-dioxadecan-1,10-diyl diamine, of the formula $H_2N-(CH_2)_3-O-(CH_2)_2-O-(CH_2)_3-NH_2$, 4,9-dioxadodecan-1,12-diyl diamine, of the formula $H_2N-(CH_2)_3-O-(CH_2)_4-O-(CH_2)_3-NH_2$, 1,4-cyclohexyldimethylene diamine, of the formula (which is not intended to be limited to any particular stereochemistry and includes all cis and trans isomers)

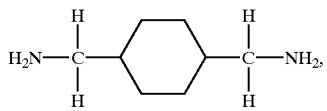

1,3-cyclohexyldimethylene diamine, of the formula (which is not intended to be limited to any particular stereochemistry and includes all cis and trans isomers)

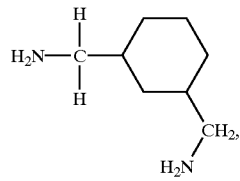

bicyclohexan-4,4'-diyl diamine, of the formula (which is not intended to be limited to any particular stereochemistry and includes all cis and trans isomers)

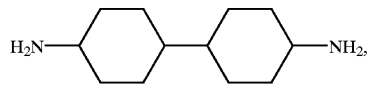

dicyclohexylmethane-4,4'-diyl diamine, of the formula (which is not intended to be limited to any particular stereochemistry and includes all cis and trans isomers)

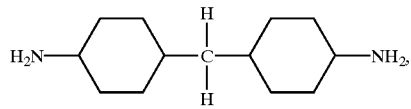

isopropylidenedicyclohexan-4,4'-diyl diamine, of the formula (which is not intended to be limited to any particular stereochemistry and includes all cis and trans isomers)

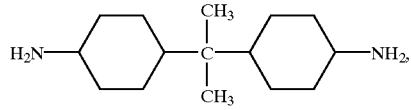

and the like, triamines, which can be used as precursors to form tripyridones of the formula

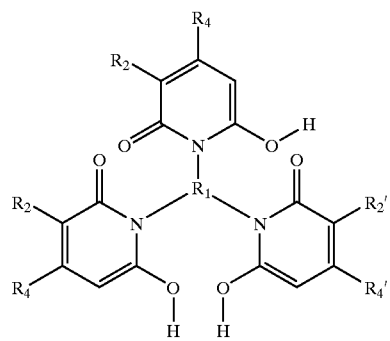

(wherein $R_2'$ and $R_2''$ are defined as is $R_2$ but wherein $R_2'$ and $R_2''$ can be different from $R_2$ and from each other, and wherein $R_4'$ and $R_4''$ are defined as is $R_4$ but wherein $R_4'$ and $R_4''$ con be different from $R_4$ and from each other) such as those of the general formula $R_1(NH_2)_3$ wherein $R_1$ is defined as above except that it is trivalent instead of monovalent (i.e., an alkylene, arylene, arylalkylene, or alkylarylene group), including those of the general formula

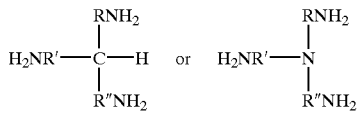

wherein R, R', and R" each, independently of the others, is an alkylene group (including linear, branched, saturated, unsaturated, cyclic, unsubstituted, and substituted alkylene groups, and wherein hetero atoms, such as oxygen, nitrogen, sulfur, silicon, phosphorus, and the like can be present in the alkylene group), typically with from 1 to about 100 carbon atoms, preferably with from about 3 to about 50 carbon atoms, and more preferably with from about 12 to about 40 carbon atoms, although the number of carbon atoms can be outside of these ranges, an arylene group (including unsubstituted and substituted arylene groups), typically with from about 6 to about 100 carbon atoms, preferably with from about 8 to about 50 carbon atoms, and more preferably with from about 12 to about 40 carbon atoms, although the number of carbon atoms can be outside of these ranges, an arylalkylene group (including unsubstituted and substituted arylalkylene groups), typically with from about 7 to about 100 carbon atoms, preferably with from about 8 to about 50 carbon atoms, and more preferably with from about 12 to about 40 carbon atoms, although the number of carbon atoms can be outside of these ranges, or an alkylarylene group (including unsubstituted and substituted alkylarylene groups), typically with from about 7 to about 100 carbon atoms, preferably with from about 8 to about 50 carbon atoms, and more preferably with from about 12 to about 40 carbon atoms, although the number of carbon atoms can be outside of these ranges, wherein the substituents on the substituted alkylene, arylene, arylalkylene, and alkylarylene groups can be (but are not limited to) hydroxy groups, halogen atoms, amine groups, imine groups, ammonium groups, pyridine groups, pyridinium groups, ether groups, aldehyde groups, ester groups, amide groups, carbonyl groups, thiocarbonyl groups, sulfate groups, sulfonate groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, cyanato groups, isocyanato groups, thiocyanato groups, isothiocyanato groups, mixtures thereof, and the like, wherein two or more substituents can be joined together to form a ring, with specific examples of triamines including tris(2-aminoethyl) amine, of the formula

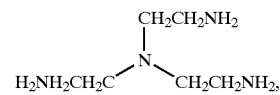

3-methyleneoctane-1,8-diyl triamine, of the formula

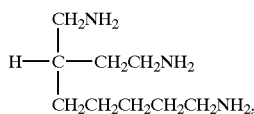

and the like, as well as mixtures thereof.

The intermediate compound is formed by reacting the corresponding amine with a first ester of the formula

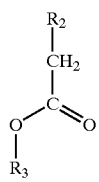

wherein $R_2$ is an electron withdrawing group, including (but not limited to) a cyanato group, of the formula NCO—, an isocyanato group, of the formula OCN—, an isocyano group, of the formula CN—, a cyano group, of the formula NC—, a thiocyanato group, of the formula NCS—, an isothiocyanato group, of the formula SCN—, a halide atom, such as Cl, Br, I, and the like, a group of the formula

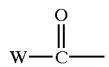

wherein W is a hydrogen atom, an alkyl group (including linear, branched, saturated, unsaturated, cyclic, unsubstituted, and substituted alkyl groups, and wherein hetero atoms, such as oxygen, nitrogen, sulfur, silicon, phosphorus, and the like can be present in the alkyl group), typically with from 1 to about 100 carbon atoms, preferably with from about 1 to about 10 carbon atoms, and more preferably with from about 1 to about 5 carbon atoms, although the number of carbon atoms can be outside of these ranges, an aryl group (including unsubstituted and substituted aryl groups, and wherein hetero atoms, such as oxygen, nitrogen, sulfur, and the like can be present in the aryl group), typically with from 6 to about 100 carbon atoms, and preferably with from about 6 to about 10 carbon atoms, although the number of carbon atoms can be outside of these ranges, an arylalkyl group (including unsubstituted and substituted arylalkyl groups, and wherein hetero atoms, such as oxygen, nitrogen, sulfur, and the like can be present in either or both of the aryl portion and the alkyl portion of the arylalkyl group), typically with from 7 to about 100 carbon atoms, and preferably with from about 7 to about 10 carbon atoms, although the number of carbon atoms can be outside of these ranges, or an alkylaryl group (including unsubstituted and substituted alkylaryl groups, and wherein hetero atoms, such as oxygen, nitrogen, sulfur, and the like can be present in either or both of the aryl portion and the alkyl portion of the alkylaryl group), typically with from 7 to about 100 carbon atoms, and preferably with from about 7 to about 10 carbon atoms, although the number of carbon atoms can be outside of these ranges, and the like, wherein the substituents on the substituted alkyl, aryl, arylalkyl, and alkylaryl groups can be (but are not limited to) hydroxy groups, halogen atoms, amine groups, imine groups, ammonium groups, pyridine groups, pyridinium groups, ether groups, aldehyde groups, ester groups, amide groups, carbonyl groups, thiocarbonyl groups, sulfate groups, sulfonate groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, cyanato groups, isocyanato groups, thiocyanato groups, isothiocyanato groups, mixtures thereof, and the like, wherein two or more substituents can be joined together to form a ring, and $R_3$ is an alkyl group (including linear, branched, saturated, unsaturated, cyclic, unsubstituted, and substituted alkyl groups, and wherein hetero atoms, such as oxygen, nitrogen, sulfur, silicon, phosphorus, and the like can be present in the alkyl group), typically with from 1 to about 5 carbon atoms, although the number of carbon atoms can be outside of this range, such as methyl, ethyl, n-propyl, isopropyl, n-butyl, sec-butyl, t-butyl, pentyl, 1-methyl butyl, 2-methyl butyl, 3-methyl butyl, 2,2-dimethyl propyl, 1,3-dimethyl propyl, and the like. Examples of suitable first ester compounds of this formula include methyl cyanoacetate, ethyl cyanoacetate, n-propyl cyanoacetate, isopropyl cyanoacetate, n-butyl cyanoacetate, tert-butyl cyanoacetote, and the like, as well as mixtures thereof. This reaction takes place in the absence of any solvent. In one embodiment, the reaction mixture to form this intermediate consists essentially of the amine of the formula $R_1$—$NH_2$ and the first ester of the formula

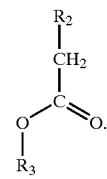

In another embodiment, the reaction mixture to form this intermediate consists of the amine of the formula $R_1$—$NH_2$ and the first ester of the formula

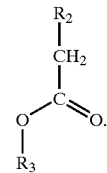

The amine of the formula $R_1$—$NH_2$ and the first ester are present in any desired or effective relative amounts, in one embodiment at least about 0.75 moles of amine per every one mole of first ester, in another embodiment at least about 0.9 mole of amine per every one mole of first ester, and in yet another embodiment at least about 0.95 mole of amine per every one mole of first ester, and in one embodiment no more than about 1.25 moles of amine per every one mole of first ester, in another embodiment no more than about 1.1 moles of amine per every one mole of first ester, and in yet another embodiment no more than about 1.0 mole of amine per every one mole of first ester, although the relative amounts of reactants can be outside of these ranges. When a diamine is used, the number of amine groups per molecule is doubled, so the above numbers are divided by 2 in that instance; when a triamine is used, the number of amine groups per molecule is trebled, so the above numbers are divided by 3 in that instance.

The mixture of the amine and the first ester is heated to any desired or effective temperature to effect the conversion to the intermediate compound, in one embodiment to a temperature of at least about 80° C., in another embodiment to a temperature of at least about 100° C., and in yet another embodiment to a temperature of at least about 110° C., and is heated in one embodiment to a temperature of no more than about 160° C., in another embodiment to a temperature of no more than about 140° C., and in yet another embodiment of no more than about 120° C., although the temperature can be outside of these ranges.

The reaction between the amine and the first ester is carried out by heating for any desired or effective amount of time, in one embodiment for a period of at least about 10 minutes, in another embodiment for a period of at least about 30 minutes, and in yet another embodiment for a period of at least about 45 minutes, and in one embodiment for a period of no more than about 480 minutes, in another embodiment for a period of no more than about 240 minutes, and in yet another embodiment for a period of no more than about 120 minutes, although the reaction time can be outside of these ranges.

The intermediate compound thus formed is then reacted with a second ester and a base ("B") to form the desired pyridone or a salt thereof, as follows:

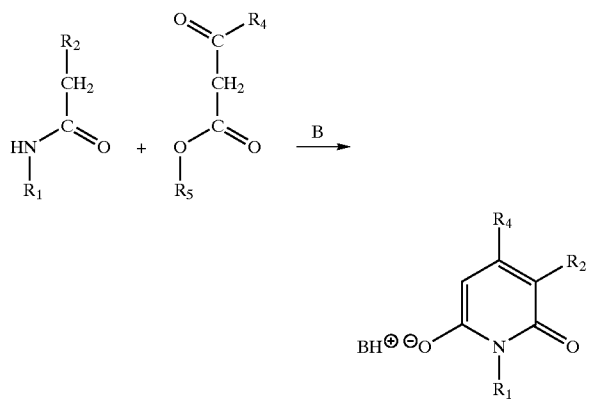

If a salt is formed, it can later be converted to the hydroxy compound by acidification, as follows:

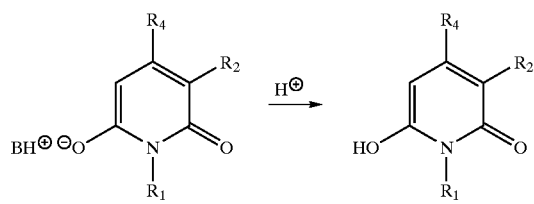

In the second ester, $R_4$ is an alkyl group (including linear, branched, saturated, unsaturated, cyclic, unsubstituted, and substituted alkyl groups, and wherein hetero atoms, such as oxygen, nitrogen, sulfur, silicon, phosphorus, and the like con be present in the alkyl group), typically with from 1 to about 100 carbon atoms, preferably with from about 1 to about 10 carbon atoms, and more preferably with from about 1 to about 5 carbon atoms, although the number of carbon atoms can be outside of these ranges, an aryl group (including unsubstituted and substituted aryl groups), typically with from about 6 to about 100 carbon atoms, and preferably with from about 6 to about 10 carbon atoms, although the number of carbon atoms can be outside of these ranges, an arylalkyl group (including unsubstituted and substituted arylalkyl groups), typically with from about 7 to about 100 carbon atoms, and preferably with from about 7 to about 10 carbon atoms, although the number of carbon atoms can be outside of these ranges, or an alkylaryl group (including unsubstituted and substituted alkylaryl groups), typically with from about 7 to about 100 carbon atoms, and preferably with from about 7 to about 10 carbon atoms, although the number of carbon atoms can be outside of these ranges, wherein the substituents on the substituted alkyl, aryl, arylalkyl, and alkylaryl groups can be (but are not limited to) hydroxy groups, halogen atoms, amine groups, imine groups, ammonium groups, pyridine groups, pyridinium groups, ether groups, aldehyde groups, ester groups, amide groups, carbonyl groups, thiocarbonyl groups, sulfate groups, sulfonate groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, cyanato groups, isocyanato groups, thiocyanato groups; isothiocyanato groups, mixtures thereof, and the like, wherein two or more substituents can be joined together to form a ring, and $R_5$ is an alkyl group (including linear, branched, saturated, unsaturated, cyclic, unsubstituted, and substituted alkyl groups, and wherein hetero atoms, such as oxygen, nitrogen, sulfur, silicon, phosphorus, and the like can be present in the alkyl group), typically with from 1 to about 5 carbon atoms, although the number of carbon atoms can be outside of this range, such as methyl, ethyl, n-propyl, isopropyl, n-butyl, sec-butyl, t-butyl, pentyl, 1-methyl butyl, 2-methyl butyl, 3-methyl butyl, 2,2-dimethyl propyl, 1,3-dimethyl propyl, and the like. Specific examples of second esters include methyl acetoacetate, ethyl acetoacetate, t-butyl acetoacetate, ethyl butyrylacetate, and the like, as well as mixtures thereof.

Examples of suitable $R_4$ groups methyl (—$CH_3$), linear alkyl groups of the formula —$(CH_2)_c CH_3$ wherein c is an integer of 1, 2, 3, 4, 5, 6, 7, 8, or 9, and the like.

Examples of suitable bases include piperidine, 1-methyl piperidine, 1-ethylpiperidine, piperazine, 1-ethylpiperazine, 2-ethylpiperazine, 1-methylpiperazine, 2-methylpiperazine, sodium hydroxide, triethylamine, tributylamine, dimethylethanolamine, diethylethanolamine, 1,4-diazabicyclo[2.2.2]octane, morpholine, 4-ethylmorpholine, t-octylamine, hexamethyl disilazane, tetramethyl ethylenediamine, diethylcyclohexylamine, di-isopropylethylamine, 4,4'-trimethylene-dipiperidine, 1,4-dimethyl-piperazine, benzimidazole, benzoxazole, dipiperidino-methane, tris-[2-(2-methoxyethoxy)-ethyl]amine, and the like, as well as mixtures thereof.

The intermediate compound of the formula

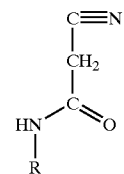

and the second ester are present in relative amounts such that the second ester is present in a molar excess, i.e., the molar ratio of second ester to intermediate is greater than 1:1. The relative amounts of second ester and intermediate are in one embodiment at least about 1.1 moles of second ester per every one mole of intermediate, in another embodiment at least about 1.2 moles of second ester per every one mole of intermediate, in yet another embodiment at least about 1.5 moles of second ester per every one mole of intermediate, and in still another embodiment at least about 2 moles of second ester per every one mole of intermediate, and in one embodiment no more than about 8 moles of second ester per every one mole of intermediate, in another embodiment no more than about 4 moles of second ester per every one mole of intermediate, and in yet another embodiment no more than about 2 moles of second ester per every one mole of intermediate, although the relative amounts of reactants can be outside of these ranges.

The intermediate compound of the formula

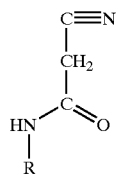

and the base are present in relative amounts such that the base is present in a molar excess, i.e., the molar ratio of base to intermediate is greater than 1:1. The relative amounts of base and intermediate are in one embodiment at least about 1.1 moles of base per every one mole of intermediate, in another embodiment at least about 1.2 moles of base per every one mole of intermediate, in yet another embodiment at least about 1.5 moles of base per every one mole of intermediate, and in still another embodiment at least about 2 moles of base per every one mole of intermediate, and in one embodiment no more than about 8 moles of base per every one mole of intermediate, in another embodiment no more than about 4 moles of base per every one mole of intermediate, and in yet another embodiment no more than about 2 moles of base per every one mole of intermediate, although the relative amounts of reactants can be outside of these ranges.

The reaction between the intermediate compound and the second ester can take place in the absence of a solvent, or, if desired for reasons such as lowering the viscosity of the product solution, ease of product recovery, or improved control of the reaction temperature, a solvent con be used. Any desired or suitable solvent can be used. Examples of suitable solvents include dimethyl formamide, N-methyl pyrrolidinone, toluene, sulfolane, and the like, as well as mixtures thereof.

When present, the solvent is present in any desired or effective amount, in one embodiment at least about 1 mole of intermediate of the formula

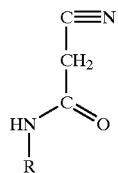

per liter of solvent, in another embodiment at least about 2 moles of intermediate per liter of solvent, and in yet another embodiment at least about 2.5 moles of intermediate per liter of solvent, and is present in an amount of in one embodiment no more than about 10 moles of intermediate per liter of solvent, in another embodiment no more than about 5 moles of intermediate per liter of solvent, and in yet another embodiment no more than about 3.5 moles of intermediate per liter of solvent, although the relative amount of solvent can be outside of these ranges.

The mixture of the intermediate, the base, and the second ester is heated to any desired or effective temperature to effect the conversion to the pyridone product, in one embodiment to a temperature of at least about 80° C., in another embodiment to a temperature of at least about 100° C., and in yet another embodiment to a temperature of at least about 110° C., and is heated in one embodiment to a temperature of no more than about 160° C., in another embodiment to a temperature of no more than about 140° C., and in yet another embodiment of no more than about 120° C., although the temperature can be outside of these ranges.

The reaction between the intermediate, the base, and the second ester is carried out by heating for any desired or effective amount of time, in one embodiment for a period of at least about 30 minutes, in another embodiment for a period of at least about 60 minutes, and in yet another embodiment for a period of at least about 120 minutes, and in one embodiment for a period of no more than about 1,440 minutes, in another embodiment for a period of no more than about 480 minutes, and in yet another embodiment for a period of no more than about 240 minutes, although the reaction time can be outside of these ranges.

Subsequent to completion of the reaction, the pyridone product can be recovered by cooling the reaction mixture to room temperature and pouring it into a non-solvent for the pyridone product. Examples of suitable non-solvents include water, methanol, ethanol, n-propanol, isopropanol, butanol, ethyl acetate, propyl acetate, butyl acetate, and the like, as well as mixtures thereof. For example, mixtures containing from 50 to 80 parts by volume methanol and from 20 to 50 parts by volume water, and more preferably containing from 60 to 80 parts by volume methanol and from 20 to 40 parts by volume water, were found to be particularly effective.

If desired, to convert any pyridone salt product to the hydroxy form, the non-solvent into which the reaction mixture is poured can be acidified. Any desired or suitable acid can be employed, such as hydrochloric acid, nitric acid, sulfuric acid, and the like, as well as mixtures thereof. In this instance, the acid is present in any desired or effective amount, in one embodiment at least about 1 mole of acid per mole of base used in the synthesis process (including any unreacted amine believed to be present from the reaction of the amine with the first ester), in another embodiment at least about 1.2 moles of acid per mole of base used in the synthesis process, and in yet another embodiment at least about 1.3 moles of acid per mole of base used in the synthesis process, and in one embodiment no more than about 3 moles of acid per mole of base used in the synthesis process, in another embodiment no more than about 2 moles of acid per mole of base used in the synthesis process, and in yet another embodiment no more than about 1.5 moles of acid per mole of base used in the synthesis process, although the amount of acid can be outside of these ranges.

The precipitated product can then be collected by any desired method, such as filtration or the like, washed, and dried. For washing, a mixture of 50 parts by weight methanol and 50 parts by weight water was found to be particularly effective.

The pyridone compounds prepared according to the present invention can be used as intermediates in the preparation of colorant molecules by reacting them with a diazonium salt of the formula

[Chemical structure diagram showing a bis-diazonium salt with two benzene rings each bearing a diazonium group (⊕N≡N with counterion A⊖), connected via carbonyl groups to X-R₁₀-X' linker, with Z substituents on the rings]

wherein A is any anion suitable for accompanying a diazonium salt, and wherein $R_{10}$ is (i) an alkylene group (including linear, branched, saturated, unsaturated, cyclic, unsubstituted, and substituted alkylene groups, and wherein hetero atoms, such as oxygen, nitrogen, sulfur, silicon, phosphorus, and the like either may or may not be present in the alkylene group), in one embodiment with at least 1 carbon atom, in another embodiment with at least about 8 carbon atoms, in yet another embodiment with at least about 10 carbon atoms, in still another embodiment with at least about 12 carbon atoms, in another embodiment with at least about 14 carbon atoms, in yet another embodiment with at least about 16 carbon atoms, in still another embodiment with at least about 18 carbon atoms, in another embodiment with at least about 20 carbon atoms, in yet another embodiment with at least about 22 carbon atoms, in still another embodiment with at least about 24 carbon atoms, in another embodiment with at least about 26 carbon atoms, in yet another embodiment with at least about 28 carbon atoms, in still another embodiment with at least about 30 carbon atoms, in another embodiment with at least about 32 carbon atoms, in yet another embodiment with at least about 34 carbon atoms, and in still another embodiment with a t least about 36 carbon atoms, and in one embodiment with no more than about 200 carbon atoms, in another embodiment with no more than about 100 carbon atoms, in yet another embodiment with no more than about 75 carbon atoms, in still another embodiment with no more than about 60 carbon atoms, in another embodiment with no more than about 50 carbon atoms, and in yet another embodiment with no more than about 40 carbon atoms, although the number of carbon atoms can be outside of these ranges, (ii) an arylene group (including unsubstituted and substituted arylene groups), in one embodiment with at least about 6 carbon atoms, in another embodiment with at least about 10 carbon atoms, in yet another embodiment with at least about 13 carbon atoms, in still another embodiment with at least about 14 carbon atoms, in another embodiment with at least about 16 carbon atoms, in yet another embodiment with at least about 17 carbon atoms, in still another embodiment with at least about 18 carbon atoms, in another embodiment with at least about 19 carbon atoms, in yet another embodiment with at least about 20 carbon atoms, in still another embodiment with at least about 21 carbon atoms, in another embodiment with at least about 22 carbon atoms, and in yet another embodiment with at least about 23 carbon atoms, and in one embodiment with no more than about 100 carbon atoms, in another embodiment with no more than about 75 carbon atoms, and in yet another embodiment with no more than about 50 carbon atoms, although the number of carbon atoms can be outside of these ranges, an (iii) arylalkylene group (including unsubstituted and substituted arylalkylene groups), in one embodiment with at least about 7 carbon atoms, in another embodiment with at least about 8 carbon atoms, in another embodiment with at least about 10 carbon atoms, in yet another embodiment with at least about 12 carbon atoms, in still another embodiment with at least about 14 carbon atoms, in another embodiment with at least about 16 carbon atoms, in yet another embodiment with at least about 18 carbon atoms, in still another embodiment with at least about 20 carbon atoms, in another embodiment with at least about 22 carbon atoms, in yet another embodiment with at least about 24 carbon atoms, in still another embodiment with at least about 26 carbon atoms, in another embodiment with at least about 28 carbon atoms, in yet another embodiment with at least about 30 carbon atoms, in still another embodiment with at least about 32 carbon atoms, in another embodiment with at least about 34 carbon atoms, in yet another embodiment with at least about 36 carbon atoms, in another embodiment with at least about 38 carbon atoms, in yet another embodiment with at least about 40 carbon atoms, and in still another embodiment with at least about 42 carbon atoms, and in one embodiment with no more than about 200 carbon atoms, in another embodiment with no more than about 100 carbon atoms, and in yet another embodiment with no more than about 44 carbon atoms, although the number of carbon atoms can be outside of these ranges, (iv) an alkylarylene group (including unsubstituted and substituted alkylarylene groups), in one embodiment with at least about 7 carbon atoms, in another embodiment with at least about 8 carbon atoms, in another embodiment with at least about 10 carbon atoms, in yet another embodiment with at least about 12 carbon atoms, in still another embodiment with at least about 14 carbon atoms, in another embodiment with at least about 16 carbon atoms, in yet another embodiment with at least about 18 carbon atoms, in still another embodiment with at least about 20 carbon atoms, in another embodiment with at least about 22 carbon atoms, in yet another embodiment with at least about 24 carbon atoms, in still another embodiment with at least about 26 carbon atoms, in another embodiment with at least about 28 carbon atoms, in yet another embodiment with at least about 30 carbon atoms, in still another embodiment with at least about 32 carbon atoms, in another embodiment with at least about 34 carbon atoms, in yet another embodiment with at least about 36 carbon atoms, in another embodiment with at least about 38 carbon atoms, in yet another embodiment with at least about 40 carbon atoms, and in still another embodiment with at least about 42 carbon atoms, and in one embodiment with no more than about 200 carbon atoms, in another embodiment with no more than about 100 carbon atoms, and in yet another embodiment with no more than about 44 carbon atoms, although the number of carbon atoms can be outside of these ranges, (v) an alkyleneoxy group (including linear, branched, saturated, unsaturated, cyclic, unsubstituted, and substituted alkyleneoxy groups, and wherein hetero atoms, such as oxygen, nitrogen, sulfur, silicon, phosphorus, and the like either may or may not be present in the alkyl portion of the alkyleneoxy group), in one embodiment with at least 1 carbon atom, in another embodiment with at least about 8 carbon atoms, in yet another embodiment with at least about 10 carbon atoms, in still another embodiment with at least about 12 carbon atoms, in another embodiment with at least about 14 carbon atoms, in yet another embodiment with at least about 16 carbon atoms, in still another embodiment with at least about 18 carbon atoms, in another embodiment with at least about 20 carbon atoms, in yet another embodiment with at least about 22 carbon atoms, in still another embodiment with at least about 24 carbon atoms, in another embodiment with at least about 26 carbon atoms, in yet another embodiment with at least about 28 carbon atoms, in still another embodiment with at least about 30 carbon atoms, in another embodiment with at least about 32 carbon atoms, in yet another embodiment with at least about 34 carbon atoms, and in still another embodiment with at least about 36 carbon atoms, and in one embodiment with no more than about 200 carbon atoms, in another embodiment with no more than about 100 carbon atoms, in yet another embodiment with no more than about 75 carbon atoms, in still another embodiment with no more than about 60 carbon atoms, in another embodiment with no more than about 50 carbon atoms, and in yet another embodiment with no more than about 40 carbon atoms, although the number of carbon atoms can be outside of these ranges, (vi) an aryleneoxy group (including unsubstituted and substituted aryleneoxy groups), in one embodiment with at least about 6 carbon atoms, in another embodiment with at least about 10 carbon atoms, in yet another embodiment with at least about 13 carbon atoms, in still another embodiment with at least about 14 carbon atoms, in another embodiment with at least about 16 carbon atoms, in yet another embodiment with at least about 17 carbon atoms, in still another embodiment with at least about 18 carbon atoms, in another embodiment with at least about 19 carbon atoms, in yet another embodiment with at least about 20 carbon atoms, in still another embodiment with at least about 21 carbon atoms, in another embodiment with at least about 22 carbon atoms, and in yet another embodiment with at least about 23 carbon atoms, and in one embodiment with no more than about 100 carbon atoms, in another embodiment with no more than about 75 carbon atoms, and in yet another embodiment with no more than about 50 carbon atoms, although the number of carbon atoms can be outside of these ranges, (vii) an arylalkyleneoxy group (including unsubstituted and substituted arylalkyleneoxy groups), in one embodiment with at least about 7 carbon atoms, in another embodiment with at least about 8 carbon atoms, in another embodiment with at least about 10 carbon atoms, in yet another embodiment with at least about 12 carbon atoms, in still another embodiment with at least about 14 carbon atoms, in another embodiment with at least about 16 carbon atoms, in yet another embodiment with at least about 18 carbon atoms, in still another embodiment with at least about 20 carbon atoms, in another embodiment with at least about 22 carbon atoms, in yet another embodiment with at least about 24 carbon atoms, in still another embodiment with at least about 26 carbon atoms, in another embodiment with at least about 28 carbon atoms, in yet another embodiment with at least about 30 carbon atoms, in still another embodiment with at least about 32 carbon atoms, in another embodiment with at least about 34 carbon atoms, in yet another embodiment with at least about 36 carbon atoms, in another embodiment with at least about 38 carbon atoms, in yet another embodiment with at least about 40 carbon atoms, and in still another embodiment with at least about 42 carbon atoms, and in one embodiment with no more than about 200 carbon atoms, in another embodiment with no more than about 100 carbon atoms, and in yet another embodiment with no more than about 44 carbon atoms, although the number of carbon atoms can be outside of these ranges, (viii) an alkylaryleneoxy group (including unsubstituted and substituted alkylaryleneoxy groups), in one embodiment with at least about 7 carbon atoms, in another embodiment with at least about 8 carbon atoms, in another embodiment with at least about 10 carbon atoms, in yet another embodiment with at least about 12 carbon atoms, in still another embodiment with at least about 14 carbon atoms, in another embodiment with at least about 16 carbon atoms, in yet another embodiment with at least about 18 carbon atoms, in still another embodiment with at least about 20 carbon atoms, in another embodiment with at least about 22 carbon atoms, in yet another embodiment with at least about 24 carbon atoms, in still another embodiment with at least about 26 carbon atoms, in another embodiment with at least about 28 carbon atoms, in yet another embodiment with at least about 30 carbon atoms, in still another embodiment with at least about 32 carbon atoms, in another embodiment with at least about 34 carbon atoms, in yet another embodiment with at least about 36 carbon atoms, in another embodiment with at least about 38 carbon atoms, in yet another embodiment with at least about 40 carbon atoms, and in still another embodiment with at least about 42 carbon atoms, and in one embodiment with no more than about 200 carbon atoms, in another embodiment with no more than about 100 carbon atoms, and in yet another embodiment with no more than about 44 carbon atoms, although the number of carbon atoms can be outside of these ranges, (ix) a polyalkyleneoxy group, wherein the alkyl portion of the repeat alkyleneoxy groups typically has from about 1 to about 12 carbon atoms, although the number of carbon atoms can be outside of these ranges, such as a polyethyleneoxy group, a polypropyleneoxy group, a polybutyleneoxy group, or the like, and wherein the number of repeat alkyleneoxy groups typically is from about 2 to about 50 repeat alkyleneoxy groups, although the number of repeat units can be outside of these ranges, (x) a polyaryleneoxy group, wherein the aryl portion of the repeat aryleneoxy groups typically has from about 6 to about 14 carbon atoms, although the number of carbon atoms can be outside of these ranges, such as a polyphenyleneoxy group, a polynaphthaleneoxy group, a polyphenanthreneoxy group, or the like, and wherein the number of repeat aryleneoxy groups typically is from about 2 to about 20 repeat aryleneoxy groups, although the number of repeat units can be outside of these ranges, (xi) a polyarylalkyleneoxy group, wherein the arylalkyl portion of the repeat arylalkyleneoxy groups typically has from about 7 to about 50 carbon atoms, although the number of carbon atoms can be outside of these ranges, such as a polybenzyleneoxy group, a polyphenylethyleneoxy group, or the like, and wherein the number of repeat arylalkyleneoxy groups typically is from about 2 to about 20 repeat arylalkyleneoxy groups, although the number of repeat units can be outside of these ranges, (xii) a polyalkylaryleneoxy group, wherein the alkylaryl portion of the repeat alkylaryleneoxy groups typically has from about 7 to about 50 carbon atoms, although the number of carbon atoms can be outside of these ranges, such as a polytolueneoxy group or the like, and wherein the number of repeat alkylaryleneoxy groups typically is from about 2 to about 20 repeat alkylaryleneoxy groups, although the number of repeat units can be outside of these ranges, (xiii) a heterocyclic group (including unsubstituted and substituted heterocyclic groups), typically with from about 2 to about 12 carbon atoms, and typically with from about 4 to about 18 ring atoms, although the number of carbon atoms and the number of ring atoms can be outside of these ranges, wherein the heteroatoms in the heterocyclic groups can be (but are not limited to) nitrogen, oxygen, sulfur, silicon, phosphorus, and the like, as well as mixtures thereof, (xiv) a silylene group (including unsubstituted and substituted silylene groups), (xv) a siloxane group (including unsubstituted and substituted siloxane groups), (xvi) a polysilylene group (including unsubstituted and substituted polysilylene groups), typically with from 2 to about 100 repeat silylene units, or (xvii) a polysiloxane group (including unsubstituted and substituted polysiloxane groups), typically with from 2 to about 200 repeat siloxane units, although the number of repeat siloxane units can be outside of this range, wherein the substituents on the substituted, alkylene, arylene, arylalkylene, alkylarylene, alkyleneoxy, aryleneoxy, arylalkyleneoxy, alkylaryleneoxy, polyalkyleneoxy, polyaryleneoxy, polyarylalkyleneoxy, polyalkylaryleneoxy, heterocyclic, silylene, siloxy, polysilylene, and polysiloxy groups are hydroxy groups, halogen atoms, cyano groups, ether groups, aldehyde groups, ketone groups, carboxylic acid groups, ester groups, amide groups, carbonyl groups, thiocarbonyl groups, sulfate groups, sulfonate groups, sulfide groups, sulfoxide groups, phosphate groups, nitrile groups, mercapto groups, nitro groups, nitroso groups, sulfone groups, acyl groups, acid anhydride groups, azide groups, cyanato groups, isocyanato groups, thiocyanato groups, isothiocyanato groups, mixtures thereof, and the like, wherein the substituents on the silylene, siloxy, polysilylene, and polysiloxy groups can also be alkyl groups, aryl groups, arylalkyl groups, and alkylaryl groups, wherein two or more substituents con be joined together to form a ring.

Some specific examples of suitable $R_{10}$ groups include (but are not limited to) n-hexanediyl, of the formula —$(CH_2)_6$—, n-octanediyl, of the formula —$(CH_2)_8$—, n-deconediyl, of the formula —$(CH_2)_{10}$—, n-dodecanediyl, of the formula —$(CH_2)_{12}$—, 3-methyl-1,5-pentanediyl, of the formula

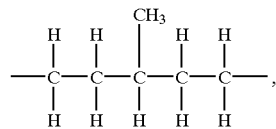

1,4-cyclohexanedimethylene, of the formula (which is not intended to be limited to any particular stereochemistry and includes all cis and trans isomers)

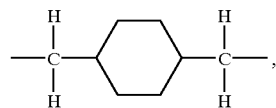

4,4'-isopropylidenedicyclohexanediyl, of the formula (which is not intended to be limited to any particular stereochemistry and includes all cis and trans isomers)

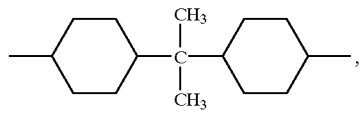

4,4'-bicyclohexyanediyl, of the formula (which is not intended to be limited to any particular stereochemistry and includes all cis and trans isomers)

a branched alkylene group having 36 carbon atoms, including isomers of the formula

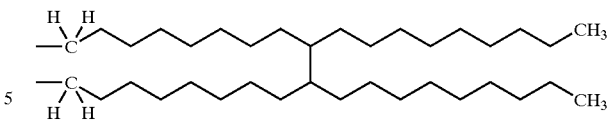

and other branched alkylene isomers (which may include unsaturations and cyclic groups), 4,8-bis(methylene)tricyclo[$5210^{2,6}$]decanediyl, of the formula (which is not intended to be limited to any particular stereochemistry and includes all cis and trans isomers)

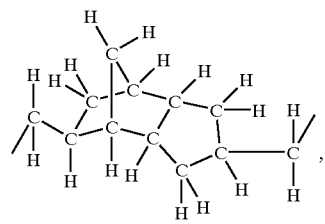

and the like.

X and X' each, independently of the others, is (i) a direct bond, (ii) an oxygen atom, (iii) a sulfur atom, (iv) a group of the formula —$NR_{40}$— wherein $R_{40}$ is a hydrogen atom, an alkyl group (including linear, branched, saturated, unsaturated, cyclic, unsubstituted, and substituted alkyl groups, and wherein hetero atoms, such as oxygen, nitrogen, sulfur, silicon, phosphorus, and the like either may or may not be present in the alkyl group), typically with from 1 to about 50 carbon atoms, preferably with from about 2 to about 20 carbon atoms, and more preferably with from about 4 to about 12 carbon atoms, although the number of carbon atoms can be outside of these ranges, an aryl group (including substituted aryl groups), typically with from about 6 to about 50 carbon atoms, preferably with from about 6 to about 20 carbon atoms, and more preferably with from about 6 to about 10 carbon atoms, although the number of carbon atoms can be outside of these ranges, an arylalkyl group (including substituted arylalkyl groups), typically with from about 7 to about 100 carbon atoms, preferably with from about 7 to about 50 carbon atoms, and more preferably with from about 7 to about 20 carbon atoms, although the umber of carbon atoms can be outside of these ranges, or an alkylaryl group (including substituted alkylaryl groups), typically with from about 7 to about 100 carbon atoms, preferably with from about 7 to about 50 carbon atoms, and more preferably with from about 7 to about 20 carbon atoms, although the number of carbon atoms can be outside of these ranges, or (v) a group of the formula —$CR_{50}R_{60}$— wherein $R_{50}$ and $R_{60}$ each, independently of the other, is a hydrogen atom, an alkyl group (including linear, branched, saturated, unsaturated, cyclic, unsubstituted, and substituted alkyl groups, and wherein hetero atoms, such as oxygen, nitrogen, sulfur, silicon, phosphorus, and the like either may or may not be present in the alkyl group), typically with from 1 to about 50 carbon atoms, preferably with from about 2 to about 20 carbon atoms, and more preferably with from about 4 to about 12 carbon atoms, although the number of carbon atoms can be outside of these ranges, an aryl group (including substituted aryl groups), typically with from about 6 to about 50 carbon atoms, preferably with from about 6 to about 20 carbon atoms, and more preferably with from about 6 to about 10 carbon atoms, although the number of carbon atoms can be outside of these ranges, an arylalkyl group (including substituted arylalkyl groups), typically with from about 7 to about 100 carbon atoms, preferably with from about 7 to about 50 carbon atoms, and more preferably with from about 7 to about 20 carbon atoms, although the number of carbon atoms can be outside of these ranges, or an alkylaryl group (including substituted alkylaryl groups), typically with from about 7 to about 100 carbon atoms, preferably with from about 7 to about 50 carbon atoms, and more preferably with from about 7 to about 20 carbon atoms, although the number of carbon atoms can be outside of these ranges, wherein the substituents on the substituted alkyl, aryl, arylalkyl, and alkylaryl groups can be (but are not limited to) hydroxy groups, halogen atoms, amine groups, imine groups, ammonium groups, pyridine groups, pyridinium groups, ether groups, aldehyde groups, ester groups, amide groups, carbonyl groups, thiocarbonyl groups, sulfate groups, sulfonate groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, cyanato groups, isocyanato groups, thiocyanato groups, isothiocyanato groups, mixtures thereof, and the like, wherein two or more substituents can be joined together to form a ring, and wherein X and X' can be the some as each other or different from each other.

Z and Z' each, independently of the others, is (i) a hydrogen atom, (ii) a halogen atom, including fluorine, chlorine, bromine, and iodine, (iii) a nitro group, (iv) an alkyl group (including linear, branched, saturated, unsaturated, cyclic, unsubstituted, and substituted alkyl groups, and wherein hetero atoms, such as oxygen, nitrogen, sulfur, silicon, phosphorus, and the like either may or may not be present in the alkyl group), typically with from 1 to about 50 carbon atoms, preferably with from about 1 to about 20 carbon atoms, and more preferably with from about 1 to about 10 carbon atoms, although the number of carbon atoms can be outside of these ranges, (vi an aryl group (including substituted aryl groups), typically with from about 6 to about 50 carbon atoms, preferably with from about 6 to about 14 carbon atoms, and more preferably with from about 6 to about 10 carbon atoms, although the number of carbon atoms can be outside of these ranges, (vi) an arylalkyl group (including substituted arylalkyl groups), typically with from about 7 to about 50 carbon atoms, preferably with from about 7 to about 25 carbon atoms, and more preferably with from about 7 to about 15 carbon atoms, although the number of carbon atoms can be outside of these ranges, (vii) an alkylaryl group (including substituted alkylaryl groups), typically with from about 7 to about 50 carbon atoms, preferably with from about 7 to about 25 carbon atoms, and more preferably with from about 7 to about 15 carbon atoms, although the number of carbon atoms can be outside of these ranges, (viii) a group of the formula

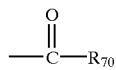

wherein $R_{70}$ is an alkyl group (including linear, branched, saturated, unsaturated, cyclic, unsubstituted, and substituted alkyl groups, and wherein hetero atoms, such as oxygen, nitrogen, sulfur, silicon, phosphorus, and the like either may or may not be present in the alkyl group), typically with from 1 to about 50 carbon atoms, preferably with from about 1 to about 20 carbon atoms, and more preferably with from about 1 to about 10 carbon atoms, although the number of carbon atoms can be outside of these ranges, an aryl group (including substituted aryl groups), typically with from about 6 to about 50 carbon atoms, preferably with from about 6 to about 20 carbon atoms, and more preferably with from about 6 to about 14 carbon atoms, although the number of carbon atoms can be outside of these ranges, an arylalkyl group (including substituted arylalkyl groups), typically with from about 7 to about 50 carbon atoms, preferably with from about 7 to about 25 carbon atoms, and more preferably with from about 7 to about 15 carbon atoms, although the number of carbon atoms can be outside of these ranges, an alkylaryl group (including substituted alkylaryl groups), typically with from about 7 to about 50 carbon atoms, preferably with from about 7 to about 25 carbon atoms, and more preferably with from about 7 to about 15 carbon atoms, although the number of carbon atoms can be outside of these ranges, an alkoxy group (including linear, branched, saturated, unsaturated, cyclic, unsubstituted, and substituted alkoxy groups, and wherein hetero atoms, such as oxygen, nitrogen, sulfur, silicon, phosphorus, and the like either may or may not be present in the alkyl portion of the alkoxy group), typically with from about 1 to about 50 carbon atoms, preferably with from about 4 to about 20 carbon atoms, and more preferably with from about 8 to about 12 carbon atoms, although the number of carbon atoms can be outside of these ranges, an aryloxy group (including substituted aryloxy groups), typically with from about 6 to about 50 carbon atoms, preferably with from about 6 to about 20 carbon atoms, and more preferably with from about 6 to about 14 carbon atoms, although the number of carbon atoms can be outside of these ranges, an arylalkyloxy group (including substituted arylalkyloxy groups), typically with from about 7 to about 50 carbon atoms, preferably with from about 7 to about 25 carbon atoms, and more preferably with from about 7 to about 15 carbon atoms, although the number of carbon atoms can be outside of these ranges, an alkylaryloxy group (including substituted alkylaryloxy groups), typically with from about 7 to about 50 carbon atoms, preferably with from about 7 to about 25 carbon atoms, and more preferably with from about 7 to about 15 carbon atoms, although the number of carbon atoms can be outside of these ranges, a polyalkyleneoxy group, wherein the alkyl portion of the repeat alkyleneoxy groups typically has from about 1 to about 12 carbon atoms, although the number of carbon atoms can be outside of these ranges, such as a polyethyleneoxy group, a polypropyleneoxy group, a polybutyleneoxy group, or the like, and wherein the number of repeat alkyleneoxy groups typically is from about 2 to about 50 repeat alkyleneoxy groups, although the number of repeat units can be outside of these ranges, a polyaryleneoxy group, wherein the aryl portion of the repeat aryleneoxy groups typically has from about 6 to about 14 carbon atoms, although the number of carbon atoms can be outside of these ranges, such as a polyphenyleneoxy group, a polynaphthaleneoxy group, a polyphenanthreneoxy group, or the like, and wherein the number of repeat aryleneoxy groups typically is from about 2 to about 20 repeat aryleneoxy groups, although the number of repeat units can be outside of these ranges, a polyarylalkyleneoxy group, wherein the arylalkyl portion of the repeat arylalkyleneoxy groups typically has from about 7 to about 50 carbon atoms, although the number of carbon atoms can be outside of these ranges, such as a polybenzyleneoxy group, a polyphenylethyleneoxy group, or the like, and wherein the number of repeat arylalkyleneoxy groups typically is from about 2 to about 20 repeat arylalkyleneoxy groups, although the number of repeat units can be outside of these ranges, a polyalkylaryleneoxy group, wherein the alkylaryl portion of the repeat alkylaryleneoxy groups typically has from about 7 to about 50 carbon atoms, although the number of carbon atoms can be outside of these ranges, such as a polytolueneoxy group or the like, and wherein the number of repeat alkylaryleneoxy groups typically is from about 2 to about 20 repeat alkylaryleneoxy groups, although the number of repeat units can be outside of these ranges, a heterocyclic group (including unsubstituted and substituted heterocyclic groups), typically with from about 2 to about 12 carbon atoms, and typically with from about 4 to about 18 ring atoms, although the number of carbon atoms and the number of ring atoms can be outside of these ranges, wherein the heteroatoms in the heterocyclic groups can be (but are not limited to) nitrogen, oxygen, sulfur, silicon, phosphorus, and the like, as well as mixtures thereof, a silyl group (including unsubstituted and substituted silyl groups), a siloxane group (including unsubstituted and substituted siloxane groups), a polysilylene group (including unsubstituted and substituted polysilylene groups), typically with from 2 to about 100 repeat silylene units, or a polysiloxane group (including unsubstituted and substituted polysiloxane groups), typically with from 2 to about 200 repeat siloxane units, although the number of repeat siloxane units can be outside of this range, (ix) a sulfonyl group of the formula —SO$_2$R$_{80}$, wherein R$_{80}$ is a hydrogen atom, an alkyl group (including linear, branched, saturated, unsaturated, cyclic, unsubstituted, and substituted alkyl groups, and wherein hetero atoms, such as oxygen, nitrogen, sulfur, silicon, phosphorus, and the like either may or may not be present in the alkyl group), typically with from 1 to about 50 carbon atoms, preferably with from about 1 to about 20 carbon atoms, and more preferably with from about 1 to about 10 carbon atoms, although the number of carbon atoms can be outside of these ranges, an aryl group (including substituted aryl groups), typically with from about 6 to about 50 carbon atoms, preferably with from about 6 to about 20 carbon atoms, and more preferably with from about 6 to about 14 carbon atoms, although the number of carbon atoms can be outside of these ranges, an arylalkyl group (including substituted arylalkyl groups), typically with from about 7 to about 50 carbon atoms, preferably with from about 7 to about 25 carbon atoms, and more preferably with from about 7 to about 15 carbon atoms, although the number of carbon atoms can be outside of these ranges, an alkylaryl group (including substituted alkylaryl groups), typically with from about 7 to about 50 carbon atoms, preferably with from about 7 to about 25 carbon atoms, and more preferably with from about 7 to about 15 carbon atoms, although the number of carbon atoms can be outside of these ranges, an alkoxy group (including linear, branched, saturated, unsaturated, cyclic, unsubstituted, and substituted alkoxy groups, and wherein hetero atoms, such as oxygen, nitrogen, sulfur, silicon, phosphorus, and the like either may or may not be present in the alkyl portion of the alkoxy group), typically with from about 1 to about 50 carbon atoms, preferably with from about 4 to about 20 carbon atoms, and more preferably with from about 8 to about 12 carbon atoms, although the number of carbon atoms can be outside of these ranges, an aryloxy group (including substituted aryloxy groups), typically with from about 6 to about 50 carbon atoms, preferably with from about 6 to about 20 carbon atoms, and more preferably with from about 6 to about 14 carbon atoms, although the number of carbon atoms can be outside of these ranges, an arylalkyloxy group (including substituted arylalkyloxy groups), typically with from about 7 to about 50 carbon atoms, preferably with from about 7 to about 25 carbon atoms, and more preferably with from about 7 to about 15 carbon atoms, although the number of carbon atoms can be outside of these ranges, an alkylaryloxy group (including substituted alkylaryloxy groups), typically with from about 7 to about 50 carbon atoms, preferably with from about 7 to about 25 carbon atoms, and more preferably with from about 7 to about 15 carbon atoms, although the number of carbon atoms can be outside of these ranges, a polyalkyleneoxy group, wherein the alkyl portion of the repeat alkyleneoxy groups typically has from about 1 to about 12 carbon atoms, although the number of carbon atoms can be outside of these ranges, such as a polyethyleneoxy group, a polypropyleneoxy group, a polybutyleneoxy group, or the like, and wherein the number of repeat alkyleneoxy groups typically is from about 2 to about 50 repeat alkyleneoxy groups, although the number of repeat units can be outside of these ranges, a polyaryleneoxy group, wherein the aryl portion of the repeat aryleneoxy groups typically has from about 6 to about 14 carbon atoms, although the number of carbon atoms can be outside of these ranges, such as a polyphenyleneoxy group, a polynaphthaleneoxy group, a polyphenanthreneoxy group, or the like, and wherein the number of repeat aryleneoxy groups typically is from about 2 to about 20 repeat aryleneoxy groups, although the number of repeat units can be outside of these ranges, a polyarylalkyleneoxy group, wherein the arylalkyl portion of the repeat arylalkyleneoxy groups typically has from about 7 to about 50 carbon atoms, although the number of carbon atoms can be outside of these ranges, such as a polybenzyleneoxy group, a polyphenylethyleneoxy group, or the like, and wherein the number of repeat arylalkyleneoxy groups typically is from about 2 to about 20 repeat arylalkyleneoxy groups, although the number of repeat units can be outside of these ranges, a polyalkylaryleneoxy group, wherein the alkylaryl portion of the repeat alkylaryleneoxy groups typically has from about 7 to about 50 carbon atoms, although the number of carbon atoms can be outside of these ranges, such as a polytolueneoxy group or the like, and wherein the number of repeat alkylaryleneoxy groups typically is from about 2 to about 20 repeat alkylaryleneoxy groups, although the number of repeat units can be outside of these ranges, a heterocyclic group (including unsubstituted and substituted heterocyclic groups), typically with from about 2 to about 12 carbon atoms, and typically with from about 4 to about 18 ring atoms, although the number of carbon atoms and the number of ring atoms can be outside of these ranges, wherein the heteroatoms in the heterocyclic groups can be (but are not limited to) nitrogen, oxygen, sulfur, silicon, phosphorus, and the like, as well as mixtures thereof, a silyl group (including unsubstituted and substituted silyl groups), a siloxane group (including unsubstituted and substituted siloxane groups), a polysilylene group (including unsubstituted and substituted polysilylene groups), typically with from 2 to about 100 repeat silylene units, or a polysiloxane group (including unsubstituted and substituted polysiloxane groups), typically with from 2 to about 200 repeat siloxane units, although the number of repeat siloxane units can be outside of this range, or (x) a phosphoryl group of the formula —PO$_3$R$_{90}$, wherein R$_{90}$ is a hydrogen atom, an alkyl group (including linear, branched, saturated, unsaturated, cyclic, unsubstituted, and substituted alkyl groups, and wherein hetero atoms, such as oxygen, nitrogen, sulfur, silicon, phosphorus, and the like either may or may not be present in the alkyl group), typically with from 1 to about 50 carbon atoms, preferably with from about 1 to about 20 carbon atoms, and more preferably with from about 1 to about 10 carbon atoms, although the number of carbon atoms can be outside of these ranges, an aryl group (including substituted aryl groups), typically with from about 6 to about 50 carbon atoms, preferably with from about 6 to about 20 carbon atoms, and more preferably with from about 6 to about 14 carbon atoms, although the number of carbon atoms can be outside of these ranges, an arylalkyl group (including substituted arylalkyl groups), typically with from about 7 to about 50 carbon atoms, preferably with from about 7 to about 25 carbon atoms, and more preferably with from about 7 to about 15 carbon atoms, although the number of carbon atoms can be outside of these ranges, an alkylaryl group (including substituted alkylaryl groups), typically with from about 7 to about 50 carbon atoms, preferably with from about 7 to about 25 carbon atoms, and more preferably with from about 7 to about 15 carbon atoms, although the number of carbon atoms can be outside of these ranges, an alkoxy group (including linear, branched, saturated, unsaturated, cyclic, unsubstituted, and substituted alkoxy groups, and wherein hetero atoms, such as oxygen, nitrogen, sulfur, silicon, phosphorus, and the like either may or may not be present in the alkyl portion of the alkoxy group), typically with from about 1 to about 50 carbon atoms, preferably with from about 4 to about 20 carbon atoms, and more preferably with from about 8 to about 12 carbon atoms, although the number of carbon atoms can be outside of these ranges, an aryloxy group (including substituted aryloxy groups), typically with from about 6 to about 50 carbon atoms, preferably with from about 6 to about 20 carbon atoms, and more preferably with from about 6 to about 14 carbon atoms, although the number of carbon atoms can be outside of these ranges, an arylalkyloxy group (including substituted arylalkyloxy groups), typically with from about 7 to about 50 carbon atoms, preferably with from about 7 to about 25 carbon atoms, and more preferably with from about 7 to about 15 carbon atoms, although the number of carbon atoms can be outside of these ranges, an alkylaryloxy group (including substituted alkylaryloxy groups), typically with from about 7 to about 50 carbon atoms, preferably with from about 7 to about 25 carbon atoms, and more preferably with from about 7 to about 15 carbon atoms, although the number of carbon atoms can be outside of these ranges, a polyalkyleneoxy group, wherein the alkyl portion of the repeat alkyleneoxy groups typically has from about 1 to about 12 carbon atoms, although the number of carbon atoms can be outside of these ranges, such as a polyethyleneoxy group, a polypropyleneoxy group, a polybutyleneoxy group, or the like, and wherein the number of repeat alkyleneoxy groups typically is from about 2 to about 50 repeat alkyleneoxy groups, although the number of repeat units can be outside of these ranges, a polyaryleneoxy group, wherein the aryl portion of the repeat aryleneoxy groups typically has from about 6 to about 14 carbon atoms, although the number of carbon atoms can be outside of these ranges, such as a polyphenyleneoxy group, a polynaphthaleneoxy group, a polyphenanthreneoxy group, or the like, and wherein the number of repeat aryleneoxy groups typically is from about 2 to about 20 repeat aryleneoxy groups, although the number of repeat units can be outside of these ranges, a polyarylalkyleneoxy group, wherein the arylalkyl portion of the repeat arylalkyleneoxy groups typically has from about 7 to about 50 carbon atoms, although the number of carbon atoms can be outside of these ranges, such as a polybenzyleneoxy group, a polyphenylethyleneoxy group, or the like, and wherein the number of repeat arylalkyleneoxy groups typically is from about 2 to about 20 repeat arylalkyleneoxy groups, although the number of repeat units can be outside of these ranges, a polyalkylaryleneoxy group, wherein the alkylaryl portion of the repeat alkylaryleneoxy groups typically has from about 7 to about 50 carbon atoms, although the number of carbon atoms can be outside of these ranges, such as a polytolueneoxy group or the like, and wherein the number of repeat alkylaryleneoxy groups typically is from about 2 to about 20 repeat alkylaryleneoxy groups, although the number of repeat units can be outside of these ranges, a heterocyclic group (including unsubstituted and substituted heterocyclic groups), typically with from about 2 to about 12 carbon atoms, and typically with from about 4 to about 18 ring atoms, although the number of carbon atoms and the number of ring atoms can be outside of these ranges, wherein the heteroatoms in the heterocyclic groups can be (but are not limited to) nitrogen, oxygen, sulfur, silicon, phosphorus, and the like, as well as mixtures thereof, a silyl group (including unsubstituted and substituted silyl groups), a siloxane group (including unsubstituted and substituted siloxane groups), a polysilylene group (including unsubstituted and substituted polysilylene groups), typically with from 2 to about 100 repeat silylene units, or a polysiloxane group (including unsubstituted and substituted polysiloxane groups), typically with from 2 to about 200 repeat siloxane units, although the number of repeat siloxane units can be outside of this range, wherein the substituents on the substituted alkyl, aryl, arylalkyl, alkylaryl, alkoxy, aryloxy, arylalkyloxy, alkylaryloxy, polyalkyleneoxy, polyaryleneoxy, polyarylalkyleneoxy, polyalkylaryleneoxy, heterocyclic, silyl, siloxy, polysilylene, and polysiloxy groups are hydroxy groups, halogen atoms, cyano groups, ether groups, aldehyde groups, ketone groups, carboxylic acid groups, ester groups, amide groups, carbonyl groups, thiocarbonyl groups, sulfate groups, sulfonate groups, sulfide groups, sulfoxide groups, phosphate groups, nitrile groups, mercapto groups, nitro groups, nitroso groups, sulfone groups, acyl groups, acid anhydride groups, azide groups, cyanato groups, isocyanato groups, thiocyanato groups, isothiocyanato groups, mixtures thereof, and the like, wherein the substituents on the silylene, siloxy, polysilylene, and polysiloxy groups can also be alkyl groups, aryl groups, arylalkyl groups, and alkylaryl groups, wherein two or more substituents can be joined together to form a ring, and wherein Z and Z' con be the same as each other or different from each other. Up to 4 Z groups can be present on the molecule. Up to 4 Z' groups can be present on the molecule.

The groups Z and X can be joined together to form a ring and the groups Z' and X' can be joined together to form a ring.

For example, colorant molecules can be prepared by diazotization of the correspondingly substituted dimeric aniline with nitrosylsulfuric acid under cold temperature conditions, followed by coupling with the correspondingly substituted pyridone in a buffered alkaline aqueous solution under cold temperature conditions, as follows:

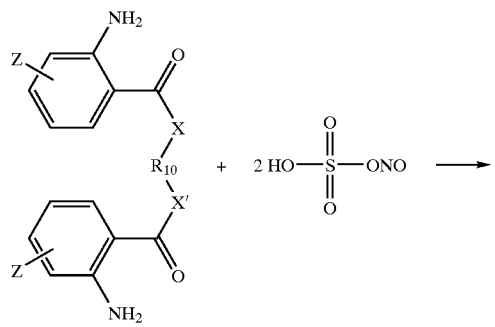

-continued

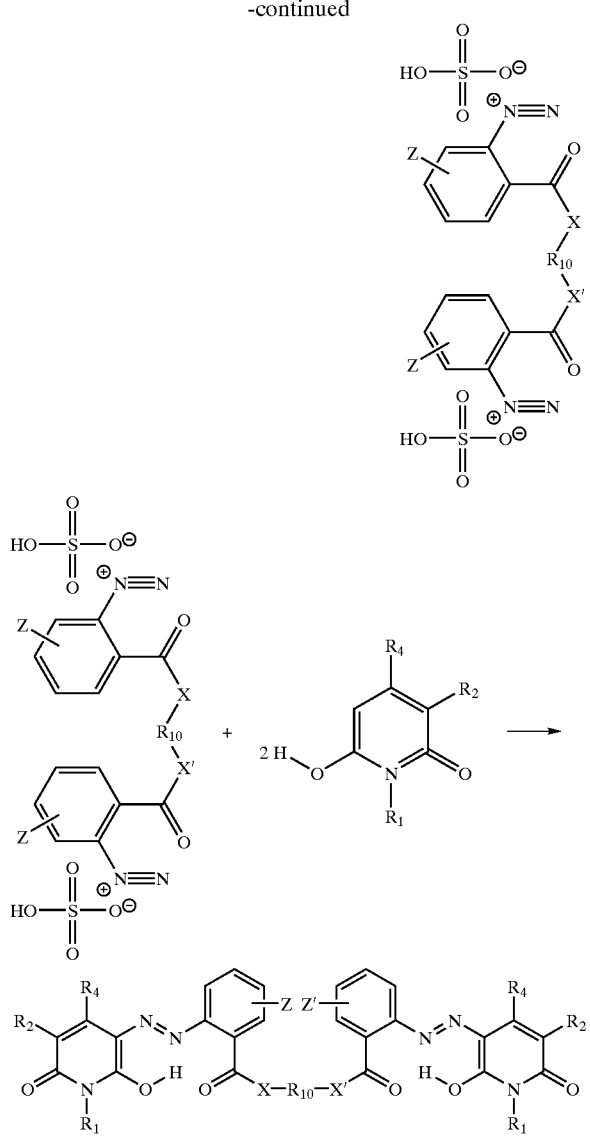

In the synthesis, the correspondingly substituted dianiline is first subjected to a diazotization reaction by dissolving it in acetic acid diluted with a solvent and, optionally, a second acid, such as sulfuric acid, dodecylbenzene sulfonic acid, propionic acid, hydrochloric acid, phosphoric acid, any other acid useful for a diazotization reaction, or the like, as well as mixtures thereof. The solvent can be any solvent useful in a diazotization reaction, such as water, acetone, dimethylformamide, dimethyacetamide, tetrohydrofuran, dimethoxyethane, analogous higher-boiling ether solvents, and the like, as well as mixtures thereof.

The solvent and the dianiline are present in any desired or effective relative amounts; if, for purposes of determining relative amounts, "solvent" is defined to include whatever solvent has been selected plus any amount of acetic acid and second acid present, the reactants are present in this combined solvent in relative amounts of in one embodiment at least about 100 grams of substituted dianiline per liter of solvent, in another embodiment at least about 200 grams of substituted dianiline per liter of solvent, and in yet another embodiment at least about 230 grams of substituted dianiline per liter of solvent, and in one embodiment of no more than about 400 grams of substituted dianiline per liter of solvent, in another embodiment of no more than about 300 grams of substituted dianiline per liter of solvent, and in yet another embodiment of no more than about 270 grams of substituted dianiline per liter of solvent, although the relative amounts can be outside of these ranges.

The acetic acid is present in any desired or effective amount, in one embodiment at least about 1 gram of acetic acid per gram of substituted dianiline, in another embodiment at least about 2 grams of acetic acid per gram of substituted dianiline, and in yet another embodiment at least about 3 grams of acetic acid per gram of substituted dianiline, and in one embodiment no more than about 10 grams of acetic acid per gram of substituted dianiline, in another embodiment no more than about 7 grams of acetic acid per gram of substituted dianiline, and in yet another embodiment no more than about 5 grams of acetic acid per gram of substituted dianiline, although the relative amounts can be outside of these ranges.

When present, the optional second acid is present in any desired or effective amount, in one embodiment at least about 0.05 gram of acid per gram of substituted dianiline, and in another embodiment at least about 0.1 gram of acid per gram of substituted dianiline, and in one embodiment no more than about 0.5 grams of acid per gram of substituted dianiline, in another embodiment no more than about 0.3 grams of acid per gram of substituted dianiline, and in yet another embodiment no more than about 0.2 grams of acid per gram of substituted dianiline, although the relative amounts can be outside of these ranges.

In the mixture comprising the selected solvent, any optional second acid, and acetic acid, the acetic acid is present in any desired or effective amount, in one embodiment at least about 50 percent by volume of the mixture, in another embodiment at least about 70 percent by volume of the mixture, in yet another embodiment at least about 75 percent by volume of the mixture, and in still another embodiment at least about 95 percent by volume of the mixture, although the relative amount can be outside of these ranges.

Upon complete dissolution of the ingredients, the mixture is cooled, in one embodiment to a temperature of no more than about +15° C., in another embodiment to a temperature of no more than about +10° C., in yet another embodiment to a temperature of no more than about +5° C., in still another embodiment to a temperature of no more than about +3° C., and in one embodiment to a temperature of no lower than about −5° C., and in another embodiment to a temperature of no lower than about −10° C., although the temperature can be outside of these ranges.

Thereafter, nitrosylsulfuric acid is added to the mixture in any desired or effective amount, in one embodiment at least about 2 moles of nitrosylsulfuric acid per mole of substituted dianiline (i.e., at least about 1 mole of nitrosylsulfuric acid per mole of aniline moiety in the dianiline), and in another embodiment at least about 2.1 moles of nitrosylsulfuric acid per mole of substituted dianiline, and in one embodiment no more than about 3 moles of nitrosylsulfuric acid per mole of substituted dianiline, in another embodiment no more than about 2.5 moles of nitrosylsulfuric acid per mole of substituted dianiline, and in yet another embodiment no more than about 2.25 moles of nitrosylsulfuric acid per mole of substituted dianiline, although the relative amounts can be outside of these ranges. In a specific embodiment, the nitrosylsulfuric acid is added dropwise at a rate such that the temperature of the reaction mixture does not exceed 15° C.

The reaction to form the diazonium salt is essentially instantaneous, and upon completion of addition of the nitrosylsulfuric acid the reaction is essentially complete, although, if desired, a qualitative test can be performed to confirm reaction completion.

Thereafter, residual excess nitrosylsulfuric acid present in the reaction mixture can be quenched by the addition of a quenching agent, such as sulfamic acid, urea, or the like as well as mixtures thereof, in any desired or effective amount, in one embodiment at least about 0.01 mole of quenching agent per mole of nitrosylsulfuric acid (i.e., per mole of nitrosylsulfuric acid originally added to the reaction mixture), in another embodiment at least about 0.05 mole of quenching agent per mole of nitrosylsulfuric acid, and in yet another embodiment at least about 0.1 mole of quenching agent per mole of nitrosylsulfuric acid, and in one embodiment no more than about 0.5 mole of quenching agent per mole of nitrosylsulfuric acid, in another embodiment no more than about 0.3 mole of quenching agent per mole of nitrosylsulfuric acid, and in yet another embodiment no more than about 0.2 mole of quenching agent per mole of nitrosylsulfuric acid, although the amount can be outside of these ranges. Upon completion of the reaction, the reaction mixture contains the corresponding diazonium salt.

A precursor solution of the pyridone having the desired substituents thereon is prepared in an appropriate solvent, such as a mixture of water, organic solvents, including lower alcohols such as ethanol, ethanol, isopropanol, and the like, water-miscible nonbasic organic solvents such as tetrahydrofuran, acetone, dimethoxyethane, N,N-dimethylformamide, N,N-dimethylacetamide, and the like, as well as mixtures thereof. Mixtures of water with an organic solvent can be helpful for ease of solvating inorganic or organic salts that are a reaction by-product. In this instance, water and the organic solvent are present in any desired or effective relative amounts, in one embodiment at least about 0.25 gram of organic solvent per gram of water, in another embodiment at least about 0.3 gram of organic solvent per gram of water, and in yet another embodiment at least about 0.4 gram of organic solvent per gram of water, and in one embodiment no more than about 4 grams of organic solvent per gram of water, in another embodiment no more than about 3 grams of organic solvent per gram of water, and in yet another embodiment no more than about 2 grams of organic solvent per gram of water, although the relative amounts can be outside of these ranges.

The pyridone is present in the precursor solution in any desired or effective amount, in one embodiment at least about 10 grams of pyridone per liter of solvent, in another embodiment at least about 30 grams of pyridone per liter of solvent, and in yet another embodiment at least about 50 grams of pyridone per liter of solvent, and in one embodiment no more than about 200 grams of pyridone per liter of solvent. In another embodiment no more than about 100 grams of pyridone per liter of solvent, and in yet another embodiment no more than about 70 grams of pyridone per liter of solvent, although the relative amounts can be outside of these ranges.

The pyridone precursor solution is maintained at an alkaline pH, typically of at least about 10, and in one embodiment no more than about 14, and in another embodiment no more than about 12, although the pH can be outside of these ranges. The pyridone precursor solution can contain a mixture of a base and an optional buffering salt.

Examples of suitable bases include mineral bases, such as sodium hydroxide, potassium hydroxide, and the like, as well as water-miscible organic tertiary amines, such as triethanolamine, N,N-diethylethanolamine, and the like, as well as mixtures thereof, present in any desired or effective amount, in one embodiment at least about 1 mole of base per mole of pyridone, in another embodiment at least about 2 moles of base per mole of pyridone, in yet another embodiment at least about 3 moles of base per mole of pyridone, and in still another embodiment at least about 5 moles of base per mole of pyridone, and in one embodiment no more than about 10 moles of base per mole of pyridone, in another embodiment no more than about 7 moles of base per mole of pyridone, and in yet another embodiment no more than about 5 moles of base per mole of pyridone, although the relative amounts can be outside of these ranges.

Examples of suitable optional buffer salts include those corresponding to the principal acid solvent; for example, when the principal acid solvent is acetic acid, suitable buffers include sodium acetate, potassium acetate, sodium hydrogenphosphate, citric acid, and the like, as well as mixtures thereof. When present, the optional buffer salt is present in any desired or effective amount, in one embodiment at least about 1 mole of buffer per mole of pyridone, in another embodiment at least about 2 moles of buffer per mole of pyridone, in yet another embodiment at least about 3 moles of buffer per mole of pyridone, and in still another embodiment at least about 5 moles of buffer per mole of pyridone, and in one embodiment no more than about 10 moles of buffer per mole of pyridone, in another embodiment no more than about 7 moles of buffer per mole of pyridone, and in yet another embodiment no more than about 5 moles of buffer per mole of pyridone, although the relative amounts can be outside of these ranges. In a specific embodiment, upon dissolution of the pyridone, the thus-formed precursor pyridone solution can be filtered to remove any undissolved solids.

The solution containing the diazonium salt, maintained at a cold temperature, is then slowly added to the pyridone solution in any desired or effective relative amounts, in one embodiment at least about 2 moles of pyridone per mole of diazonium salt, in another embodiment at least about 2.1 moles of pyridone per mole of diazonium salt, and in yet another embodiment at least about 2.25 moles of pyridone per mole of diazonium salt, and in one embodiment no more than about 4 moles of pyridone per mole of diazonium salt, in another embodiment no more than about 3 moles of pyridone per mole of diazonium salt, and in yet another embodiment no more than about 2.5 moles of pyridone per mole of diazonium salt, although the relative amounts can be outside of these ranges, resulting in the immediate formation of a bright yellow precipitate. Thereafter, the yellow precipitate can be collected by filtration and, if desired, washed.

When the pyridone prepared according to the process of the present invention is a dipyridone of the formula

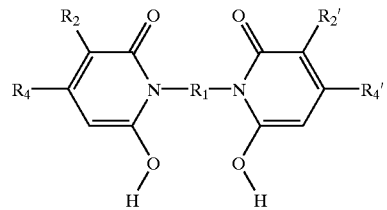

the dipyridone can be reacted with a diazonium salt of the formula

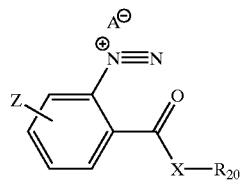

to form a colorant compound of the formula

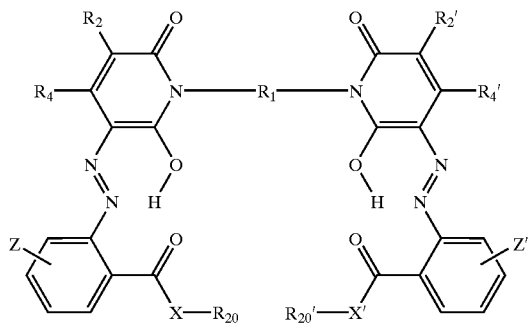

wherein $R_{20}$ and $R_{20}'$ each, independently of the other, is (i) an alkyl group (including linear, branched, saturated, unsaturated, cyclic, unsubstituted, and substituted alkyl groups, and wherein hetero atoms, such as oxygen, nitrogen, sulfur, silicon, phosphorus, and the like may or may not be present in the alkyl group), in one embodiment with at least 1 carbon atom, in another embodiment with at least about 8 carbon atoms, in yet another embodiment with at least about 10 carbon atoms, in still another embodiment with at least about 12 carbon atoms, in another embodiment with at least about 14 carbon atoms, in yet another embodiment with at least about 16 carbon atoms, in still another embodiment with at least about 18 carbon atoms, in another embodiment with at least about 20 carbon atoms, in yet another embodiment with at least about 22 carbon atoms, in still another embodiment with at least about 24 carbon atoms, in another embodiment with at least about 26 carbon atoms, in yet another embodiment with at least about 28 carbon atoms, in still another embodiment with at least about 30 carbon atoms, in another embodiment with at least about 32 carbon atoms, in yet another embodiment with at least about 34 carbon atoms, and in still another embodiment with at least about 36 carbon atoms, and in one embodiment with no more than about 200 carbon atoms, in another embodiment with no more than about 100 carbon atoms, in yet another embodiment with no more than about 75 carbon atoms, in still another embodiment with no more than about 60 carbon atoms, in another embodiment with no more than about 50 carbon atoms, and in yet another embodiment with no more than about 40 carbon atoms, although the number of carbon atoms can be outside of these ranges, (ii) an aryl group (including unsubstituted and substituted aryl groups), in one embodiment with at least about 6 carbon atoms, in another embodiment with at least about 10 carbon atoms, in yet another embodiment with at least about 13 carbon atoms, in still another embodiment with at least about 14 carbon atoms, in another embodiment with at least about 16 carbon atoms, in yet another embodiment with at least about 17 carbon atoms, in still another embodiment with at least about 18 carbon atoms, in another embodiment with at least about 19 carbon atoms, in yet another embodiment with at least about 20 carbon atoms, in still another embodiment with at least about 21 carbon atoms, in another embodiment with at least about 22 carbon atoms, and in yet another embodiment with at least about 23 carbon atoms, and in one embodiment with no more than about 100 carbon atoms, in another embodiment with no more than about 75 carbon atoms, and in yet another embodiment with no more than about 50 carbon atoms, although the number of carbon atoms can be outside of these ranges, (iii) an arylalkyl group (including unsubstituted and substituted arylalkyl groups), in one embodiment with at least about 7 carbon atoms, in another embodiment with at least about 8 carbon atoms, in another embodiment with at least about 10 carbon atoms, in yet another embodiment with at least about 12 carbon atoms, in still another embodiment with at least about 14 carbon atoms, in another embodiment with at least about 16 carbon atoms, in yet another embodiment with at least about 18 carbon atoms, in still another embodiment with at least about 20 carbon atoms, in another embodiment with at least about 22 carbon atoms, in yet another embodiment with at least about 24 carbon atoms, in still another embodiment with at least about 26 carbon atoms, in another embodiment with at least about 28 carbon atoms, in yet another embodiment with at least about 30 carbon atoms, in still another embodiment with at least about 32 carbon atoms, in another embodiment with at least about 34 carbon atoms, in yet another embodiment with at least about 36 carbon atoms, in another embodiment with at least about 38 carbon atoms, in yet another embodiment with at least about 40 carbon atoms, and in still another embodiment with at least about 42 carbon atoms, and in one embodiment with no more than about 200 carbon atoms, in another embodiment with no more than about 100 carbon atoms, and in yet another embodiment with no more than about 44 carbon atoms, although the number of carbon atoms can be outside of these ranges, (iv) an alkylaryl group (including unsubstituted and substituted alkylaryl groups), in one embodiment with at least about 7 carbon atoms, in another embodiment with at least about 8 carbon atoms, in another embodiment with at least about 10 carbon atoms, in yet another embodiment with at least about 12 carbon atoms, in still another embodiment with at least about 14 carbon atoms, in another embodiment with at least about 16 carbon atoms, in yet another embodiment with at least about 18 carbon atoms, in still another embodiment with at least about 20 carbon atoms, in another embodiment with at least about 22 carbon atoms, in yet another embodiment with at least about 24 carbon atoms, in still another embodiment with at least about 26 carbon atoms, in another embodiment with at least about 28 carbon atoms, in yet another embodiment with at least about 30 carbon atoms, in still another embodiment with at least about 32 carbon atoms, in another embodiment with at least about 34 carbon atoms, in yet another embodiment with at least about 36 carbon atoms, in another embodiment with at least about 38 carbon atoms, in yet another embodiment with at least about 40 carbon atoms, and in still another embodiment with at least about 42 carbon atoms, and in one embodiment with no more than about 200 carbon atoms, in another embodiment with no more than about 100 carbon atoms, and in yet another embodiment with no more than about 44 carbon atoms, although the number of carbon atoms can be outside of these ranges, (v) an alkoxy group (including linear, branched, saturated, unsaturated, cyclic, unsubstituted, and substituted alkoxy groups, and wherein hetero atoms, such as oxygen, nitrogen, sulfur, silicon, phosphorus, and the like either may or may not be present in the alkyl portion of the alkoxy group), in one embodiment with at least 1 carbon atom, in another embodiment with at least about 8 carbon atoms, in yet another embodiment with at least about 10 carbon atoms, in still another embodiment with at least about 12 carbon atoms, in another embodiment with at least about 14 carbon atoms, in yet another embodiment with at least about 16 carbon atoms, in still another embodiment with at least about 18 carbon atoms, in another embodiment with at least about 20 carbon atoms, in yet another embodiment with at least about 22 carbon atoms, in still another embodiment with at least about 24 carbon atoms, in another embodiment with at least about 26 carbon atoms, in yet another embodiment with at least about 28 carbon atoms, in still another embodiment with at least about 30 carbon atoms, in another embodiment with at least about 32 carbon atoms, in yet another embodiment with at least about 34 carbon atoms, and in still another embodiment with at least about 36 carbon atoms, and in one embodiment with no more than about 200 carbon atoms, in another embodiment with no more than about 100 carbon atoms, in yet another embodiment with no more than about 75 carbon atoms, in still another embodiment with no more than about 60 carbon atoms, in another embodiment with no more than about 50 carbon atoms, and in yet another embodiment with no more than about 40 carbon atoms, although the number of carbon atoms can be outside of these ranges, (vi) an aryloxy group (including unsubstituted and substituted aryloxy groups), in one embodiment with at least about 6 carbon atoms, in another embodiment with at least about 10 carbon atoms, in yet another embodiment with at least about 13 carbon atoms, in still another embodiment with at least about 14 carbon atoms, in another embodiment with at least about 16 carbon atoms, in yet another embodiment with at least about 17 carbon atoms, in still another embodiment with at least about 18 carbon atoms, in another embodiment with at least about 19 carbon atoms, in yet another embodiment with at least about 20 carbon atoms, in still another embodiment with at least about 21 carbon atoms, in another embodiment with at least about 22 carbon atoms, and in yet another embodiment with at least about 23 carbon atoms, and in one embodiment with no more than about 100 carbon atoms, in another embodiment with no more than about 75 carbon atoms, and in yet another embodiment with no more than about 50 carbon atoms, although the number of carbon atoms can be outside of these ranges, (vii) an arylalkyloxy group (including unsubstituted and substituted arylalkyloxy groups), in one embodiment with at least about 7 carbon atoms, in another embodiment with at least about 8 carbon atoms, in another embodiment with at least about 10 carbon atoms, in yet another embodiment with at least about 12 carbon atoms, in still another embodiment with a least about 14 carbon atoms, in another embodiment with at least about 16 carbon atoms, in yet another embodiment with at least about 18 carbon atoms, in still another embodiment with at least about 20 carbon atoms, in another embodiment with at least about 22 carbon atoms, in yet another embodiment with at least about 24 carbon atoms, in still another embodiment with at least about 26 carbon atoms, in another embodiment with at least about 28 carbon atoms, in yet another embodiment with at least about 30 carbon atoms, in still another embodiment with at least about 32 carbon atoms, in another embodiment with at least about 34 carbon atoms, in yet another embodiment with at least about 36 carbon atoms, in another embodiment with at least about 38 carbon atoms, in yet another embodiment with at least about 40 carbon atoms, and in still another embodiment with at least about 42 carbon atoms, and in one embodiment with no more than about 200 carbon atoms, in another embodiment with no more than about 100 carbon atoms, and in yet another embodiment with no more than about 44 carbon atoms, although the number of carbon atoms can be outside of these ranges, (viii) an alkylaryloxy group (including unsubstituted and substituted alkylaryloxy groups), in one embodiment with at least about 7 carbon atoms, in another embodiment with at least about 8 carbon atoms, in another embodiment with at least about 10 carbon atoms, in yet another embodiment with at least about 12 carbon atoms, in still another embodiment with at least about 14 carbon atoms, in another embodiment with at least about 16 carbon atoms, in yet another embodiment with at least about 18 carbon atoms, in still another embodiment with at least about 20 carbon atoms, in another embodiment with at least about 22 carbon atoms, in yet another embodiment with at least about 24 carbon atoms, in still another embodiment with at least about 26 carbon atoms, in another embodiment with at least about 28 carbon atoms, in yet another embodiment with at least about 30 carbon atoms, in still another embodiment with at least about 32 carbon atoms, in another embodiment with at least about 34 carbon atoms, in yet another embodiment with at least about 36 carbon atoms, in another embodiment with at least about 38 carbon atoms, in yet another embodiment with at least about 40 carbon atoms, and in still another embodiment with at least about 42 carbon atoms, and in one embodiment with no more than about 200 carbon atoms, in another embodiment with no more than about 100 carbon atoms, and in yet another embodiment with no more than about 44 carbon atoms, although the number of carbon atoms can be outside of these ranges, (ix) a polyalkyleneoxy group, wherein the alkyl portion of the repeat alkyleneoxy groups typically has from about 1 to about 12 carbon atoms, although the number of carbon atoms can be outside of these ranges, such as a polyethyleneoxy group, a polypropyleneoxy group, a polybutyleneoxy group, or the like, and wherein the number of repeat alkyleneoxy groups typically is from about 2 to about 50 repeat alkyleneoxy groups, although the number of repeat units can be outside of these ranges, (x) a polyaryleneoxy group, wherein the aryl portion of the repeat aryleneoxy groups typically has from about 6 to about 14 carbon atoms, although the number of carbon atoms can be outside of these ranges, such as a polyphenyleneoxy group, a polynaphthaleneoxy group, a polyphenanthreneoxy group, or the like, and wherein the number of repeat aryleneoxy groups typically is from about 2 to about 20 repeat aryleneoxy groups, although the number of repeat units can be outside of these ranges, (xi) a polyarylalkyleneoxy group, wherein the arylalkyl portion of the repeat arylalkyleneoxy groups typically has from about 7 to about 50 carbon atoms, although the number of carbon atoms can be outside of these ranges, such as a polybenzyleneoxy group, a polyphenylethyleneoxy group, or the like, and wherein the number of repeat arylalkyleneoxy groups typically is from about 2 to about 20 repeat arylalkyleneoxy groups, although the number of repeat units can be outside of these ranges, (xii) a polyalkylaryleneoxy group, wherein the alkylaryl portion of the repeat alkylaryleneoxy groups typically has from about 7 to about 50 carbon atoms, although the number of carbon atoms can be outside of these ranges, such as a polytolueneoxy group or the like, and wherein the number of repeat alkylaryleneoxy groups typically is from about 2 to about 20 repeat alkylaryleneoxy groups, although the number of repeat units can be outside of these ranges, (xiii) a heterocyclic group (including unsubstituted and substituted heterocyclic groups), typically with from about 2 to about 12 carbon atoms, and typically with from about 4 to about 18 ring atoms, although the number of carbon atoms and the number of ring atoms can be outside of these ranges, wherein the heteroatoms in the heterocyclic groups can be (but are not limited to) nitrogen, oxygen, sulfur, silicon, phosphorus, and the like, as well as mixtures thereof, (xiv) a silyl group (including unsubstituted and substituted silyl groups), (xv) a siloxane group (including unsubstituted and substituted siloxane groups), (xvi) a polysilylene group (including unsubstituted and substituted polysilylene groups), typically with from 2 to about 100 repeat silylene units, or (xvii) a polysiloxane group (including unsubstituted and substituted polysiloxane groups), typically with from 2 to about 200 repeat siloxane units, although the number of repeat siloxane units can be outside of this range, wherein the substituents on the substituted alkyl, aryl, arylalkyl, alkylaryl, alkoxy, aryloxy, arylalkyloxy, alkylaryloxy, polyalkyleneoxy, polyaryleneoxy, polyarylalkyleneoxy, polyalkylaryleneoxy, heterocyclic, silyl, siloxy, polysilylene, and polysiloxy groups are hydroxy groups, halogen atoms, cyano groups, ether groups, aldehyde groups, ketone groups, carboxylic acid groups, ester groups, amide groups, carbonyl groups, thiocarbonyl groups, sulfate groups, sulfonate groups, sulfide groups, sulfoxide groups, phosphate groups, nitrile groups, mercapto groups, nitro groups, nitroso groups, sulfone groups, acyl groups, acid anhydride groups, azide groups, cyanato groups, isocyanato groups, thiocyanato groups, isothiocyanato groups, mixtures thereof, and the like, wherein the substituents on the silylene, siloxy, polysilylene, and polysiloxy groups can also be alkyl groups, aryl groups, arylalkyl groups, and alkylaryl groups, wherein two or more substituents can be joined together to form a ring, and wherein $R_{20}$ and $R_2'$ con be the same as each other or different from each other.

Some specific examples of suitable $R_{20}$ and $R_{20}'$ groups include (but are not limited to) methyl, of the formula —$CH_3$, ethyl, of the formula —$C_2H_5$, n-octyl, of the formula —$(CH_2)_7CH_3$, stearyl, of the formula —$(CH_2)_{17}CH_3$, menthyl, of the formula

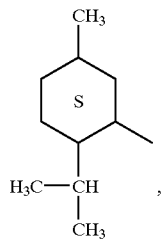

wherein the "S" indicates that the ring is saturated as opposed to being aromatic, branched saturated hydrocarbon groups containing 18 carbon atoms, of the general formula

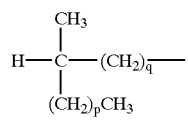

wherein q is an integer of from about 10 to about 15, p is an integer of from 0 to about 3, and the sum of p+q=15, such as isostearyl, oleyl, of the formula

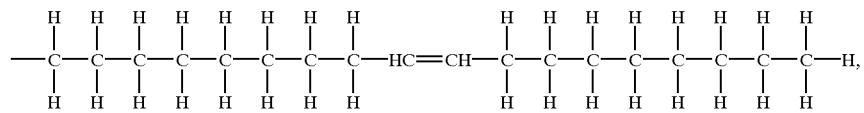

2-octyldodecyl, of the formula

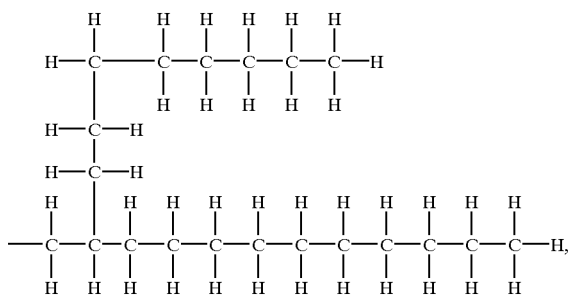

cholesteryl, of the formula

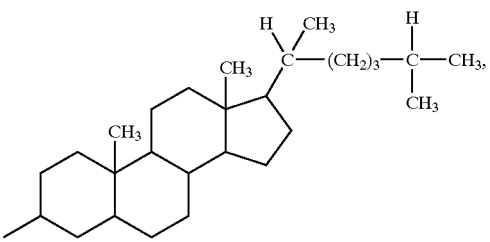

abietyl, including groups of the formula

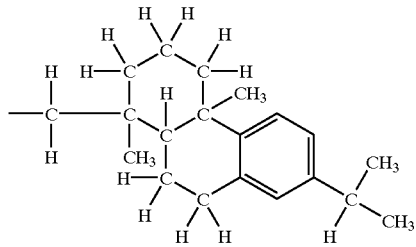

as well as hydrogenated and dehydrogenated isomers of the above formula that are also derivatives of the rosin-derived natural product abietic acid, such as didehydroabietyl and the like, 2-ethylhexyl, of the formula

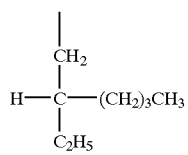

(1-oxypropyl)-2-octyldodecane, of the formula

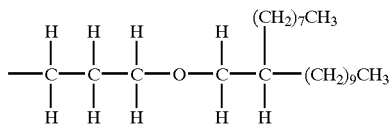

and the like.

X and X' and Z and Z' have the same definitions previously provided.

These compounds can be prepared by a similar process to that described hereinabove for a reaction between a pyridone and a dianiline but with the stoichiometry modified appropriately.

Precursor anilines and dianilines can be prepared by any desired or effective method, such as that disclosed in, for example, "The Chemistry of Isatoic Anhydride," G. M. Coppola, *Synthesis*, p. 505 (1980); "Isatoic Anhydride. IV. Reactions with Various Nucleophiles," R. P. Staiger et al., *J. Org. Chem.*, Vol. 24, p. 1214 (1959); R. P. Staiger et al., *J. Chem. Eng.* Data B, p. 454 (1963): and U.S. Pat. No. 4,016,143; the disclosures of each of which are totally incorporated herein by reference.

Specific embodiments of the invention will now be described in detail. These examples are intended to be illustrative, and the invention is not limited to the materials, conditions, or process parameters set forth in these embodiments. All parts and percentages are by weight unless otherwise indicated.

EXAMPLE I

Into a 2 liter round-bottom flask equipped with mechanical stirrer and Dean Stark trap was charged melted dodecylamine (185.0 grams, 1.0 mol; melting point 30 to 32° C.; obtained. from Akzo Nobel Chemicals, Mississauga, Ontario) followed with ethyl cyanoacetate (135.6 grams, 1.2 mol, density 1.06 grams per milliliter; obtained from Spectrum Chemicals, New Brunswick, N.J.). The colorless mixture thus formed was stirred and then heated to 120° C. for a period of 1 hour, during which time a by-product formed and was allowed to distill away.

To the hot reaction mixture stirring at 120° C. internal temperature was then sequentially added a dimethylformamide solvent (320 grams; obtained from Caledon Labs, Brampton, Ontario), ethyl acetoacetate (260.0 grams, 2.0 mol, density 1.02 grams per milliliter; obtained from Lonza Group, Germany), and piperazine (192.2 grams, 2.0 mol; obtained from Spectrum Chemicals, New Brunswick, N.J.). The mixture thus formed was re-heated to 110° C. for a period of 4 hours, during which time more by-product was distilled off. The resulting golden brown solution was then allowed to cool to room temperature.

The golden brown solution was then carefully poured, with vigorous stirring, into a prepared room temperature solution of methanol (1,624 grams), deionized water (684 grams), and concentrated nitric acid (322 grams, 3.6 mol). A solid beige precipitate formed almost at once, and the resulting slurry was stirred for 30 minutes. The slurry was then vacuum filtered in a 26 centimeter Buchner funnel, and the solid coke was rinsed in the funnel with 500 milliliter portions of a solvent mixture containing 70 percent by volume methanol and 30 percent by volume water until the conductivity of the filtrate was low. The solid was dried at 40° C. under vacuum for 24 hours to give the dodecyl pyridone product as a light beige solid (yield 277 grams; 87 percent). $^1$H-NMR spectral analysis indicated that the product was of high purity, with no evidence of contaminants exceeding approximately 2 percent of the product yield.

$^1$H-NMR spectral assignments (300 MHz, DMSO-d$_6$): 5.6 ppm (singlet, H at ring position C-5), 3.88 ppm (broad triplet, 2H, CH$_2$ adjacent ring N), 2.2 ppm (singlet, 3H, CH$_3$ at ring position C-4), 1.6 ppm to 0.8 ppm (CH$_2$ and CH$_3$ protons from dodecyl group, 3 signals totaling 65H integration).

EXAMPLE II

Into a 12 liter round-bottom flask equipped with mechanical stirrer and Dean Stark trap was charged melted dodecylamine (756.4 grams, 4.08 mol; melting point 30 to 32° C.; obtained from Akzo Nobel Chemicals, Mississauga, Ontario) followed with ethyl cyanoacetate (470.7 grams, 4.16 mol, density 1.06 grams per milliliter; obtained from Spectrum Chemicals, New Brunswick, N.J.). The colorless mixture thus formed was stirred and then heated to 120° C. for a period of 1 hour, during which time a by-product formed and was allowed to distill away.

To the hot reaction mixture stirring at 120° C. internal temperature was then sequentially added a dimethylformamide solvent (1,300 grams; obtained from Caledon Labs, Brampton, Ontario), ethyl acetoacetate (1,062 grams, 8.16 mol, density 1.02 grams per milliliter; obtained from Lonza Group, Germany), and piperazine (702.9 grams, 8.16 mol; obtained from Spectrum Chemicals, New Brunswick, N.J.). The mixture thus formed was re-heated to 140° C. for a period of 2 hours, during which time more by-product was distilled off. The resulting golden brown solution was then allowed to cool to room temperature.

The golden brown solution was then carefully poured, with vigorous stirring, into a prepared room temperature solution of methanol (4,330 grams), deionized water (5,474 grams), and concentrated nitric acid (1,149 grams, 12.6 mol). A solid beige precipitate formed almost at once, and the resulting slurry was stirred for 30 minutes. The slurry was then vacuum filtered in a 14 inch funnel. This filtration was very slow, requiring more than 4 hours to complete. The solid cake was then rinsed in the funnel with 2 liter portions of a solvent mixture containing 75 percent by volume methanol and 25 percent by volume water until the conductivity of the filtrate was low. The solid was dried at 40° C. under vacuum for 24 hours to give the dodecyl pyridone product as a light beige solid (yield 1,088 grams; 85 percent). $^1$H-NMR spectral analysis indicated that the product was of high purity, with no evidence of contaminants exceeding approximately 2 percent of the product yield.

EXAMPLE III

Into a 12 liter round-bottom flask equipped with mechanical stirrer and Dean Stark trap was charged melted dodecylamine (741.6 grams, 4.0 mol; melting point 30 to 32° C.; obtained from Akzo Nobel Chemicals, Mississauga, Ontario) followed with ethyl cyanoacetate (461.4 grams, 4.08 mol, density 1.06 grams per milliliter; obtained from Spectrum Chemicals, New Brunswick, N.J.). The colorless mixture thus formed was stirred and then heated to 120° C. for a period of 1 hour, during which time a by-product formed and was allowed to distill away.

To the hot reaction mixture stirring at 120° C. internal temperature was then sequentially added a dimethylformamide solvent (1,275 grams), ethyl acetoacetate (1,041.2 grams, 8.0 mol, density 1.02 grams per milliliter; obtained from Lonza Group, Germany), 15 and piperazine (689.1 grams, 8.0 mol; obtained from Spectrum Chemicals, New Brunswick, N.J.). The mixture thus formed was re-heated to 140° C. for a period of 2 hours, during which time more by-product was distilled off. The resulting golden brown solution was then allowed to cool to room temperature.

The golden brown solution was then carefully poured, with vigorous stirring, into a prepared room temperature solution of methanol (6,494 grams), deionized water (2,737 grams), and concentrated nitric acid (1,149 grams, 12.6 mol). A solid beige precipitate formed almost at once, and the resulting slurry was stirred for 30 minutes. The slurry was then vacuum filtered in a 14 inch funnel, and the solid cake was then rinsed in the funnel with 2 liter portions of a solvent mixture containing 75 percent by volume methanol and 25 percent by volume water until the conductivity of the filtrate was low. The solid was dried at 40° C. under vacuum for 24 hours to give the dodecyl pyridone product as a light beige solid (yield 951 grams; 75 percent). $^1$H-NMR spectral analysis indicated that the product was of high purity, with no evidence of contaminants exceeding approximately 2 percent of the product yield.

EXAMPLE IV

Into a 1 liter round-bottom flask equipped with mechanical stirrer and Dean Stark trap was charged melted dodecylamine (92.6 grams, 0.5 mol; melting point 30 to 32° C.; obtained from Akzo Nobel Chemicals, Mississauga, Ontario) followed with ethyl cyanoacetate (67.8 grams, 0.6 mol, density 1.06 grams per milliliter; obtained from Spectrum Chemicals, New Brunswick, N.J.). The colorless mixture thus formed was stirred and then heated to 120° C. for a period of 1 hour, during which time a by-product formed and was allowed to distill away.

To the hot reaction mixture stirring at 120° C. internal temperature was then sequentially added a toluene solvent (160 grams; obtained from Caledon Labs, Brampton, Ontario), ethyl acetoacetate (130.0 grams, 1.0 mol, density 1.02 grams per milliliter; obtained from Lonza Group, Germany), and piperazine (86.2 grams, 1.0 mol; obtained from Spectrum Chemicals, New Brunswick, N.J.). The mixture thus formed was re-heated to 110° C. for a period of 4 hours, during which time more by-product was distilled off. The resulting golden brown solution was then allowed to cool to room temperature.

The golden brown solution was then carefully poured, with vigorous stirring, into a prepared room temperature solution of methanol (812 grams), deionized water (342 grams), and concentrated nitric acid (162 grams, 1.8 mol). A solid beige precipitate formed almost at once, and the resulting slurry was stirred for 30 minutes. The slurry was then vacuum filtered in a 25 centimeter Buchner funnel, and the solid cake was rinsed in the funnel with 500 milliliter portions of a solvent mixture containing 50 percent by volume methanol and 50 percent by volume water until the conductivity of the filtrate was low. The solid was dried at 40° C. under vacuum for 24 hours to give the dodecyl pyridone product as a light beige solid (yield 128.8 grams; 81 percent). $^1$H-NMR spectral analysis indicated that the product was of high purity, with no evidence of contaminants exceeding approximately 2 percent of the product yield.

EXAMPLE V

Into a 2 liter round-bottom flask equipped with mechanical stirrer and Dean Stark trap was charged octylamine (194 grams, 1.5 mol; obtained from Aldrich Chemicals, Oakville, Ontario) followed with ethyl cyanoacetate (203 grams, 1.8 mol; obtained from Spectrum Chemicals, New Brunswick, N.J.). The mixture thus formed was stirred and then heated to 140° C. for a period of 1 hour, during which time a by-product formed and was allowed to distill away.

To the hot reaction mixture stirring at 140° C. internal temperature was then sequentially added a dimethylformamide solvent (375 milliliters; obtained from Caledon Labs, Brampton, Ontario), ethyl acetoacetate (390 grams, 3.0 mol; obtained from Lonza Group, Germany), and piperazine (258 grams, 3.0 mol; obtained from Spectrum Chemicals, New Brunswick, N.J.). The mixture thus formed was re-heated to 110° C. for a period of 4 hours, during which time more ethanol by-product was distilled off. The resulting solution was then allowed to cool to room temperature.

The solution was then carefully poured, with vigorous stirring, into a prepared room temperature solution of methanol (2 liters), deionized water (2 liters), and concentrated nitric acid (448 grams, 5 mol). A solid beige precipitate formed almost at once, and the resulting slurry was stirred for 30 minutes. The slurry was then vacuum filtered in an 18.5 centimeter funnel, and the solid cake was rinsed in the funnel with 1 liter portions of a solvent mixture containing 50 percent by volume methanol and 50 percent by volume water. The solid was dried at 40° C. under vacuum for 24 hours to give the octyl pyridone product as a light beige solid (yield 343 grams; 87 percent). $^1$H-NMR spectral analysis indicated that the product was of high purity, with no evidence of contaminants exceeding approximately 2 percent of the product yield.

EXAMPLE VI

Into a 2 liter round-bottom flask equipped with mechanical stirrer and Dean Stark trap was charged 1,12-diaminododecane (100.1 grams, 0.5 mol; obtained from Aldrich Chemicals, Oakville, Ontario) followed with ethyl cyanoacetate (135.5 grams, 1.2 mol; obtained from Spectrum Chemicals, New Brunswick, N.J.). The mixture thus formed was stirred and then heated to 150° C. for a period of 1 hour, during which time a by-product formed and was allowed to distill away.

To the hot reaction mixture stirring at 150° C. internal temperature was then sequentially added a dimethylformamide solvent (300 milliliters; obtained from Caledon Labs, Brampton, Ontario), ethyl acetoacetate (325 grams, 2.5 mol; obtained from Lonza Group, Germany), and piperazine (172 grams, 2.0 mol; obtained from Spectrum Chemicals, New Brunswick, N.J.). The mixture thus formed was re-heated to 120° C. for a period of 4 hours, during which time more by-product was distilled off. The resulting solution was then allowed to cool to room temperature.

The solution was then carefully poured, with vigorous stirring, into a prepared room temperature solution of methanol (1.5 liter), deionized water (500 milliliters), and concentrated nitric acid (360 grams, 4 mol). A solid beige precipitate formed almost at once, and the resulting slurry was stirred for 30 minutes. The slurry was then vacuum filtered in an 18.5 centimeter funnel, and the solid cake was rinsed in the funnel with 1 liter portions of a solvent mixture containing 75 percent by volume methanol and 25 percent by volume water. The solid was dried at 40° C. under vacuum for 24 hours to give the dipyridone product as a light beige solid (yield 183 grams; 79 percent). $^1$H-NMR spectral analysis indicated that the product was of high purity, with no evidence of contaminants exceeding approximately 2 percent of the product yield.

EXAMPLE VII

Into a 2 liter round-bottom flask equipped with mechanical stirrer and Dean Stark trap was charged 4-(aminomethyl)-1,8-diaminooctane (86.7 grams, 0.5 mol; obtained from Aldrich Chemicals, Oakville, Ontario) followed with ethyl cyanoacetate (186.5 grams, 1.65 mol; obtained from Spectrum Chemicals, New Brunswick, N.J.). The mixture thus formed was stirred and then heated to 120° C. for a period of 1 hour, during which time a by-product formed and was allowed to distill away.

To the hot reaction mixture stirring at 120° C. internal temperature was then sequentially added ethyl acetoacetate (599 grams, 4.5 mol; obtained from Lonza Group, Germany) and piperazine (258 grams, 3.0 mol; obtained from Spectrum Chemicals, New Brunswick, N.J.). The mixture thus formed was re-heated to 110° C. for a period of 3 hours, during which time more by-product was distilled off. The resulting solution was then allowed to cool to room temperature.

The solution was then carefully poured, with vigorous stirring, into a prepared room temperature solution of methanol (1.2 liter), deionized water (1.4 liters), and concentrated nitric acid (590 grams, 6.5 mol). A solid beige precipitate formed almost at once, and the resulting slurry was stirred for 30 minutes. The slurry was then vacuum filtered in an 18.5 centimeter funnel, and the solid cake was rinsed in the funnel with 1 liter portions of a solvent mixture containing 75 percent by volume methanol and 25 percent by volume water. The solid was dried at 40° C. under vacuum for 24 hours to give the tripyridone product as a light beige solid (yield 131 grams; 46 percent). $^1$H-NMR spectral analysis indicated that the product was of high purity, with no evidence of contaminants exceeding approximately 2 percent of the product yield.

EXAMPLE VIII

Into a 1 liter round-bottom flask equipped with mechanical stirrer and Dean Stark trap was charged melted dodecylamine (94.5 grams, 0.51 mol; melting point 30 to 32° C.; obtained from Akzo Nobel Chemicals, Mississauga, Ontario) followed with ethyl cyanoacetate (56.5 grams, 0.5 mol, density 1.06 grams per milliliter; obtained from Spectrum Chemicals, New Brunswick, N.J.). The colorless mixture thus formed was stirred and then heated to 120° C. for a period of 1 hour, during which time a by-product formed and was allowed to distill away.

To the hot reaction mixture stirring at 120° C. internal temperature was then sequentially added a dimethylformamide solvent (160 grams; obtained from Caledon Labs, Brampton, Ontario), ethyl acetoacetate (78.0 grams, 0.6 mol, density 1.02 grams per milliliter; obtained from Lonza Group, Germany), and piperazine (51.7 grams, 0.6 mol; obtained from Spectrum Chemicals, New Brunswick, N.J.). The mixture thus formed was re-heated to 140° C. for a period of 2 hours, during which time more by-product was distilled off. The resulting golden brown solution was then allowed to cool to room temperature.

The golden brown solution was then carefully poured, with vigorous stirring, into a prepared room temperature solution of methanol (812 grams), deionized water (342 grams), and concentrated hydrochloric acid (159 grams, 1.8 mol). A solid beige precipitate formed almost at once, and the resulting slurry was stirred for 30 minutes. The slurry was then vacuum filtered in a 26 centimeter Buchner tunnel, and the solid cake was rinsed in the funnel with 500 milliliter portions of a solvent mixture containing 75 percent by volume methanol and 25 percent by volume water until the conductivity of the filtrate was low. The solid was dried at 40° C. under vacuum for 24 hours to give the dodecyl pyridone product as a light beige solid (yield 110.3 grams; 69 percent). $^1$H-NMR spectral analysis indicated that the product was of high purity, with no evidence of contaminants exceeding approximately 2 percent of the product yield.

EXAMPLE IX

Into a 1 liter round-bottom flask equipped with mechanical stirrer and Dean Stark trap was charged melted dodecylamine (92.6 grams, 0.5 mol; melting point 30 to 32° C.; obtained from Akzo Nobel Chemicals, Mississauga, Ontario) followed with ethyl cyanoacetate (57.6 grams, 0.51 mol, density 1.06 grams per milliliter; obtained from Spectrum Chemicals, New Brunswick, N.J.). The colorless mixture thus formed was stirred and then heated to 120° C. for a period of 1 hour, during which time a by-product formed and was allowed to distill away.

To the hot reaction mixture stirring at 120° C. internal temperature was then sequentially added a toluene solvent (160 grams; obtained from Caledon Labs, Brampton, Ontario), ethyl acetoacetate (66.3 grams, 0.51 mol, density 1.02 grams per milliliter; obtained from Lonza Group, Germany), and piperazine (43.9 grams, 0.51 mol; obtained from Spectrum Chemicals, New Brunswick, N.J.). The mixture thus formed was re-heated to 110° C. for a period of 4 hours, during which time more by-product was distilled off. The resulting golden brown solution was then allowed to cool to room temperature.

The golden brown solution was then carefully poured, with vigorous stirring, into a prepared room temperature solution of methanol (812 grams), deionized water (342 grams), and concentrated nitric acid (162 grams, 1.8 mol). A solid beige precipitate formed almost at once, and the resulting slurry was stirred for 30 minutes. The slurry was then vacuum filtered in a 25 centimeter Buchner funnel, and the solid cake was rinsed in the funnel with 500 milliliter portions of a solvent mixture containing 50 percent by volume methanol and 50 percent by volume water until the conductivity of the filtrate was low. The solid was dried at 40° C. under vacuum for 24 hours to give the dodecyl pyridone product as a light beige solid (yield 118 grams; 74 percent). $^1$H-NMR spectral analysis indicated that the product was of high purity, with no evidence of contaminants exceeding approximately 2 percent of the product yield.

EXAMPLE X

Into a 1 liter round-bottom flask equipped with mechanical stirrer and Dean Stark trap was charged melted dodecylamine (94.5 grams, 0.51 mol; melting point 30 to 32° C.; obtained from Akzo Nobel Chemicals, Mississauga, Ontario) followed with ethyl cyanoacetate (56.5 grams, 0.5 mol, density 1.06 grams per milliliter: obtained from Spectrum Chemicals, New Brunswick, N.J.). The colorless mixture thus formed was stirred and then heated to 120° C. for a period of 1 hour, during which time a by-product formed and was allowed to distill away.

To the hot reaction mixture stirring at 120° C. internal temperature was then sequentially added a dimethylformamide solvent (160 grams), obtained from Caledon Labs, Brampton, Ontario), ethyl acetoacetate (130.1 grams, 1.0 mol, density 1.02 grams per milliliter; obtained from Lonza Group, Germany), and piperidine (85.0 grams, 1.0 mol; obtained from Aldrich Chemicals, Oakville, Ontario). The mixture thus formed was re-heated to 140° C. for a period of 2 hours, during which time more by-product was distilled off. The resulting golden brown solution was then allowed to cool to room temperature.

The golden brown solution was then carefully poured, with vigorous stirring, into a prepared room temperature solution of methanol (812 grams), deionized water (342 grams), and concentrated nitric acid (162 grams, 1.8 mol). A solid beige precipitate formed almost at once, and the resulting slurry was stirred for 30 minutes. The slurry was then vacuum filtered in a 25 centimeter Buchner funnel, and the solid coke was rinsed in the funnel with 500 milliliter portions of a solvent mixture containing 75 percent by volume methanol and 25 percent by volume water until the conductivity of the filtrate was low. The solid was dried at 40° C. under vacuum for 24 hours to give the dodecyl pyridone product as a light beige solid (yield 101.3 grams; 64 percent). $^1$H-NMR spectral analysis indicated that the product was of high purity, with no evidence of contaminants exceeding approximately 2 percent of the product yield.

EXAMPLE XI

Into a 1 liter round-bottom flask equipped with mechanical stirrer and Dean Stark trap was charged melted stearylamine (135.0 grams, 0.5 mol; obtained from Aldrich Chemical, Oakville, Ontario) followed with ethyl cyanoacetate (67.8 grams, 0.6 mol, density 1.06 grams per milliliter; obtained from Spectrum Chemicals, New Brunswick, N.J.). The mixture thus formed was stirred and then heated to 120° C. for a period of 1 hour, during which time a by-product formed and was allowed to distill away.

To the hot reaction mixture stirring at 120° C. internal temperature was then sequentially added a dimethylformamide solvent (190 grams; obtained from Caledon Labs, Brampton, Ontario), ethyl acetoacetate (130.0 grams, 1.0 mol, density 1.02 grams per milliliter; obtained from Lonza Group, Germany), and piperazine (86.2 grams, 1.0 mol; obtained from Spectrum Chemicals, New Brunswick, N.J.). The mixture thus formed was re-heated to 120° C. for a period of 6 hours, during which time more by-product was distilled off. The resulting solution was then allowed to cool to room temperature.

The solution was then carefully poured, with vigorous stirring, into a prepared room temperature solution of methanol (1,975 grams) and concentrated nitric acid (180 grams, 2.0 mol). A solid beige precipitate formed almost at once, and the resulting slurry was stirred for 30 minutes. The slurry was then vacuum filtered in a 25 centimeter Buchner funnel, and the solid cake was rinsed in the funnel with 500 milliliter portions of a solvent mixture containing 50 percent by volume methanol and 50 percent by volume water until the conductivity of the filtrate was low. The solid was dried at 60° C. for 48 hours to give the stearyl pyridone product as a light beige solid (yield 169.5 grams; 84 percent). $^1$H-NMR spectral analysis indicated that the product was of high purity, with no evidence of contaminants exceeding approximately 2 percent of the product yield.

COMPARATIVE EXAMPLE A

Into a 250 milliliter round-bottom flask equipped with mechanical stirrer and Dean Stark trap was charged melted dodecylamine (14.15 grams, 0.0765 mol; melting point 30 to 32° C.; obtained from Akzo Nobel Chemicals, Mississauga, Ontario) followed with ethyl cyanoacetate (8.48 grams, 0.075 mol, density 1.06 grams per milliliter; obtained from Spectrum Chemicals, New Brunswick, N.J.), followed with a dimethylformamide solvent (23.9 grams; obtained from Caledon Labs, Brampton, Ontario), ethyl acetoacetate (39.0 grams, 0.3 mol, density 1.02 grams per milliliter; obtained from Lonza Group, Germany), and piperidine (25.55 grams, 0.3 mol; obtained from Aldrich Chemicals, Oakville, Ontario). The mixture was heated to 110° C. for a period of 4 hours, during which time a by-product was distilled off. The resulting solution was then allowed to cool to room temperature.

The solution was then carefully poured, with vigorous stirring, into a prepared room temperature solution of methanol (95 grams), deionized water (20 grams), and concentrated hydrochloric acid (48 grams, 0.47 mol). A solid beige precipitate formed almost at once, and the resulting slurry was stirred for 30 minutes. The slurry was then vacuum filtered in a 25 centimeter Buchner funnel, and the solid cake was rinsed in the funnel with 250 milliliter portions of a solvent mixture containing 80 percent by volume methanol and 20 percent by volume water until the conductivity of the filtrate was low. The solid was dried at 40° C. under vacuum for 24 hours to give the dodecyl pyridone product as a light beige solid (yield 4.5 grams; 19 percent). $^1$H-NMR spectral analysis indicated that the product was of high purity, with no evidence of contaminants exceeding approximately 2 percent of the product yield.

COMPARATIVE EXAMPLE B

Into a 500 milliliter round-bottom flask equipped with mechanical stirrer and Dean Stark trap was charged melted dodecylamine (92.6 grams, 0.5 mol; melting point 30 to 32° C.; obtained from Akzo Nobel Chemicals, Mississauga, Ontario) followed with ethyl cyanoacetate (56.56 grams, 0.5 mol, density 1.06 grams per milliliter; obtained from Spectrum Chemicals, New Brunswick, N.J.) followed with the solvent ethanol (50 milliliters; obtained from Caledon Labs, Brampton, Ontario), ethyl acetoacetate (65.07 grams, 0.5 mol, density 1.02 grams per milliliter; obtained from Lonza Group, Germany), and piperidine (12.9 grams, 0.15 mol; obtained from Aldrich Chemicals, Oakville, Ontario). The mixture was heated to reflux for a period of 4 hours. The resulting light orange solution was then allowed to cool to room temperature, and the ethanol solvent removed by rotary evaporation.

The solution was then carefully poured, with vigorous stirring, into a cold solution, about 2° C., of 10 percent aqueous hydrochloric acid. A white precipitate formed almost at once, and the resulting slurry was stirred for 30 minutes. The slurry was then vacuum filtered in a 25 centimeter Buchner funnel, and the solid cake was rinsed in the funnel with 1 liter portions of a solvent mixture containing 50 percent by volume methanol and 50 percent by volume water until the conductivity of the filtrate was low. The solid was dried at 40° C. under vacuum for 24 hours to give the dodecyl pyridone product as a white solid (yield 40.6 grams; 25 percent). $^1$H-NMR spectral analysis indicated that the product was of low purity, with evidence of contaminants exceeding approximately 25 percent of the product yield.

COMPARATIVE EXAMPLE C

Into a 2 liter round-bottom flask equipped with mechanical stirrer and Dean Stark trap was charged melted dodecylamine (185.0 grams, 1.0 mol; melting point 30 to 32° C.; obtained from Akzo Nobel Chemicals, Mississauga, Ontario) followed with ethyl cyanoacetate (135.6 grams, 1.2 mol, density 1.06 grams per milliliter; obtained from Spectrum Chemicals, New Brunswick, N.J.), and a dimethylformamide solvent (300 milliliters; obtained from Caledon Labs, Brampton, Ontario). The mixture thus formed was stirred and then heated to 110° C. for a period of 1 hour, during which time a by-product formed and was allowed to distill away.

To the hot reaction mixture stirring at 110° C. internal temperature was then sequentially added ethyl acetoacetate (390.0 grams, 3.0 mol, density 1.02 grams per milliliter; obtained from Lonza Group, Germany), and piperazine (192.2 grams, 2.0 mol; obtained from Spectrum Chemicals, New Brunswick, N.J.). The mixture thus formed was re-heated to 110° C. for a period of 2.5 hours, during which time more by-product was distilled off. The resulting solution was then allowed to cool to room temperature.

The solution was then carefully poured, with vigorous stirring, into a prepared room temperature solution of methanol (1,659 grams), deionized water (700 grams), and concentrated nitric acid (274 rams, 3.0 mol). A solid beige precipitate formed almost at once, and the resulting slurry was stirred for 30 minutes. The slurry was then vacuum filtered in a 26 centimeter Buchner funnel, and the solid cake was rinsed in the funnel with 1 liter portions of a solvent mixture containing 75 percent by volume methanol and 25 percent by volume water until the conductivity of the filtrate was low. The solid was dried at 40° C. under vacuum for 24 hours to give the dodecyl pyridone product as a light beige solid (yield 253.6 grams; 79 percent). $^1$H-NMR spectral analysis indicated that the product was of low purity, with evidence of contaminants exceeding approximately 25 percent of the product yield.

EXAMPLE XII

A colorant of the formula

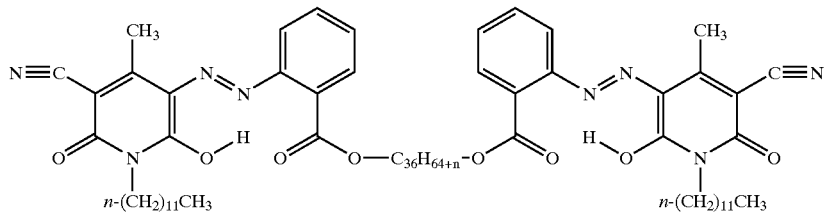

wherein $C_{36}H_{64+n}$ was a branched alkylene group which may include unsaturations and cyclic groups, wherein n is an integer of 0, 1, 2, 3, 4, 5, 6, 7, 8, 9, or 10, and wherein one isomer thereof was of the formula

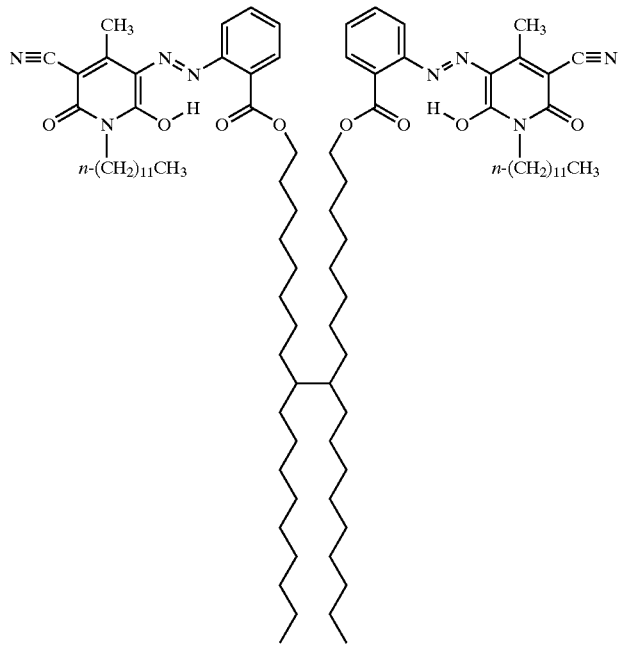

was prepared as follows.

A dimer ester anthranilate of the formula

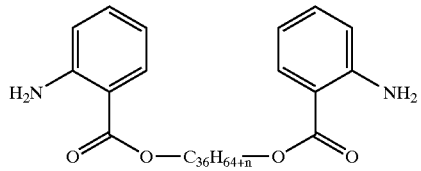

wherein $C_{36}H_{64+n}$ was a branched alkylene group which may include unsaturations and cyclic groups, wherein n is an integer of 0, 1, 2, 3, 4, 5, 6, 7, 8, 9, or 10, and wherein one isomer thereof was of the formula

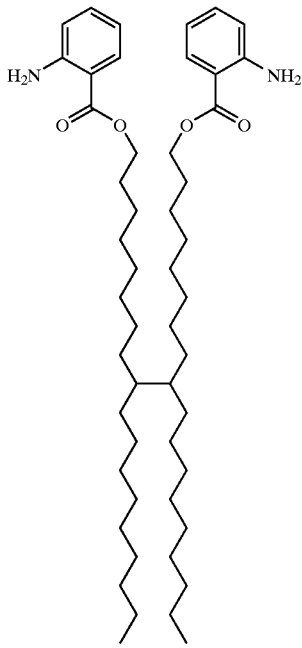

was prepared as follows. Into a 3 liter kettle equipped with a mechanical stirrer, water condenser, and thermometer was sequentially charged: isatoic anhydride (203.9 grams, 1.25 mol; obtained from Sigma-Aldrich, Milwaukee, Wis.), PRI-POL® 2033 (C-36 dimer diol mixture including isomers of the formula

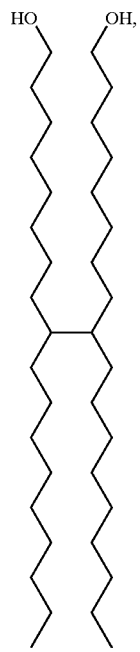

as well as other branched isomers which may include unsaturations and cyclic groups; 267 grams, 0.5 mol, obtained from Uniqema, New Castle, Del.; further information on C36 dimer diols of this type is disclosed in, for example, "Dimer Acids," *Kirk-Othmer Encyclopedia of Chemical Technology*, Vol. 8, 4$^{th}$ Ed. (1992), pp. 223 to 237, the disclosure of which is totally incorporated herein by reference), 1,4-diazabicyclo[2.2.2]octane (28 grams, 0.25 mol; obtained from Sigma-Aldrich Co.), and toluene (750 milliliters). The heterogeneous mixture thus formed was heated to 115° C. (internal temperature). During the ensuing reaction, evolution of gaseous $CO_2$ byproduct was observed. After approximately 3 hours of heating time, the reaction was complete. The mixture was cooled to room temperature and a 1.0 Molar aqueous solution of sodium hydroxide (500 milliliters, 0.5 mol) was added to the mixture. The mixture was divided into two 2 liter separatory funnels. Into each funnel was added ethyl acetate (350 milliliters), followed by the addition of brine (saturated aqueous sodium chloride) solution whereby the volume ratio of organic phase to aqueous phase was about 2 to 1. The organic phase was washed with 5×300 milliliter aliquots of brine solution until the pH was neutral. The organic layer extracts obtained were combined, dried over anhydrous $MgSO_4$ powder, and then filtered. The solvents were removed by distillation in vacuo with a rotary evaporator, giving an amber-colored viscous oil which was subsequently dried under high vacuum to give 372 grams (96 percent yield) of product. The purity of the dimer ester anthranilate product was observed to be very high by $^1$H-NMR spectroscopy, estimated at 97 percent, with 3 percent attributed to residual toluene solvent. $^1$H-NMR spectral assignments (300 MHz, $CDCl_3$): 7.85 ppm (doublet, 2H integration), 7.22 ppm (triplet, 2H), 6.60 ppm (superimposed doublet+triplet, 4H), 5.7 ppm (broad singlet), 4.25 ppm (triplet, $CH_2OC=O$, 4H), 1.75 ppm to 0.8 ppm (aliphatic CH, $CH_2$, $CH_3$ protons, 3 signals totaling 80H integration).

Into a 2 liter round-bottom flask equipped with mechanical stirrer and Dean Stark trap was charged melted dodecylamine (185.0 grams, 1.0 mol; melting point 30 to 32° C.; obtained from Akzo Nobel Chemicals, Mississauga, Ontario), followed with ethyl cyanoacetate (135.6 grams, 1.2 mol, density 1.06 grams per milliliter; obtained from Spectrum Chemicals, New Brunswick, N.J.). The mixture was stirred and heated to 120° C. for a period of 1 hour, during which time a liquid by-product was distilled away. To the hot reaction mixture while stirring was then sequentially added the solvent N,N-dimethylformamide (320 grams, obtained from Caledon Labs, Brampton, Ontario), ethyl acetoacetate (260.0 grams, 2.0 mol, density 1.02 grams per milliliter; obtained from Lonza Group, Germany), and piperazine (192.2 grams, 2.0 mol; obtained from Spectrum Chemicals, New Brunswick, N.J.). The resultant mixture was heated to 110° C. internal temperature for 4 hours, during which time more liquid by-product was distilled away. A golden brown viscous solution resulted thereafter which was cooled to room temperature. The solution was carefully poured, with vigorous stirring while at room temperature, into a prepared solution of methanol (1,624 grams), deionized water (684 grams), and concentrated nitric acid (322 grams, 3.6 mol). A solid material precipitated immediately, and the resulting slurry was stirred for an additional 30 minutes. The slurry was vacuum filtered, and the solid filter cake was rinsed several times with 500 milliliter portions of a solvent mixture comprising 70 percent by volume methanol and 30 percent by volume water, until the conductivity of the filtrate was low. The solid cake was dried at 40° C. under vacuum for 24 hours to give 277 grams (87 percent yield) of the dodecyl pyridone product as a light beige solid. $^1$H-NMR spectral analysis indicated that the product was of high purity, with no evidence of contaminants exceeding approximately 2 percent of the product yield. $^1$H-NMR spectral assignments (300 MHz, DMSO-$d_6$): 5.6 ppm (singlet, H at ring position C-5), 3.88 ppm (broad triplet, 2H, $CH_2$ adjacent ring N), 2.2 ppm (singlet, 3H, $CH_3$ at ring position C-4), 1.6 ppm to 0.8 ppm ($CH_2$ and $CH_3$ protons from dodecyl group, 3 signals totaling 65 H integration).

Into a 1 liter round bottom flask equipped with a mechanical stirrer, dropping funnel, and thermometer was charged the dianthranilate prepared above (108 grams, 0.139 mol), followed sequentially with 210 milliliters of glacial acetic acid, 18 milliliters of concentrated sulfuric acid, 20 milliliters of deionized water, and 20 milliliters of propionic acid (obtained from Sigma-Aldrich Co.). The dark solution was chilled to an internal temperature of +3° to +5° C. Nitrosylsulfuric acid (NSA, commercial solution containing 40 percent by weight NSA in sulfuric acid, obtained from Sigma-Aldrich Co.; 56 milliliters, 0.285 mol) was then charged into the dropping funnel and was dripped slowly into the dianthranilate solution so as to keep the internal temperature between +3° and +5° C. and to minimize the emission of $NO_x$ gases. After about 1.5 hours, the NSA addition was completed. A small portion of sulfamic acid (1 gram, 0.01 mol) was then added to the mixture to quench any residual NSA, and the mixture was stirred for an additional 15 minutes.

The solution of dodecyl pyridone was prepared using a 10 liter graduated beaker equipped with a mechanical stirrer. Into this vessel was charged sodium hydroxide (55 grams, 1.39 mol) and sodium acetate (114 grams, 1.39 mol), followed with deionized water (3.5 liters) and isopropanol (2.5 liters). Once all of the ingredients had dissolved, the dodecylpyridone prepared above was added to the solution and stirred vigorously until all pyridone solids were dissolved. The cold diazonium salt solution was then slowly poured into the dodecylpyridone coupling solution at room temperature. An instant bright yellow precipitate was formed, and after complete addition, the resulting slurry was stirred for an additional 0.5 hour prior to recovering the colorant material. The yellow slurry was vacuum filtered through a 3 micron hydrophobic membrane. The yellow filter cake was then reslurried again into a 20:80 mixture of isopropanol:deionized water, stirred for 30 minutes, and then filtered again. The filter cake was then subjected to the following treatment several times: redispersion into 1 liter of deionized water, stirring for 30 minutes, then filtration through a 3 micron hydrophobic membrane, until the pH of the resulting filtrate was greater than 5.0 and the conductivity of the filtrate was low. The cake was then dried in a vacuum-oven at 30° C. over 36 hours, affording 192.6 grams (96.3 percent yield) of the crude product as a mustard-yellow granular powder, melting point range of 123 to 134° C. The crude product was purified further by stirring in 2 liters of a hot mixture of 1:1 acetone and isopropanol to afford a bright orange-yellow powder. This purified material had a melting point of 128 to 134° C., UV/vis wavelength maximum of 430 nm (toluene), and spectral strength in toluene of 5.37× $10^4$ milliliters per gram-centimeter. $^1$H-NMR spectral assignments (300 MHz, $CDCl_3$): 8.18 ppm (doublet, 2H integration, aromatic H), 8.05 ppm (doublet, 2H integration, aromatic H), 7.65 ppm (triplet, 2H integration, aromatic H), 7.30 ppm (triplet, 2H integration, aromatic H), 4.45 ppm (doublet of doublets, 4H integration, $CH_2$ adjacent ester), 4.00 ppm (doublet of doublets, 4H integration, $CH_2$ adjacent pyridone), 2.65 ppm (singlet, 6H integration, $CH_3$ on pyridone ring), 1.90–0.80 ppm (multiplets, CH, $CH_2$, $CH_3$ integrating for >60H, all other alkyl protons).

EXAMPLE XIII

A colorant of the formula shown in Example XII was prepared as follows. A dimer ester anthranilate of the formula shown in Example XII was prepared as described in Example XII. Into a 1 liter round bottom flask equipped with mechanical stirrer, dropping funnel, and thermometer, was charged under agitation the dianthranilate (54.4 grams, 0.070 mol) followed with a prepared solution containing 173 milliliters of glacial acetic acid, 43 milliliters of deionized water, and 15 milliliters of concentrated sulfuric acid. The resulting dark solution was chilled to an internal temperature of +3 to +5° C. Nitrosylsulfuric acid (NSA, commercial solution containing 40 percent by weight NSA in sulfuric acid, obtained from Sigma-Aldrich Co., Milwaukee, Wis., 45.6 grams, 0.144 mol) was charged into the dropping funnel and then dripped slowly into the solution at a rate whereby the internal temperature was maintained between 0° C. and +8° C. After 20 minutes, the NSA addition was completed and the mixture was stirred for an additional 15 minutes while being cooled at 0° C. Urea (0.2 grams. 3.3 mmol) was then added to the mixture to quench any residual NSA reagent and the mixture was stirred for 15 more minutes.

A coupling solution of dodecyl pyridone was prepared in a 2 liter kettle equipped with mechanical stirrer. Into this vessel was charged dodecyl pyridone (45.7 grams, 0.144 mol) prepared as described in Example XII, followed with 457 milliliters of isopropanol. A solution of sodium hydroxide (21.5 grams, 0.538 mol), sodium acetate trihydrate (73.2 grams, 0.538 mol), and 457 milliliters of deionized water was prepared and then added to the briskly stirred dispersion of the pyridone in isopropanol. A brown solution was formed after 15 minutes of stirring at room temperature. The cold diazonium salt solution was then slowly poured into the vigorously stirring dodecyl pyridone coupling solution. A bright yellow precipitate was formed instantly, and after complete addition of the diazonium salt solution, the yellow slurry was stirred an additional 30 minutes.

The yellow slurry was vacuum filtered through a 3 micron hydrophobic membrane media. The yellow dye cake was then redispersed into a 50:50 mixture of isopropanol and deionized water and stirred for 30 minutes. The filter cake was then subjected to the following treatment several times—redispersion into 1 liter of a 50:50 mixture of isopropanol and deionized water, stirring for 30 minutes, and filtration through 3 micron hydrophobic membrane—until the pH of the resulting filtrate was greater than 5.0 and the conductivity of the filtrate was low. The filter cake was given two final rinses with 1 liter volumes of methanol. The cake was then dried in a vacuum-oven at 40° C. for 36 hours, affording 90 grams (89.6 percent yield) of the crude product as a bright yellow powder, melting point range of 121 to 133° C., UV/vis wavelength maximum of 430 nm (toluene) and spectral strength in toluene of $5.14 \times 10^4$ milliliters per gram-centimeter. If desired, this material can be further purified by recrystallization as described in Example XII.

EXAMPLE XIV

A colorant of the formula

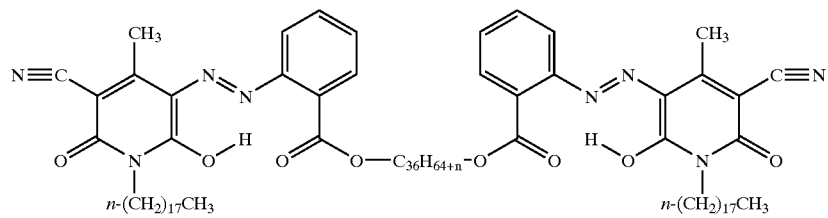

wherein $C_{36}H_{64+n}$ was a branched alkylene group which may include unsaturations and cyclic groups, wherein n is an integer of 0, 1, 2, 3, 4, 5, 6, 7, 8, 9, or 10, and wherein one isomer thereof was of the formula

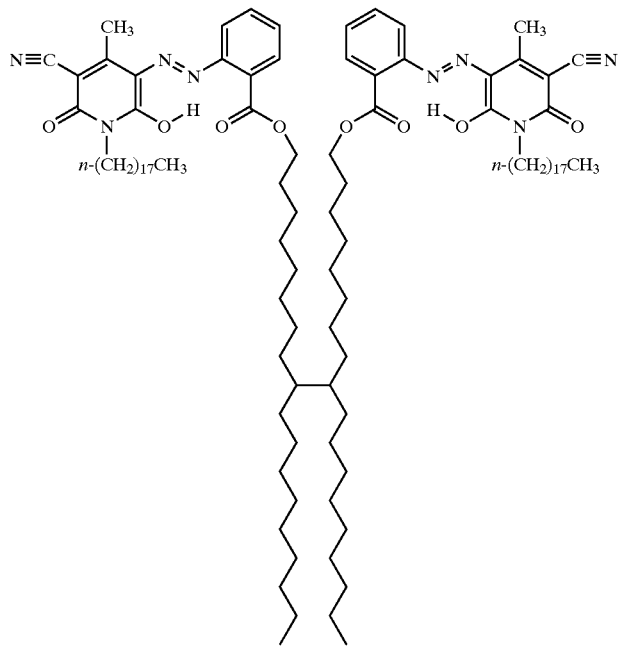

was prepared as follows.

A dimer ester anthranilate of the formula

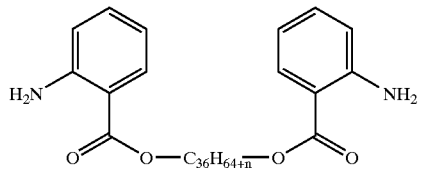

wherein $C_{36}H_{64+n}$ was a branched alkylene group which may include unsaturations and cyclic groups, wherein n is an integer of 0, 1, 2, 3, 4, 5, 6, 7, 8, 9, or 10, and wherein one isomer thereof was of the formula

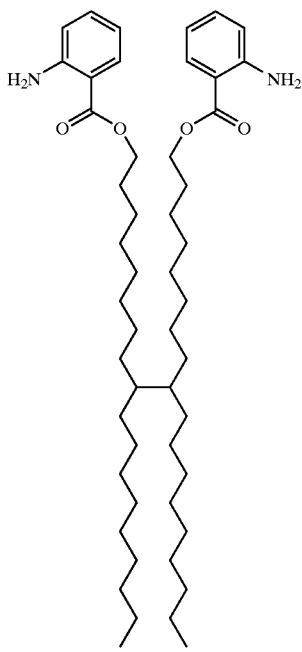

was prepared as described in Example XII.

Into a 2 liter flask equipped with magnetic stir bar and temperature thermostat was charged octadecylamine (stearylamine, 18.9 grams, 0.07 mol; obtained from Sigma-Aldrich Co., Milwaukee, Wis.) followed with ethyl cyanoacetate (7.9 grams, 0.07 mol, density 1.06 grams per milliliter; obtained from Spectrum Chemicals, New Brunswick, N.J.). The resulting mixture was stirred and heated to 120° C. internal temperature for 1 hour, during which time a liquid byproduct was distilled away. To the hot reaction mixture was then sequentially added ethyl acetoacetate (10.08 grams, 0.0775 mol, density 1.02 grams per milliliter; obtained from Lonza Group, Germany), piperidine (11.0 grams, 0.13 mol, density 0.861 grams per milliliter; obtained from Sigma-Aldrich Co.), and a solvent mixture (60 milliliters) containing 5 parts by weight toluene and 1 part by weight 1,2-dimethoxyethane. The reaction proceeded with stirring at 120° C. for another 24 hours. The solvents were then distilled off in vacuo, and the remaining viscous solution was carefully poured into a stirring solution of methanol (80 milliliters), deionized water (20 milliliters), and concentrated hydrochloric acid (16 milliliters, 2.5 mol).

A solid precipitate formed instantly and the slurry was vacuum filtered followed by rinsing of the solid cake with 2×50 milliliter portions of 80 percent aqueous methanol. The cake thus obtained was air-dried for 24 hours to afford 24.5 grams (0.061 mol, 87 percent yield) of N-stearyl pyridone product as light tan powder.

Into a 1 liter round bottom flask equipped with a mechanical stirrer, dropping funnel, and thermometer was charged the dimer ester anthranilate prepared above (87 grams, 0.112 mol), followed sequentially with 170 milliliters of glacial acetic acid, 17 milliliters of concentrated sulfuric acid, 17 milliliters of deionized water, and 17 milliliters of propionic acid (obtained from Sigma-Aldrich Co.). The dark solution was chilled to an internal temperature of +3° C. to +5° C. while stirring. Nitrosylsulfuric acid (NSA, commercial solution containing 40 percent by weight NSA in sulfuric acid, obtained from Sigma-Aldrich Co.; 71 grams, 0.224 mol) was then charged into the dropping funnel and was dripped slowly into the solution so as to keep the internal temperature between 0° and +8° C. After 1 hour, the NSA addition was completed, and the mixture was stirred for an additional 0.5 hour while chilled. Sulfamic acid (1 gram, 0.01 mol) was then added to the mixture to quench any residual NSA, and the mixture was stirred for an additional 15 minutes.

The solution of stearyl pyridone was prepared in a 4 liter flask equipped with mechanical stirrer. Into this vessel was charged sodium hydroxide (45 grams, 1.12 mol) and sodium acetate (92 grams, 1.12 mol), followed with deionized water (2 liters) and isopropanol (1.5 liter). Once all of the ingredients had dissolved, excess stearyl pyridone (139.5 grams, 0.35 mol) was added to the solution under vigorous agitation. The mixture was agitated for 30 minutes, after which any undissolved solids were removed by filtration. The pyridone solution was then transferred to a 10 liter glass vessel equipped with mechanical stirrer. The cold diazonium salt solution was then slowly poured into the briskly stirring stearyl pyridone solution at room temperature. A bright yellow precipitate was formed instantly, and the slurry viscosity increased as more diazonium salt solution was added, requiring an additional 1.0 liter of deionized water to aid stirring. The slurry was stirred for 1 hour at room temperature prior to recovering the colorant material. The slurry was vacuum filtered through a 3 micron hydrophobic membrane media. All of the colorant material from the filter cake was then dissolved into 4 liters of dichloromethane solvent and divided into two 2 liter separatory funnels. Several extractions of the dichloromethane layer were performed using 1 liter portions of deionized water until the final aqueous layer measured a pH of about 5 and a low conductivity. The dichloromethane solvent was removed in vacuo by distillation, leaving a crude yellow-brown solid. The crude product was recrystallized in boiling isopropanol (about 3 liters) to afford a bright yellow-orange granular powder, melting point range of 122 to 123° C. $^1$H-NMR spectral analysis showed this material to be of high purity in accordance with the structure shown.

EXAMPLE XV

A colorant of the formula

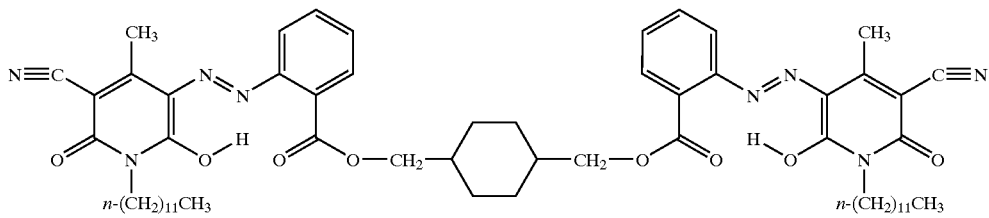

(including both the cis and the trans configurational isomers within the central cyclohexane ring) was prepared as follows.

A dimer ester anthranilate of the formula

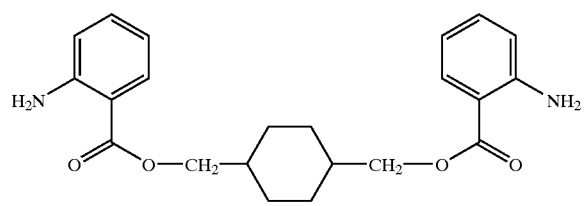

(including both the cis and the trans configurational isomers within the central cyclohexane ring) was prepared as follows. 1,4-Cyclohexanedimethanol (144.2 grams, 1.0 mol), isatoic anhydride (408 grams, 2.50 mol; obtained from Sigma-Aldrich Co.), and triethylamine (22.4 grams, 0.20 mol; obtained from Sigma-Aldrich Co.) in 500 milliliters of N,N-dimethylformamide in a 4 liter beaker was stirred and heated to 100° C. for 2.5 hours. The reaction solution was then cooled to 50° C. and treated with 2 liters of methanol. The resultant white suspension was stirred for 2 hours, followed by filtration and washing of the solid in the filter funnel with 5×100 milliliter portions of methanol. Drying at 60° C. for 24 hours gave 195.5 grams of white solid, identified as pure 1,4-cyclohexanedimethyl dianthranilate (greater than 99 percent by $^1$H-NMR spectroscopy). The melting point of this product was 144 to 145° C.

Dodecyl pyridone was prepared as described in Example XII.

To a suspension of the 1,4-dimethylcyclohexane dianthranilate prepared above (19.1 grams, 0.050 mol) in 100 milliliters of glacial acetic acid was added concentrated sulfuric acid (10 milliliters) followed sequentially with 20 milliliters of water. The resultant suspension was cooled in an ice-salt bath and the temperature was maintained between +3 and +6° C. as nitrosyl sulfuric acid (NSA, commercial solution containing 40 percent by weight NSA in sulfuric acid, obtained from Sigma-Aldrich Co.; 21 milliliters, 0.105 mol) was slowly dripped into the stirred mixture over 45 minutes. The resultant suspension was stirred at about 5° C. for 1 hour.

The coupler solution of dodecyl pyridone was prepared by suspending the dodecyl pyridone prepared as described in Example XII (31 grams, 0.105 mol) in 800 milliliters of water and adding sodium hydroxide (20 grams, 0.50 mol), sodium acetate (49 grams, 0.60 mol), and isopropanol (400 milliliters). The resultant turbid solution was vigorously stirred while the suspension of the diazotized dianthranilate was slowly poured into it. A bright yellow suspension formed at once. The suspension was stirred at room temperature for 1 hour, followed by filtration and washing of the solid with 3×500 milliliter portions of water. The wet cake was redispersed in 2 liters of water and was then filtered and washed with 3×100 milliliters of water followed by 3×100 milliliters of isopropanol. The wet cake was then stirred in 100 milliliters of isopropanol at 80° C. for 1 hour. Filtration and washing with isopropanol followed by drying in air for 24 hours gave the crude product as a green-yellow solid (26.7 grams). The product was stirred in 400 milliliters of dichloromethane, and the suspension thus obtained was then treated with 100 milliliters of methanol. The mixture was filtered and the solid was washed with 4×50 milliliter portions of methanol. The collected solid was dried at 60° C. to give 23.1 grams (44 percent yield) of the colorant as bright yellow powder.

EXAMPLE XVI

A colorant of the formula

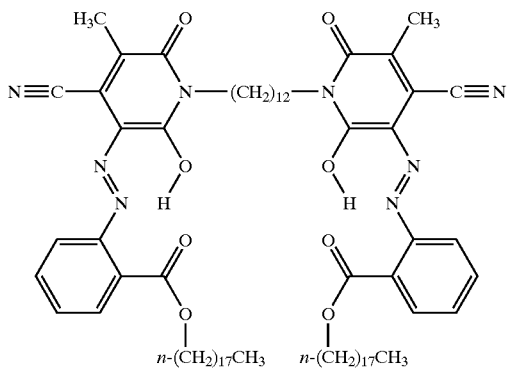

was prepared as follows.

A mixture of octadecanol (270 grams, 1.0 mol; obtained from Sigma-Aldrich Co.), isatoic anhydride (244 grams, 1.5 mol; obtained from Sigma-Aldrich Co.), and 1,4-diazabicyclo[2.2.2]octane (56 grams, 0.50 mol; obtained from Sigma-Aldrich Co.), in 1,000 milliliters of dimethylformamide was stirred and heated to 100° C. in a 4 liter beaker. Vigorous gas evolution occurred. After 10 minutes, the resultant dark solution was heated to 150° C. for 15 minutes. The reaction mixture was then cooled to 50° C. and vigorously stirred while 3,000 milliliters of methanol was added. The resultant suspension was stirred for 0.5 hour, followed by vacuum filtration. The solid thus obtained was washed in the filter funnel with 4×300 milliliter portions of methanol and was then dried in air to give the product stearyl anthranilate as white powder (330.5 grams, 85 percent yield).

A mixture of 1,12-diaminododecane (100.1 grams, 0.50 mol; obtained from Sigma-Aldrich Co.) and ethyl cyanoacetate (135.2 grams, 128 milliliters, 1.20 mol; obtained from Spectrum Chemicals, New Brunswick, N.J.), in a 2 liter flask was stirred and heated at 150° C. for 1 hour, after which time the amine had been completely converted to the bis (cyanoacetate) as indicated by $^1$H-NMR analysis. Ethyl acetoacetate (383 milliliters, 3.00 mol; obtained from Lonza Group, Germany), piperazine (172 grams, 2.00 mol; obtained from Spectrum Chemicals), and dimethyl formamide (300 milliliters) were then added to the reaction mixture and the mixture was heated at 120° C. for 4 hours. The resultant pole brown solution was then cooled to 25° C. and was poured into a mixture of methanol (1,500 milliliters), water (500 milliliters), and concentrated (70 percent) nitric acid (300 grams, 258 milliliters, 4.0 mol). A precipitate formed at once. The suspension was stirred overnight, followed by filtration and washing of the solid with 5×500 milliliter portions of 75:25 (volume ratio) of a methanol-water mixture and subsequent drying at 60° C. to give 198 grams (85 percent yield) of dodecamethylene dipyridone as a cream-white solid, which decomposed without melting at 210° C.

The stearyl anthranilate prepared above (25.3 grams, 0.065 mol) was dissolved in a mixture of glacial acetic acid (65 milliliters) and dodecylbenzene sulfonic acid (65 milliliters; obtained from Stepan Chemicals as BIOSOFT® S-101, Northfield, Ill.). The resulting solution was stirred and cooled in an ice bath and the temperature was maintained between 120 and 16° C. while nitrosyl sulfuric acid (NSA, commercial solution containing 40 percent by weight NSA in sulfuric acid, obtained from Sigma-Aldrich Co.: 22.2 grams, 14 milliliters, 0.07 mol) was slowly dripped into the solution. The solution was stirred for an additional 0.5 hour at about 5° C.

A dipyridone solution was prepared by dissolving the 1,12-dodecamethylene dipyridone prepared above (16.3 grams, 0.035 mol) in 800 milliliters of water containing 12 grams (0.30 mol) of sodium hydroxide, 33 grams (0.40 mol) of sodium acetate, and 200 milliliters of isopropanol. The diazonium salt solution was slowly poured into the turbid dipyridone solution with vigorous stirring. The resultant yellow suspension was stirred for 30 minutes at room temperature, followed by vacuum filtration. The collected solid was washed in the funnel with 3×50 milliliter portions of water. The wet cake was then dispersed in 1,000 milliliters of hot (70° C.) water and then was refiltered and the solid washed with 3×100 milliliter portions of water. The wet cake was thereafter dispersed in 100 milliliters of isopropanol, which was then heated at reflux for 1 hour. Hot filtration followed by washing with isopropanol (3×50 milliliter portions) followed by methanol (3×100 milliliter portions) and drying at 60° C. gave the colorant as a green-yellow solid (38.2 grams, 93 percent yield).

EXAMPLE XVII

A colorant of the formula

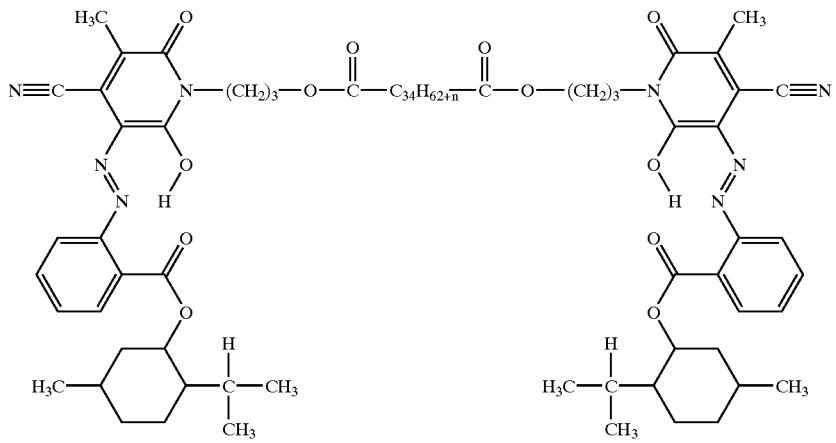

wherein $C_{34}H_{62+n}$ was a branched alkylene group which may include unsaturations and cyclic groups, wherein n is an integer of 0, 1, 2, 3, 4, 5, 6, 7, 8, 9, or 10, and wherein one isomer thereof was of the formula

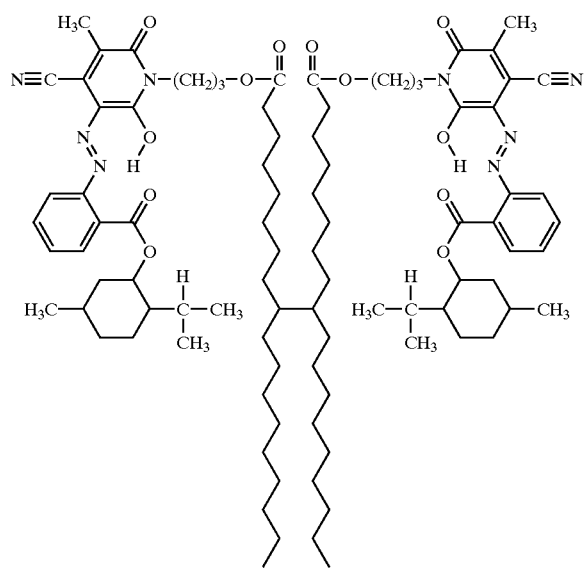

was prepared as follows.

A 500 milliliter round-bottom flask was charged sequentially with ethyl cyanoacetate (10.4 grams, 0.092 mol; obtained from Sigma-Aldrich Co.), ethanol (60 milliliters), and 3-aminopropanol (7 grams, 0.095 mol; obtained from Sigma-Aldrich Co.). The mixture thus formed was stirred and heated to 50° C. over 2 hours, after which time neat ethyl acetoacetate (12 grams, 0.092 mol: obtained from Sigma-Aldrich Co.) was added into the mixture, followed by the addition of potassium carbonate powder (13.4 grams, 0.097 mol). The mixture was then stirred and heated at 90° C. for 8 to 10 hours. The mixture was then chilled in an ice bath and carefully acidified with 25 milliliters of 50 percent hydrochloric acid. A white precipitate formed instantly, and after stirring for 30 minutes, the slurry was vacuum filtered. The white solid cake thus collected was rinsed with cold tetrahydrofuran, and was then air-dried to give 16 grams of a white granular solid (84 percent yield). $^1$H-NMR analysis indicated that the material was pure N-(3-hydroxypropyl) pyridone.

A 250 milliliter round bottom flask equipped with thermometer and dropping funnel was charged with menthyl anthranilate (7.6 grams, 0.027 mol; obtained from Sigma-Aldrich Co.), followed sequentially by addition of glacial acetic acid (25 milliliters), water (5 milliliters), and concentrated sulfuric acid (1 milliliter), giving a clear colorless solution. The solution thus formed was cooled to an internal temperature of 0° C. Thereafter, nitrosyl sulfuric acid (NSA, commercial solution containing 40 percent by weight NSA in sulfuric acid, obtained from Sigma-Aldrich Co.; 5.4 milliliters, 0.027 mol) was added slowly by a dropping funnel at a rate such that the internal temperature was maintained between 0° C. and 8° C. After addition was completed, the mixture was stirred for 30 minutes, and then excess NSA was quenched by adding sulfamic acid (0.5 grams, obtained from Sigma-Aldrich Co.).

A solution containing the N-(3-hydroxypropyl)pyridone prepared above was then prepared as follows. A 500 milliliter vessel equipped with mechanical stirrer was charged with sodium hydroxide (7.75 grams, 0.194 mol), anhydrous sodium acetate (22.7 grams, 0.277 mol), and water (200 milliliters). Once the solids were all dissolved, the N-(3-hydroxypropyl)pyridone (7.6 grams, 0.029 mol) was added and dissolved with stirring. The cold diazonium salt solution was then slowly poured into the pyridone solution with stirring, instantly forming a bright orange-yellow slurry. The mixture was stirred for 30 minutes more, followed by vacuum filtration. The orange yellow cake thus collected was repeatedly washed and reslurried with water until the filtrate pH was greater than 5.0 and the filtrate conductivity was low. The colorant thus formed was air-dried, giving 13.4 grams (quantitative yield) of a bright orange-yellow powder.

A 250 milliliter flask equipped with a water condenser and thermometer was charged with the menthyl anthranilate/3-hydroxypropylpyridone yellow colorant thus prepared (6 grams, 0.012 mol), a C-36 dimeric diacid (commercially sold as PRIPOL® 1009, obtained from Uniqema, Newcastle, Del.; 3.44 grams, 0.0061 mol) along with toluene (100 milliliters) and p-toluenesulfonic acid (460 milligrams, 2.4 mmol). The heterogeneous mixture thus formed was heated to dissolution at 110° C. After 9 hours the reaction was complete and the mixture was subsequently cooled to room temperature, resulting in the precipitation of an orange-yellow solid. The solid was extracted into a mixture of toluene (40 milliliters) and tetrahydrofuran (10 milliliters), then washed with deionized water (3×150 milliliter portions) until the pH of the aqueous layer was neutral. The organic layer was concentrated in vacuo to about 20 milliliters in volume, and was then treated with isopropanol to precipitate the colorant product. The colorant solid was filtered and air-dried to give 6.68 grams (72 percent yield) of a bright orange-yellow solid with a melting point of 156° C., UV/vis wavelength maximum of 430 nm (toluene), and spectral strength in toluene of $5.11 \times 10^4$ milliliters per gram-centimeter.

Other embodiments and modifications of the present invention may occur to those of ordinary skill in the art subsequent to a review of the information presented herein; these embodiments and modifications, as well as equivalents thereof, are also included within the scope of this invention.

The recited order of processing elements or sequences, or the use of numbers, letters, or other designations therefor, is not intended to limit a claimed process to any order except as specified in the claim itself.

What is claimed is:

1. A process for preparing substituted pyridone compounds which comprises (a) admixing in the absence of a solvent (1) an amine of the formula $R_1$—$NH_2$ wherein $R_1$ is an alkyl group having at least about 8 carbon atoms, an aryl group, an arylalkyl group, or an alkylaryl group, and (2) a first ester of the formula

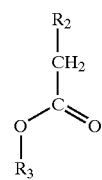

wherein $R_2$ is an electron withdrawing group and $R_3$ is an alkyl group; (b) heating mixture containing the amine and the first ester to form an intermediate compound of the formula

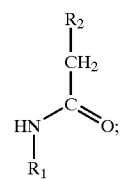

(c) admixing the intermediate compound with (1) a base and (2) a second ester of the formula

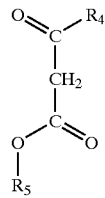

wherein $R_4$ is an alkyl group, an aryl group, an arylalkyl group, or an alkylaryl group and $R_5$ is an alkyl group, said second ester being present in a molar excess relative to the intermediate compound, said base being present in a molar excess relative to the intermediate compound, and (d) heating the mixture containing the intermediate compound, the second ester, and the base to form a pyridone compound of the formula

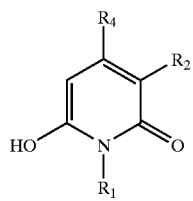

or a salt thereof.

2. A process according to claim 1 wherein $R_1$ is an alkyl group with at least about 8 carbon atoms, an aryl group with at least about 10 carbon atoms, an arylalkyl group with at least about 12 carbon atoms, or an alkylaryl group with at least about 12 carbon atoms.

3. A process according to claim 1 wherein $R_1$ is an alkyl group with at least about 12 carbon atoms.

4. A process according to claim 1 wherein $R_1$ is an alkyl group with at least about 14 carbon atoms.

5. A process according to claim 1 wherein the amine of the formula $R_1$—$NH_2$ is a diamine of the formula $H_2N$—$R_1$—$NH_2$.

6. A process according to claim 1 wherein the amine of the formula $R_1$—$NH_2$ is a amine of the formula $R_1(NH_2)_3$.

7. A process according to claim 1 wherein the amine is octyl amine, decyl amine, dodecyl amine, tetradecyl amine, hexadecyl amine, octadecyl amine, abietyl amine, or mixtures thereof.

8. A process according to claim 1 wherein the amine is 1,3-diaminopentane, 1,6-diaminohexane, 2-methyl-1,5-diaminopentane, 3-methyl-1,5-diaminopentane, 1,8-diaminooctane, 1,10-diaminodecane, 1,12-diaminododecane, 4,7-dioxadecan-1,1-diyl diamine, dioxadodecan-1,12-diyl diamine, 1,4-cyclohexyldimethylene diamine, 1,3-cyclohexyldimethylene diamine, bicyclohexan-4,4'-diyl diamine, dicyclohexylmethane-4,4'-diyl diamine, isopropylidenedicyclohexan-4,4'-diyl diamine, tris(2-aminoethyl)amine, 3-methyleneoctane-1,8-diyl triamine, or mixtures thereof.

9. A process according to claim 1 wherein $R_2$ is a cyanato group, an isocyanato group, an isocyano group, a cyano group, a thiocyanato group, an isothiocyanato group, a halide atom, or a group of the formula

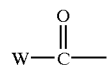

wherein W is a hydrogen atom, an alkyl group, an aryl group, an arylalkyl group, or an alkylaryl group.

10. A process according to claim 1 wherein $R_2$ is a cyano group.

11. A process according to claim 1 wherein the first ester is methyl cyanoacetate, ethyl cyanoacetate, n-propyl cyanoacetate, isopropyl cyanoacetate, n-butyl cyanoacetate, tert-butyl cyanoacetate, or a mixture thereof.

12. A process according to claim 1 wherein the first ester is ethyl cyanoacetate.

13. A process according to claim 1 wherein the mixture formed in step (a) and heated in step (b) consists essentially of the amine and the first ester.

14. A process according to claim 1 wherein the mixture formed in step (a) and heated in step (b) consist of the amine and the first ester.

15. A process according to claim 1 wherein the amine and the first ester are present in relative amounts of at least about 0.75 moles of amine per every one mole of first ester, and wherein the amine and the first ester ore present in relative amounts of no more than about 1.25 moles of amine per every one mole of first ester.

16. A process according to claim 1 wherein the mixture of the amine and the first ester is heated to a temperature of at least about 80° C., and wherein the mixture of the amine and the first ester is heated to a temperature of no more than about 160° C.

17. A process according to claim 1 wherein the mixture of the amine and the first ester is heated for a period of at least about 10 minutes, and wherein the mixture of the amine and the first ester is heated for a period of no more than about 480 minutes.

18. A process according to claim 1 wherein the second ester is methyl acetoacetate, ethyl acetoacetate, t-butyl acetoacetate, ethyl butyrylacetate, or a mixture thereof.

19. A process according to claim 1 wherein the second ester is ethyl acetoacetate.

20. A process according to claim 1 wherein the base is piperidine, 1-methylpiperidine, 1-ethylpiperidine, piperazine, 1-ethylpiperazine, 2-ethylpiperazine, 1-methylpiperazine, 2-methylpiperazine, sodium hydroxide, triethylamine, tributylamine, dimethylethanolamine, diethylethanolamine, 1,4-diazabicyclo[2.2.2]octane, morpholine, 4-ethylmorpholine, t-octylamine, hexamethyl disilazane, tetramethyl ethylenediamine, diethylcyclohexylamine, di-isopropylethylamine, 4,4'-trimethylene-dipiperidine, 1,4-dimethyl-piperazine, benzimidazole, benzoxazole, dipiperidino-methane, tris-[2-(2-methoxyethoxy)ethyl]amine, or a mixture thereof.

21. A process for preparing substituted pyridone compounds which comprises (a) admixing in the absence of a solvent (1) an amine of the formula $R_1$—$NH_2$ wherein $R_1$ is an alkyl group, an aryl group, an arylalkyl group, or an alkylaryl group, and (2) a first ester of the formula

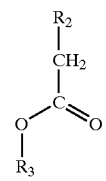

wherein $R_2$ is an electron withdrawing group and $R_3$ is an alkyl group; (b) heating the mixture containing the amine and the first ester to form an intermediate compound of the formula

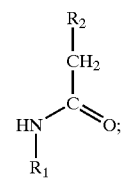

(c) admixing the intermediate compound with (1) a base which is piperidine, piperazine, 1,4-diazabicyclo[2.2.2] octane, or a mixture thereof, and (2) a second ester of the formula

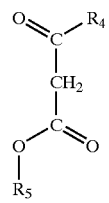

wherein $R_4$ is an alkyl group, an aryl group, an arylalkyl group, or an alkylaryl group and $R_5$ is an alkyl group, said second ester being present in a molar excess relative to the intermediate compound, said base being present in a molar excess relative to the intermediate compound, and (d) heating the mixture containing the intermediate compound, the second ester, and the base to form a pyridone compound of the formula

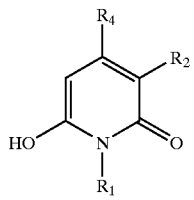

or a salt thereof.

22. A process according to claim 21 wherein the base is piperazine.

23. A process according to claim 1 wherein the intermediate compound and the second ester are present in relative amounts of at least about 1.1 moles of second ester per every one mole of intermediate.

24. A process according to claim 1 wherein the intermediate compound and the second ester are present in relative amounts of at least about 1.2 moles of second ester per every one mole of intermediate.

25. A process according to claim 1 wherein the intermediate compound and the second ester are present in relative amounts of at least about 1.5 moles of second ester per every one mole of intermediate.

26. A process according to claim 1 wherein the intermediate compound and the second ester are present in relative amounts of at least about 2 moles of second ester per every one mole of intermediate.

27. A process according to claim 1 wherein the intermediate compound and the base are present in relative amounts of at least about 1.1 moles of base per every one mole of intermediate.

28. A process according to claim 1 wherein the intermediate compound and the base are present in relative amounts of at least about 1.2 moles of base per every one mole of intermediate.

29. A process according to claim 1 wherein the intermediate compound and the base are present in relative amounts of at least about 1.5 moles of base per every one mole of intermediate.

30. A process according to claim 1 wherein the intermediate compound and the base are present in relative amounts of at least about 2 moles of base per every one mole of intermediate.

31. A process according to claim 1 wherein in step (c) the intermediate compound, the base, and the second ester are admixed with a solvent.

32. A process according to claim 31 wherein the solvent is dimethyl formamide, N-methyl pyrrolidinone, toluene, sulfolane, or a mixture thereof.

33. A process according to claim 31 wherein the intermediate is present in the solvent in an amount of at least about 1 mole of intermediate per liter of solvent, and wherein the intermediate is present in the solvent in an amount of no more than about 10 moles of intermediate per liter of solvent.

34. A process according to claim 1 wherein the mixture containing the intermediate compound, the second ester, and the base is heated to a temperature of at least about 80° C., and wherein the mixture containing the intermediate compound, the second ester, and the base is heated to a temperature of no more than about 160° C.

35. A process according to claim 1 wherein the mixture containing the intermediate compound, the second ester, and the base is heated for a period of at least about 30 minutes, and wherein the mixture containing the intermediate compound, the second ester, and the base is heated for a period of no more than about 1,440 minutes.

36. A process according to claim 1 wherein the pyridone is recovered by cooling the reaction mixture to room temperature and pouring it into a non-solvent for the pyridone.

37. A process according to claim 36 wherein the non-solvent is water, methanol, ethanol, n-propanol, isopropanol, butanol, ethyl acetate, propyl acetate, butyl acetate, or a mixture thereof.

38. A process for preparing substituted pyridone compounds which comprises (a) admixing in the absence of a solvent (1) an amine of the formula $R_1-NH_2$ wherein $R_1$ is an alkyl group, an aryl group, an arylalkyl group, or an alkylaryl group, and (2) a first ester of the formula

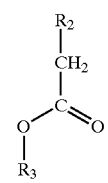

wherein $R_2$ is an electron withdrawing group and $R_3$ is an alkyl group; (b) heating the mixture containing the amine and the first ester to form an intermediate compound of the formula

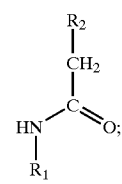

(c) admixing the intermediate compound with (1) a base and (2) a second ester of the formula

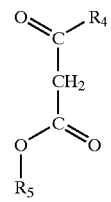

39. A process according to claim 36 wherein the non-solvent is a mixture containing from 60 to 80 parts by volume methanol and from 20 to 40 parts by volume water.

40. A process according to claim 1 wherein a pyridone salt is formed and wherein the pyridone salt is converted to a hydroxy pyridone by reacting the pyridone salt with an acid.

41. A process for preparing substituted pyridone compounds which comprises (a) admixing in the absence of a solvent (1) an amine of the formula $R_1-NH_2$ wherein $R_1$ is an alkyl group having at least about 12 carbon atoms, an aryl group, an arylalkyl group, or an alkylaryl group, and (2) a first ester of the formula

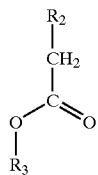

wherein $R_2$ is a cyano group and $R_3$ is an alkyl group; (b) heating the mixture containing the amine and the first ester to a temperature of at least about 80° C. for a period of at least about 10 minutes to form an intermediate compound of the formula

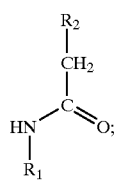

(c) admixing the intermediate compound with (1) a base, (2) a second ester of the formula

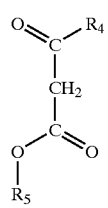

wherein $R_4$ is an alkyl group, an aryl group, an arylalkyl group, or an alkylaryl group and $R_5$ is an alkyl group, and (3) a solvent, wherein the intermediate compound and the second ester are present in relative amounts of at least about 1.1 moles of second ester per every one mole of intermediate, wherein the intermediate compound and the base are present in relative amounts of at least about 1.1 moles of base per every one mole of intermediate, and (d) heating the mixture containing the intermediate compound, the second ester, and the base to a temperature of at least about 80° C. for a period of at least about 30 minutes to form a pyridone compound of the formula

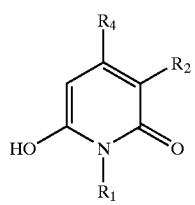

or a salt thereof.

42. A process for preparing diazopyridone compounds which comprises (a) admixing in the absence of a solvent (1) an amine of the formula $R_1$—$NH_2$ wherein $R_1$ is an alkyl group, an aryl group, an arylalkyl group, or an alkylaryl group, and (2) a first ester of the formula

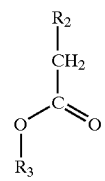

wherein $R_2$ is an electron withdrawing group and $R_3$ is an alkyl group; (b) heating the mixture containing the amine and the first ester to form an intermediate compound of the formula

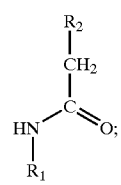

(c) admixing the intermediate compound with (1) a base and (2) a second ester of the formula

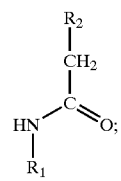

(c) admixing the intermediate compound with (1) a base and (2) a second ester of the formula

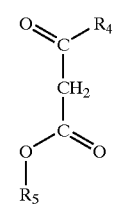

wherein $R_4$ is an alkyl group, an aryl group, an arylalkyl group, or an alkylaryl group and $R_5$ is an alkyl group, said second ester being present in a molar excess relative to the intermediate compound, said base being present in a molar excess relative to the intermediate compound, (d) heating the mixture containing the intermediate compound, the

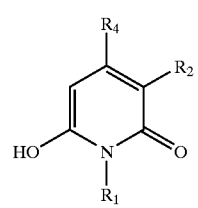

or a salt thereof; and (e) reacting the pyridone compound with a diazonium salt of the formula

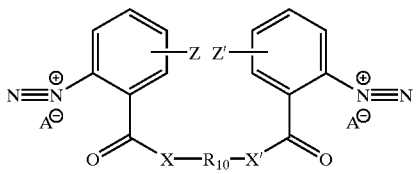

wherein $R_{10}$ is (i) an alkylene group, (ii) an arylene group, (iii) an arylalkylene group, (iv) an alkylarylene group, (v) an alkyleneoxy group, (vi) an aryleneoxy group, (vii) an arylalkyleneoxy group, (viii) an alkylaryleneoxy group, (ix) a polyalkyleneoxy group, (x) a polyaryleneoxy group, (xi) a polyarylalkyleneoxy group, (xii) a polyalkylaryleneoxy group, (xiii) a heterocyclic group, (xiv) a silylene group, (xv) a siloxane group, (xvi) a polysilylene group, or (xvii) a polysiloxane group, X and X' each, independently of the other, is (i) a direct bond, (ii) an oxygen atom, (iii) a sulfur atom, (iv) a group of the formula —$NR_{40}$— wherein $R_{40}$ is a hydrogen atom, an alkyl group, an aryl group, an arylalkyl group, or an alkylaryl group, or (v) a group of the formula —$CR_{50}R_{60}$— wherein $R_{50}$ and $R_{60}$ each, independently of the other, is a hydrogen atom, an alkyl group, an aryl group, an arylalkyl group, or an alkylaryl group, Z and Z' each, independently of the other, is (i) a hydrogen atom, (ii) a halogen atom, (iii) a nitro group, (iv) an alkyl group, (v) an aryl group, (vi) an arylalkyl group, (vii) an alkylaryl group, (viii) a group of the formula

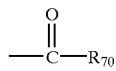

wherein $R_{70}$ is an alkyl group, an aryl group, an arylalkyl group, an alkylaryl group, an alkoxy group, an aryloxy group, an arylalkyloxy group, an alkylaryloxy group, a polyalkyleneoxy group, a polyaryleneoxy group, a polyarylalkyleneoxy group, a polyalkylaryleneoxy group, a heterocyclic group, a silyl group, a siloxane group, a polysilylene group, or a polysiloxane group, (ix) a sulfonyl group of the formula —$SO_2R_{80}$ wherein $R_{80}$ is a hydrogen atom, an alkyl group, an aryl group, an arylalkyl group, an alkylaryl group, on alkoxy group, an aryloxy group, an arylalkyloxy group, an alkylaryloxy group, a polyalkyleneoxy group, a polyaryleneoxy group, a polyarylalkyleneoxy group, a polyalkylaryleneoxy group, a heterocyclic group, a silyl group, a siloxane group, a polysilylene group, or a polysiloxane group, or (x) a phosphoryl group of the formula —$PO_3R_{90}$ wherein $R_{90}$ is a hydrogen atom, an alkyl group, an aryl group, an arylalkyl group, an alkylaryl group, an alkoxy group, an aryloxy group, an arylalkyloxy group, an alkylaryloxy group, a polyalkyleneoxy group, a polyaryleneoxy group, a polyarylalkyleneoxy group, a polyalkylaryleneoxy group, a heterocyclic group, a silyl group, a siloxane group, a polysilylene group, or a polysiloxane group, and A is an anion to form a diazopyridone colorant of the formula

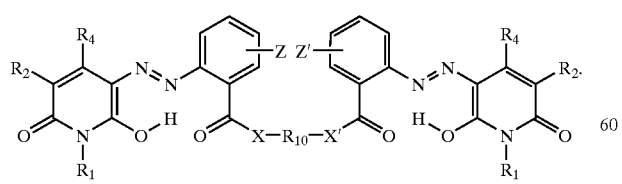

43. A process for preparing diazopyridone compounds which comprises (a) admixing in the absence of a solvent (1) a diamine of the formula $H_2N$—$R_1$—$NH_2$ wherein $R_1$ is an alkylene group, an arylene group, an arylalkylene group, or an alkylarylene group, and (2) a first ester of the formula

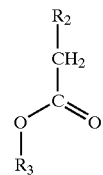

wherein $R_2$ is an electron withdrawing group and $R_3$ is an alkyl group; (b) heating the mixture containing the amine and the first ester to form an intermediate compound of the formula

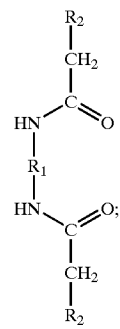

(c) admixing the intermediate compound with (1) a base and (2) a second ester of the formula

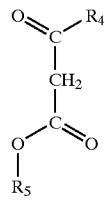

wherein $R_4$ is an alkyl group, an aryl group, an arylalkyl group, or an alkylaryl group and $R_5$ is an alkyl group, said second ester being present in a molar excess relative to the intermediate compound, said base being present in a molar excess relative to the intermediate compound, (d) heating the mixture containing the intermediate compound, the second ester, and the base to form a dipyridone compound of the formula

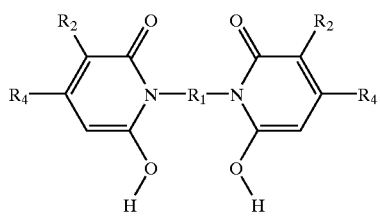

or a salt thereof; and (e) reacting the dipyridone compound with a diazonium salt of the formula

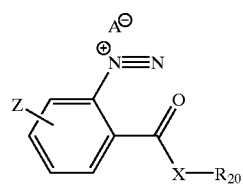

wherein $R_{20}$ is (i) an alkyl group, (ii) an aryl group, (iii) an arylalkyl group, (iv) an alkylaryl group, (v) an alkoxy group, (vi) an aryloxy group, (vii) an arylalkyloxy group, (viii) an alkylaryloxy group, (ix) a polyalkyleneoxy group, (x) a polyaryleneoxy group, (xi) a polyarylalkyleneoxy group, (xii) a polyalkylaryleneoxy group, (xiii) a heterocyclic group, (xiv) a silyl group, (xv) a siloxane group, (xvi) a polysilylene group, or (xvii) a polysiloxane group, X is (i) a direct bond, (ii) an oxygen atom, (iii) a sulfur atom, (iv) a group of the formula —$NR_{40}$— wherein $R_{40}$ is a hydrogen atom, an alkyl group, an aryl group, an arylalkyl group, or an alkylaryl group, or (v) a group of the formula —$CR_{50}R_{60}$— wherein $R_{80}$ and $R_{60}$ each, independently of the other, is a hydrogen atom, an alkyl group, an aryl group, an arylalkyl group, or an alkylaryl group, Z is (i) a hydrogen atom, (ii) a halogen atom, (iii) a nitro group, (iv) an alkyl group, (v) an aryl group, (vi) an arylalkyl group, (vii) an alkylaryl group, (viii) a group of the formula

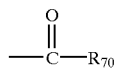

wherein $R_{70}$ is an alkyl group, an aryl group, an arylalkyl group, an alkylaryl group, an alkoxy group, an aryloxy group, an arylalkyloxy group, an alkylaryloxy group, a polyalkyleneoxy group, a polyaryleneoxy group, a polyarylalkyleneoxy group, a polyalkylaryleneoxy group, a heterocyclic group, a silyl group, a siloxane group, a polysilylene group, or a polysiloxane group, (ix) a sulfonyl group of the formula —$SO_2R_{80}$ wherein $R_{80}$ is a hydrogen atom, an alkyl group, an aryl group, an arylalkyl group, an alkylaryl group, an alkoxy group, an aryloxy group, an arylalkyloxy group, an alkylaryloxy group, a polyalkyleneoxy group, a polyaryleneoxy group, a polyarylalkyleneoxy group, a polyalkylaryleneoxy group, a heterocyclic group, a silyl group, a siloxane group, a polysilylene group, or a polysiloxane group, or (x) a phosphoryl group of the formula —$PO_3R_{90}$ wherein $R_{90}$ is a hydrogen atom, an alkyl group, an aryl group, an arylalkyl group, an alkylaryl group, an alkoxy group, an aryloxy group, an arylalkyloxy group, an alkylaryloxy group, a polyalkyleneoxy group, a polyaryleneoxy group, a polyarylalkyleneoxy group, a polyalkylaryleneoxy group, a heterocyclic group, a silyl group, a siloxane group, a polysilylene group, or a polysiloxane group, and A is an anion to form a diazopyridone colorant of the formula

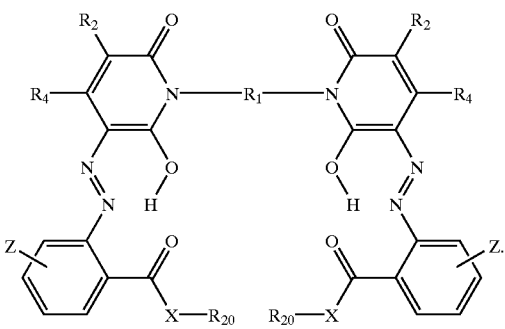

44. A process for preparing substituted pyridone compounds which comprises (a) admixing in the absence of a solvent (1) a diamine of the formula $H_2N$—$R_1$—$NH_2$ or a triamine of the formula $R_1(NH_2)_3$ wherein $R_1$ is an alkyl group, an aryl group, an arylalkyl group, or an alkylaryl group, and (2) a first ester of the formula

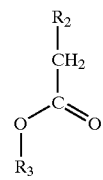

wherein $R_2$ is on electron withdrawing group and $R_3$ an alkyl group; (b) heating the mixture containing the amine and the first ester to form an intermediate compound of the formula

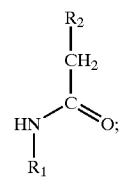

(c) admixing the intermediate compound with (1) a base and (2) a second ester of the formula

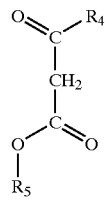

wherein $R_4$ is an alkyl group, an aryl group, an arylalkyl group, or an alkylaryl group and $R_5$ is an alkyl group, said second ester being present in a molar excess relative to the intermediate compound, sold base being present in a molar excess relative to the intermediate compound, and (d) heating the mixture containing the intermediate compound, the second ester, and the base to form a pyridone compound of the formula

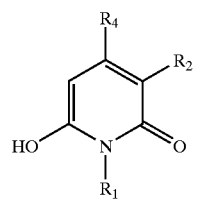

or a salt thereof.

* * * * *